(12) United States Patent
Shin et al.

(10) Patent No.: US 12,331,035 B2
(45) Date of Patent: Jun. 17, 2025

(54) BICYCLIC COMPOUND AND USE THEREOF

(71) Applicant: SK BIOPHARMACEUTICALS CO., LTD., Gyeonggi-do (KR)

(72) Inventors: Yong Je Shin, Gyeonggi-do (KR); Jin Hee Kim, Gyeonggi-do (KR); Jun Lee, Gyeonggi-do (KR); Hyun Suk Choi, Gyeonggi-do (KR); Se Hyuk Kim, Gyeonggi-do (KR); Eun Ji Kang, Gyeonggi-do (KR); Sook Kyung Park, Gyeonggi-do (KR); Ho Youl Lee, Gyeonggi-do (KR); Ho Yeon Lee, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 700 days.

(21) Appl. No.: 17/771,114

(22) PCT Filed: Oct. 22, 2020

(86) PCT No.: PCT/KR2020/014530
§ 371 (c)(1),
(2) Date: Apr. 22, 2022

(87) PCT Pub. No.: WO2021/080359
PCT Pub. Date: Apr. 29, 2021

(65) Prior Publication Data
US 2023/0023140 A1    Jan. 26, 2023

(30) Foreign Application Priority Data
Oct. 23, 2019    (KR) ........................ 10-2019-0132452

(51) Int. Cl.
| | | |
|---|---|---|
| *C07D 401/14* | (2006.01) | |
| *A61P 35/00* | (2006.01) | |
| *C07D 401/06* | (2006.01) | |
| *C07D 405/14* | (2006.01) | |
| *C07D 413/14* | (2006.01) | |
| *C07D 417/14* | (2006.01) | |
| *C07D 471/04* | (2006.01) | |
| *C07D 471/08* | (2006.01) | |
| *C07D 491/08* | (2006.01) | |
| *C07D 491/107* | (2006.01) | |
| *C07D 498/04* | (2006.01) | |

(52) U.S. Cl.
CPC ............ *C07D 401/14* (2013.01); *A61P 35/00* (2018.01); *C07D 401/06* (2013.01); *C07D 405/14* (2013.01); *C07D 413/14* (2013.01); *C07D 417/14* (2013.01); *C07D 471/04* (2013.01); *C07D 471/08* (2013.01); *C07D 491/08* (2013.01); *C07D 491/107* (2013.01); *C07D 498/04* (2013.01)

(58) Field of Classification Search
CPC ... C07D 401/06; C07D 405/14; C07D 413/14
See application file for complete search history.

(56) References Cited

FOREIGN PATENT DOCUMENTS

| | | |
|---|---|---|
| CN | 106279106 A | 1/2017 |
| WO | WO-2014/100716 A1 | 6/2014 |
| WO | WO-2017/153518 A1 | 9/2017 |
| WO | WO-2019/102494 A1 | 5/2019 |
| WO | WO-2019/173804 A1 | 9/2019 |

OTHER PUBLICATIONS

Kumar, A., et al.; "Solvent free, catalyst free, microwave or grinding assisted synthesis of bis-cyclic imide derivatives and their evaluation for anticancer activity", Bioorganic & Medicinal Chemistry Letters, 2017, vol. 27, pp. 501-504.
International Search Report from corresponding PCT Application No. PCT/KR2020/014530, dated Feb. 4, 2021.
Extended European Search Report from corresponding European Patent Application No. 20879400.8, dated Sep. 29, 2023.

*Primary Examiner* — John S Kenyon
*Assistant Examiner* — John D McAnany
(74) *Attorney, Agent, or Firm* — Harness, Dickey & Pierce, P.L.C.

(57) ABSTRACT

The present invention relates to a 6-6 bicyclic ring-containing compound derivative and use thereof. The compound according to the present invention acts as a PRMT5 inhibitor, and thus can be effectively used in the prevention or treatment of diseases caused by PRMT5.

15 Claims, No Drawings

BICYCLIC COMPOUND AND USE THEREOF

CROSS-REFERENCE TO RELATED APPLICATIONS

This application is a national phase application of PCT Application No. PCT/KR2020/014530, filed on Oct. 22, 2020, which claims the benefit and priority to Korean Patent Application No. 10-2019-0132452, filed on Oct. 23, 2019. The entire disclosures of the applications identified in this paragraph are incorporated herein by references.

TECHNICAL FIELD

The present invention relates to a compound derivative containing a 6-6 bicyclic ring and use thereof. The compound according to the present invention can be effectively used in the prevention or treatment of diseases caused by protein arginine methyltransferases 5 (PRMT5) by acting as a PRMT5 inhibitor.

BACKGROUND ART

PRMT (protein arginine methyltransferases) are enzymes that transfer methyl groups to arginine in target proteins using the cofactor SAM (S-adenosyl methionine). Up to now, there are a total of 9 PRMT isoforms (PRMT1-9) have been known, and these are largely divided into 3 types. It has been known that PRMT1, 2, 3, 4, 6 and 8—which belong to type I PRMT—cause monomethylation and asymmetric dimethylation of arginine, and PRMT5 and PRMT9 belonging to type II PRMT induce monomethylation and symmetric dimethylation of arginine. Meanwhile, PRMT7—which is a type III PRMT—mainly causes monomethylation of arginine. PRMT induces methylation of various substrates present in the nucleus and cytoplasm, thereby regulating important biological processes in cells such as cell proliferation, differentiation and splicing.

PRMT5 is a major arginine methyl group transfer enzyme among type II PRMTs. It forms a functional complex with methylosome protein 50 (MEP50) to cause methylation of the target protein. PRMT5 is involved in the formation of leukemia, lymphoma, glioblastoma, lung cancer and breast cancer by methylating target proteins including histone protein in the nucleus and non-histone protein such as p53, NFκB, PI3K/AKT and CRAF. Specifically, it is well known that cancer formation by PRMT5 occurs as the proliferation, differentiation, invasion and migration of tumor cells are promoted. In addition, according to several reports, it is known that the higher the expression of PRMT5 is, the poorer the prognosis of cancer patients is. To the contrary, it has been observed that when the expression of PRMT5 is inhibited, the proliferation of tumor cells can be suppressed.

Meanwhile, it has been recently reported that diseases other than cancer can also be mediated by PRMT5.

SUMMARY

Technical Problem

An object of the present invention is to provide a novel compound based on a 6-6 bicyclic ring showing excellent PRMT5 inhibitory effect, or an optical isomer, a stereoisomer or an isotopic variant thereof, or a pharmaceutically acceptable salt thereof.

Another object of the present invention is to provide a pharmaceutical composition comprising the above novel compound based on a 6-6 bicyclic ring, or an optical isomer, a stereoisomer or an isotopic variant thereof, or a pharmaceutically acceptable salt thereof as an active ingredient.

Solution to Problem

To achieve the above object, the present invention provides a compound represented by the following Formula 1, or an optical isomer, a stereoisomer or an isotopic variant thereof, or a pharmaceutically acceptable salt thereof:

[Formula 1]

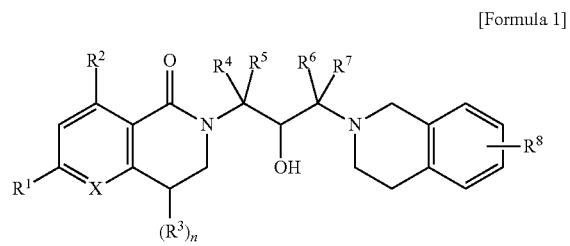

wherein
X is CH or N;
n is an integer from 0 to 2;
$R^1$ is -D-$R^9$ or

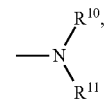

wherein D is a direct bond, —$CH_2$—, —O— or —C≡C—;
$R^9$ is halo, hydroxy, alkyl, hydroxyalkyl, dialkylaminoalkyl, saturated or unsaturated heterocyclyl, or saturated heterocyclyl-alkyl; the saturated or unsaturated heterocyclyl may be substituted with one or more substituents selected from halo, alkyl, alkoxy, haloalkyl, hydroxyalkyl, alkoxyalkyl, alkylcarbonyl, alkoxycarbonyl and saturated heterocyclyl;
$R^{10}$ and $R^{11}$ are each independently hydrogen, alkyl, cycloalkyl, hydroxyalkyl, cycloalkyl-alkyl, alkylcarbonyl, hydroxyalkylcarbonyl, aralkyl, saturated heterocyclyl, saturated or unsaturated heterocyclyl-alkyl, unsaturated heterocyclyl-carbonyl, or saturated heterocyclyl-alkylcarbonyl; or $R^{10}$ and $R^{11}$ together with nitrogen (N) atom to which they are attached may form saturated or unsaturated heterocyclyl; the saturated or unsaturated heterocyclyl may be substituted with one or more substituents selected from hydroxy, oxo, formyl (—CHO), cyano, alkyl, alkoxy, hydroxyalkyl, alkylcarbonyl, haloalkylcarbonyl, alkoxycarbonyl, alkylamino, alkylsulfonyl, alkoxyalkyl, aminocarbonyl, alkylcarbonylamino, alkylcarbonylalkylamino, alkoxyalkylalkylamino, dialkylamino, dialkylaminoalkyl, dialkylaminoalkoxy, dialkylaminocarbonyl and 4- to 10-membered, saturated heterocyclyl;
$R^2$ is hydrogen or halo;
$R^3$ is hydrogen, halo or alkyl, or together with carbon (C) atom to which they are attached may form cycloalkyl when n is 2;
$R^4$, $R^5$, $R^6$ and $R^7$ are each independently hydrogen or alkyl; and
$R^8$ is hydrogen, halo, alkyl, alkoxy or amino.

Unless indicated otherwise, the term "alkyl" used herein, either alone or in combination with additional terms (for example, haloalkyl), refers to a radical of a saturated aliphatic hydrocarbon group having, for example 1 to 7 carbon atoms of a linear or branched chain. For example, the alkyl may include such as methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl and 1,2-dimethylpropyl, but is not limited thereto.

Unless indicated otherwise, the term "cycloalkyl" used herein, either alone or in combination with additional terms (for example, cycloalkyl-alkyl), refers to a cyclic radical of a saturated aliphatic hydrocarbon group having, for example 3 to 7 carbon atoms. For example, the cycloalkyl may include cyclopropyl, cyclobutyl, cyclopentyl and cyclohexyl, but is not limited thereto.

Unless indicated otherwise, the term "aryl" used herein refers to an aromatic hydrocarbon group having, for example 6 to 12 carbon atoms. For example, the aryl may include phenyl and naphthyl, but is not limited thereto.

Unless indicated otherwise, the term "alkoxy" used herein refers to alkyloxy having, for example 1 to 7 carbon atoms.

Unless indicated otherwise, the term "halo" used herein, either alone or in combination with additional terms (for example, haloalkyl), refers to a radical of fluorine (F), chlorine (Cl), bromine (Br) or iodine (I).

Unless indicated otherwise, the term "oxo" used herein refers to the group of =O (that is, oxygen having a double bond). Two of oxo groups may be substituted for sulfur (S) atom to form a sulfonyl group.

Unless indicated otherwise stated, the term "saturated or unsaturated heterocyclyl" used herein refers to 3- to 24-membered hydrocarbon that is unsaturated or partially or fully saturated, forming a single or fused cyclic ring, and having one or more heteroatoms, for example 1 to 8 heteroatoms selected from the group consisting of nitrogen (N), oxygen (O) and sulfur (S) Specifically, the heterocyclyl may be a 4- to 10-membered hydrocarbon having 1 to 3 hetero atoms. The heterocycle may include a bridged structure or a spiro structure. In addition, the unsaturated heterocyclyl may include an aromatic hydrocarbon such as heteroaryl.

According to one embodiment of the present invention, the heterocyclyl may be pyridyl, morpholinyl, oxazepanyl, dihydropyridinyl, tetrahydropyridinyl, piperidyl, piperazinyl, tetrahydropyranyl, azetidinyl, pyrrolidinyl, tetrahydrofuranyl, oxazolidinyl, 2-oxa-6-azaspiro[3.3]heptan-6yl, thiomorpholinyl, 2,5,-diazabicyclo[2.2.1]heptanyl, 2-oxa-5-azabicyclo[2.2.1]heptanyl, diazepanyl, 4,7-diazaspiro[2.5]octanyl, 5,6,8,8a-tetrahydrooxazolo[3,4-a]pyrazinyl, azepanyl, 6,8-dihydro-5H-imidazo[1,2-a]pyrazinyl or oxetane, but is not limited thereto.

According to one aspect of the present invention, in the above Formula 1, $R^1$ is -D-$R^9$, wherein D is a direct bond, —$CH_2$—, —O— or —C≡C—;

$R^9$ is halo, hydroxy, $C_1$-$C_7$ alkyl, hydroxy-$C_1$-$C_7$ alkyl, di($C_1$-$C_7$ alkyl)amino-$C_1$-$C_7$ alkyl, 4- to 10-membered, saturated or unsaturated heterocyclyl, or 4- to 10-membered, saturated heterocyclyl-alkyl; the saturated or unsaturated heterocyclyl has 1 to 3 heteroatoms selected from N, O and S; and may be substituted with one or more substituents selected from halo, $C_1$-$C_7$ alkyl, $C_1$-$C_7$ alkoxy, halo-$C_1$-$C_7$ alkyl, hydroxy-$C_1$-$C_7$ alkyl, $C_1$-$C_7$ alkoxy-$C_1$-$C_7$ alkyl, $C_1$-$C_7$ alkylcarbonyl, $C_1$-$C_7$ alkoxycarbonyl, and 4- to 10-membered, saturated heterocyclyl having 1 to 3 heteroatoms selected from N, O and S.

According to another aspect of the present invention, in the above Formula 1, $R^1$ is -D-$R^9$, wherein D is a direct bond; $R^9$ is halo, hydroxy, $C_1$-$C_7$ alkyl or 4- to 10-membered, saturated or unsaturated heterocyclyl; the saturated or unsaturated heterocyclyl has 1 to 3 heteroatoms selected from N, O and S; and may be substituted with 1 to 3 substituents selected from halo, $C_1$-$C_7$ alkylcarbonyl and $C_1$-$C_7$ alkoxycarbonyl.

According to another aspect of the present invention, in the above Formula 1, $R^1$ is -D-$R^9$, wherein D is —$CH_2$—, —O— or —C≡C—; $R^9$ is hydroxy-$C_1$-$C_7$ alkyl, di($C_1$-$C_7$ alkyl)amino-$C_1$-$C_7$ alkyl, 4- to 10-membered, saturated or unsaturated heterocyclyl, or 4- to 10-membered, saturated or unsaturated heterocyclyl-$C_1$-$C_7$ alkyl; the saturated or unsaturated heterocyclyl has 1 to 3 heteroatoms selected from N, O and S; and may be substituted with 1 to 3 substituents selected from $C_1$-$C_7$ alkyl, $C_1$-$C_7$ alkoxy, halo-$C_1$-$C_7$ alkyl, hydroxy-$C_1$-$C_7$ alkyl, $C_1$-$C_7$ alkoxy-$C_1$-$C_7$ alkyl, $C_1$-$C_7$ alkylcarbonyl, $C_1$-$C_7$ alkoxycarbonyl and 4- to 10-membered, saturated heterocyclyl having 1 to 3 heteroatoms selected from N, O and S.

According to another aspect of the present invention, in the above Formula 1, $R^1$ is -D-$R^9$, wherein D is a direct bond, —$CH_2$—, —O— or —C≡C—;

$R^9$ is halo, hydroxy, $C_1$-$C_7$ alkyl, hydroxy-$C_1$-$C_7$ alkyl, di($C_1$-$C_7$ alkyl)amino-$C_1$-$C_7$ alkyl, 4- to 10-membered, saturated or unsaturated heterocyclyl, or 4- to 10-membered, saturated heterocyclyl-alkyl; and the saturated or unsaturated heterocyclyl is selected from the group consisting of pyridyl, morpholinyl, oxazepanyl, dihydropyridinyl, tetrahydropyridinyl, piperidyl, piperazinyl, tetrahydropyranyl, azetidinyl and pyrrolidinyl.

According to another aspect of the present invention, in the above Formula 1, $R^1$ is

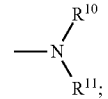

$R^{10}$ and $R^{11}$ are each independently hydrogen, $C_1$-$C_7$ alkyl, $C_3$-$C_7$ cycloalkyl, hydroxy-$C_1$-$C_7$ alkyl, $C_3$-$C_7$ cycloalkyl-$C_1$-$C_7$ alkyl, $C_1$-$C_7$ alkylcarbonyl, hydroxy-$C_1$-$C_7$ alkylcarbonyl, $C_6$-$C_{12}$ aryl-$C_1$-$C_7$ alkyl, saturated heterocyclyl, saturated or unsaturated heterocyclyl-$C_1$-$C_7$ alkyl, unsaturated heterocyclyl-carbonyl or saturated heterocyclyl-$C_1$-$C_7$ alkylcarbonyl; or $R^{10}$ and $R^{11}$ together with nitrogen (N) atom to which they are attached may form saturated or unsaturated heterocyclyl; the heterocyclyl may be substituted with 1 to 3 substituents selected from hydroxy, oxo, formyl (—CHO), cyano, $C_1$-$C_7$ alkyl, $C_1$-$C_7$ alkoxy, hydroxy-$C_1$-$C_7$ alkyl, $C_1$-$C_7$ alkylcarbonyl, halo-$C_1$-$C_7$ alkylcarbonyl, $C_1$-$C_7$ alkoxycarbonyl, $C_1$-$C_7$ alkylamino, $C_1$-$C_7$ alkylsulfonyl, $C_1$-$C_7$ alkoxy-$C_1$-$C_7$ alkyl, aminocarbonyl, $C_1$-$C_7$ alkylcarbonylamino, $C_1$-$C_7$ alkylcarbonyl-$C_1$-$C_7$ alkylamino, ($C_1$-$C_7$ alkoxy-$C_1$-$C_7$ alkyl)($C_1$-$C_7$ alkyl)amino, di($C_1$-$C_7$ alkyl)amino, di($C_1$-$C_7$ alkyl)

amino-$C_1$-$C_7$ alkyl, di($C_1$-$C_7$ alkyl)amino-$C_1$-$C_7$ alkoxy, di($C_1$-$C_7$ alkyl)aminocarbonyl and saturated heterocyclyl.

According to another aspect of the present invention, in the above Formula 1, $R^1$ is

$R^{10}$ and $R^{11}$ are each independently hydrogen, $C_1$-$C_7$ alkyl, $C_3$-$C_7$ cycloalkyl, hydroxy-$C_1$-$C_7$ alkyl, $C_3$-$C_7$ cycloalkyl-$C_1$-$C_7$ alkyl, $C_1$-$C_7$ alkylcarbonyl, hydroxy-$C_1$-$C_7$ alkylcarbonyl, $C_6$-$C_{12}$ aryl-$C_1$-$C_7$ alkyl, saturated heterocyclyl, saturated or unsaturated heterocyclyl-$C_1$-$C_7$ alkyl, unsaturated heterocyclyl-carbonyl or saturated heterocyclyl-$C_1$-$C_7$ alkylcarbonyl; or $R^{10}$ and $R^{11}$ together with nitrogen (N) atom to which they are attached may form saturated or unsaturated heterocyclyl; and the heterocyclyl is 4- to 10-membered, saturated or unsaturated hydrocarbon having 1 to 3 heteroatoms selected from N, O and S.

According to another aspect of the present invention, in the above Formula 1, $R^1$ is

$R^{10}$ and $R^{11}$ are each independently hydrogen, $C_1$-$C_7$ alkyl, $C_3$-$C_7$ cycloalkyl, hydroxy-$C_1$-$C_7$ alkyl, $C_3$-$C_7$ cycloalkyl-$C_1$-$C_7$ alkyl, $C_1$-$C_7$ alkylcarbonyl, hydroxy-$C_1$-$C_7$ alkylcarbonyl, $C_6$-$C_{12}$ aryl-$C_1$-$C_7$ alkyl, saturated heterocyclyl, saturated or unsaturated heterocyclyl-$C_1$-$C_7$ alkyl, unsaturated heterocyclyl-carbonyl or saturated heterocyclyl-$C_1$-$C_7$ alkylcarbonyl; or $R^{10}$ and $R^{11}$ together with nitrogen (N) atom to which they are attached may form saturated or unsaturated heterocyclyl; and the heterocyclyl selected from the group consisting of pyrrolidinyl, morpholinyl, tetrahydropyranyl, pyridyl, piperazinyl, azetidinyl, piperidyl, tetrahydrofuranyl, oxazolidinyl, 2-oxa-6-azaspiro[3.3]heptan-6yl, thiomorpholinyl, 2,5-diazabicyclo[2.2.1]heptanyl, 2-oxa-5-azabicyclo[2.2.1]heptanyl, diazepanyl, 4,7-diazaspiro[2.5]octanyl, 5,6,8,8a-tetrahydrooxazolo[3,4-a]pyrazinyl, azepanyl, 6,8-dihydro-5H-imidazo[1,2-a]pyrazinyl and oxetanyl.

According to another aspect of the present invention, in the above Formula 1, $R^2$ is hydrogen or halo;

$R^3$ is hydrogen, halo or $C_1$-$C_7$ alkyl; or together with carbon (C) atom to which they are attached may form $C_3$-$C_7$ cycloalkyl when n is 2;

$R^4$, $R^5$, $R^6$ and $R^7$ are each independently hydrogen or $C_1$-$C_7$ alkyl; and $R^8$ is hydrogen, halo, $C_1$-$C_7$ alkyl, $C_1$-$C_7$ alkoxy or amino.

Representative examples of the compound of Formula 1 according to the present invention may include compounds shown in Table 1, but are not limited thereto.

TABLE 1

| No. | Compound Name |
|---|---|
| 1 | 6-bromo-2-[(2R)-3-(3,4-dihydro-1H-isoquinolin-2-yl)-2-hydroxy-propyl]-3,4-dihydroisoquinolin-1-one |
| 2 | 2-[(2R)-3-(3,4-dihydro-1H-isoquinolin-2-yl)-2-hydroxy-propyl]-6-pyrrolidin-1-yl-3,4-dihydroisoquinolin-1-one |
| 3 | 6-(cyclohexylamino)-2-[(2R)-3-(3,4-dihydro-1H-isoquinolin-2-yl)-2-hydroxy-propyl]-3,4-dihydroisoquinolin-1-one |
| 4 | 2-[(2R)-3-(3,4-dihydro-1H-isoquinolin-2-yl)-2-hydroxy-propyl]-6-morpholino-3,4-dihydroisoquinolin-1-one |
| 5 | 2-[(2R)-3-(3,4-dihydro-1H-isoquinolin-2-yl)-2-hydroxy-propyl]-6-(tetrahydropyran-4-ylamino)-3,4-dihydroisoquinolin-1-one |
| 6 | 6-(cyclohexylmethylamino)-2-[(2R)-3-(3,4-dihydro-1H-isoquinolin-2-yl)-2-hydroxy-propyl]-3,4-dihydroisoquinolin-1-one |
| 7 | 6-(benzylamino)-2-[(2R)-3-(3,4-dihydro-1H-isoquinolin-2-yl)-2-hydroxy-propyl]-3,4-dihydroisoquinolin-1-one |
| 8 | 2-[(2R)-3-(3,4-dihydro-1H-isoquinolin-2-yl)-2-hydroxy-propyl]-6-(4-pyridyl)-3,4-dihydroisoquinolin-1-one |
| 9 | 2-[(2R)-3-(3,4-dihydro-1H-isoquinolin-2-yl)-2-hydroxy-propyl]-6-(3-pyridyl)-3,4-dihydroisoquinolin-1-one |
| 10 | 2-[(2R)-3-(3,4-dihydro-1H-isoquinolin-2-yl)-2-hydroxy-propyl]-6-(4-pyridylmethylamino)-3,4-dihydroisoquinolin-1-one |
| 11 | 6-[cyclohexyl(methyl)amino]-2-[(2R)-3-(3,4-dihydro-1H-isoquinolin-2-yl)-2-hydroxy-propyl]-3,4-dihydroisoquinolin-1-one |
| 12 | 2-[(2R)-3-(3,4-dihydro-1H-isoquinolin-2-yl)-2-hydroxy-propyl]-6-(2-fluoro-4-pyridyl)-3,4-dihydroisoquinolin-1-one |
| 13 | 2-[(2R)-3-(3,4-dihydro-1H-isoquinolin-2-yl)-2-hydroxy-propyl]-6-propyl-3,4-dihydroisoquinolin-1-one |
| 14 | 2-[(2R)-3-(3,4-dihydro-1H-isoquinolin-2-yl)-2-hydroxy-propyl]-6-[(2R,6S)-2,6-dimethylmorpholin-4-yl]-3,4-dihydroisoquinolin-1-one |
| 15 | 2-[(2R)-3-(3,4-dihydro-1H-isoquinolin-2-yl)-2-hydroxy-propyl]-6-(6-fluoro-3-pyridyl)-3,4-dihydroisoquinolin-1-one |
| 16 | 2-[(2R)-3-(3,4-dihydro-1H-isoquinolin-2-yl)-2-hydroxy-propyl]-6-[(2R)-2-methylmorpholin-4-yl]-3,4-dihydroisoquinolin-1-one |
| 17 | 2-[(2R)-3-(3,4-dihydro-1H-isoquinolin-2-yl)-2-hydroxy-propyl]-6-(4-methylpiperazin-1-yl)-3,4-dihydroisoquinolin-1-one |

TABLE 1-continued

| No. | Compound Name |
|---|---|
| 18 | 2-[(2R)-3-(3,4-dihydro-1H-isoquinolin-2-yl)-2-hydroxy-propyl]-6-(2-oxopyrrolidin-1-yl)-3,4-dihydroisoquinolin-1-one |
| 19 | N-[2-[(2R)-3-(3,4-dihydro-1H-isoquinolin-2-yl)-2-hydroxy-propyl]-1-oxo-3,4-dihydroisoquinoline-6-yl]-2,2-dimethyl-propanamide |
| 20 | 2-[(2R)-3-(3,4-dihydro-1H-isoquinolin-2-yl)-2-hydroxy-propyl]-6-(2-oxoazetidin-1-yl)-3,4-dihydroisoquinolin-1-one |
| 21 | 2-[(2R)-3-(3,4-dihydro-1H-isoquinolin-2-yl)-2-hydroxy-propyl]-6-(2-oxo-1-piperidyl)-3,4-dihydroisoquinolin-1-one |
| 22 | 2-[(2R)-3-(3,4-dihydro-1H-isoquinolin-2-yl)-2-hydroxy-propyl]-6-(3-pyridylmethylamino)-3,4-dihydroisoquinolin-1-one |
| 23 | 2-[(2R)-3-(3,4-dihydro-1H-isoquinolin-2-yl)-2-hydroxy-propyl]-6-(tetrahydropyran-4-ylmethylamino)-3,4-dihydroisoquinolin-1-one |
| 24 | 6-[(1-acetyl-4-piperidyl)methylamino]-2-[(2R)-3-(3,4-dihydro-1H-isoquinolin-2-yl)-2-hydroxy-propyl]-3,4-dihydroisoquinolin-1-one |
| 25 | 2-[(2R)-3-(3,4-dihydro-1H-isoquinolin-2-yl)-2-hydroxy-propyl]-6-[(2-hydroxy-2-methyl-propyl)amino]-3,4-dihydroisoquinolin-1-one |
| 26 | N-[2-[(2R)-3-(3,4-dihydro-1H-isoquinolin-2-yl)-2-hydroxy-propyl]-1-oxo-3,4-dihydroisoquinolin-6-yl]pyridine-3-carboxamide |
| 27 | N-[2-[(2R)-3-(3,4-dihydro-1H-isoquinolin-2-yl)-2-hydroxy-propyl]-1-oxo-3,4-dihydroisoquinolin-6-yl]pyridine-4-carboxamide |
| 28 | 2-[(2R)-3-(3,4-dihydro-1H-isoquinolin-2-yl)-2-hydroxy-propyl]-6-(3,5-dimethyl-1-piperidyl)-3,4-dihydroisoquinolin-1-one |
| 29 | 2-[(2R)-3-(3,4-dihydro-1H-isoquinolin-2-yl)-2-hydroxy-propyl]-6-(3,5-dimethylpiperazin-1-yl)-3,4-dihydroisoquinolin-1-one |
| 30 | 2-[(2R)-3-(3,4-dihydro-1H-isoquinolin-2-yl)-2-hydroxy-propyl]-6-(tetrahydrofuran-3-ylmethylamino)-3,4-dihydroisoquinolin-1-one |
| 31 | 2-[(2R)-3-(3,4-dihydro-1H-isoquinolin-2-yl)-2-hydroxy-propyl]-6-(4-piperidylmethylamino)-3,4-dihydroisoquinolin-1-one |
| 32 | 6-[(1-acetyl-4-piperidyl)amino]-2-[(2R)-3-(3,4-dihydro-1H-isoquinolin-2-yl)-2-hydroxy-propyl]-3,4-dihydroisoquinolin-1-one |
| 33 | N-[2-[(2R)-3-(3,4-dihydro-1H-isoquinolin-2-yl)-2-hydroxy-propyl]-1-oxo-3,4-dihydroisoquinolin-6-yl]-2-morpholino-acetamide |
| 34 | 2-[(2R)-3-(3,4-dihydro-1H-isoquinolin-2-yl)-2-hydroxy-propyl]-6-(4-piperidylamino)-3,4-dihydroisoquinolin-1-one |
| 35 | 2-[(2R)-3-(3,4-dihydro-1H-isoquinolin-2-yl)-2-hydroxy-propyl]-6-[4-(hydroxymethyl)-1-piperidyl]-3,4-dihydroisoquinolin-1-one |
| 36 | 2-[(2R)-3-(3,4-dihydro-1H-isoquinolin-2-yl)-2-hydroxy-propyl]-6-[3-(hydroxymethyl)-1-piperidyl]-3,4-dihydroisoquinolin-1-one |
| 37 | 2-[(2R)-3-(3,4-dihydro-1H-isoquinolin-2-yl)-2-hydroxy-propyl]-6-(4-hydroxy-1-piperidyl)-3,4-dihydroisoquinolin-1-one |
| 38 | 2-[(2R)-3-(3,4-dihydro-1H-isoquinolin-2-yl)-2-hydroxy-propyl]-6-(3-hydroxy-1-piperidyl)-3,4-dihydroisoquinolin-1-one |
| 39 | 2-[(2R)-3-(3,4-dihydro-1H-isoquinolin-2-yl)-2-hydroxy-propyl]-6-oxazolidin-3-yl-3,4-dihydroisoquinolin-1-one |
| 40 | 2-[(2R)-3-(3,4-dihydro-1H-isoquinolin-2-yl)-2-hydroxy-propyl]-6-(3-methylmorpholin-4-yl)-3,4-dihydroisoquinolin-1-one |
| 41 | N-[2-[(2R)-3-(3,4-dihydro-1H-isoquinolin-2-yl)-2-hydroxy-propyl]-1-oxo-3,4-dihydroisoquinolin-6-yl]-2-hydroxy-acetamide |
| 42 | N-[2-[(2R)-3-(3,4-dihydro-1H-isoquinolin-2-yl)-2-hydroxy-propyl]-1-oxo-3,4-dihydroisoquinolin-6-yl]acetamide |
| 43 | 2-[(2R)-3-(3,4-dihydro-1H-isoquinolin-2-yl)-2-hydroxy-propyl]-6-(morpholinomethyl)-3,4-dihydroisoquinolin-1-one |
| 44 | 2-[(2R)-3-(3,4-dihydro-1H-isoquinolin-2-yl)-2-hydroxy-propyl]-6-(2-oxa-6-azaspiro[3.3]heptan-6-yl)-3,4-dihydroisoquinolin-1-one |
| 45 | 3-[2-[(2R)-3-(3,4-dihydro-1H-isoquinolin-2-yl)-2-hydroxy-propyl]-1-oxo-3,4-dihydroisoquinolin-6-yl]oxazolidin-2-one |
| 46 | 2-[(2R)-3-(3,4-dihydro-1H-isoquinolin-2-yl)-2-hydroxy-propyl]-6-[3-(hydroxymethyl)azetidin-1-yl]-3,4-dihydroisoquinolin-1-one |
| 47 | 2-[(2R)-3-(3,4-dihydro-1H-isoquinolin-2-yl)-2-hydroxy-propyl]-6-[(2S)-2-methylmorpholin-4-yl]-3,4-dihydroisoquinolin-1-one |
| 48 | 2-[(2R)-3-(3,4-dihydro-1H-isoquinolin-2-yl)-2-hydroxy-propyl]-6-(4-methoxy-1-piperidyl)-3,4-dihydroisoquinolin-1-one |
| 49 | 2-[(2R)-3-(3,4-dihydro-1H-isoquinolin-2-yl)-2-hydroxy-propyl]-6-(1,1-dioxo-1,4-thiazinan-4-yl)-3,4-dihydroisoquinolin-1-one |
| 50 | 2-[(2R)-3-(3,4-dihydro-1H-isoquinolin-2-yl)-2-hydroxy-propyl]-6-(tetrahydrofuran-3-ylamino)-3,4-dihydroisoquinolin-1-one |
| 51 | 2-[(2R)-3-(3,4-dihydro-1H-isoquinolin-2-yl)-2-hydroxy-propyl]-6-(oxetan-3-ylamino)-3,4-dihydroisoquinolin-1-one |
| 52 | 6-(4-acetylpiperazin-1-yl)-2-[(2R)-3-(3,4-dihydro-1H-isoquinolin-2-yl)-2-hydroxy-propyl]-3,4-dihydroisoquinolin-1-one |
| 53 | tert-butyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate |
| 54 | 2-[(2R)-3-(3,4-dihydro-1H-isoquinolin-2-yl)-2-hydroxy-propyl]-6-(1,4-oxazepan-4-ylmethyl)-3,4-dihydroisoquinolin-1-one |
| 55 | 2-[(2R)-3-(3,4-dihydro-1H-isoquinolin-2-yl)-2-hydroxy-propyl]-6-(4-methyl-3-oxo-piperazin-1-yl)-3,4-dihydroisoquinolin-1-one |
| 56 | tert-butyl 4-[2-[(2R)-3-(3,4-dihydro-1H-isoquinolin-2-yl)-2-hydroxy-propyl]-1-oxo-3,4-dihydroisoquinolin-6-yl]-3,6-dihydro-2H-pyridine-1-carboxylate |

TABLE 1-continued

| No. | Compound Name |
|---|---|
| 57 | 2-[(2R)-3-(3,4-dihydro-1H-isoquinolin-2-yl)-2-hydroxy-propyl]-6-(1,2,3,6-tetrahydropyridin-4-yl)-3,4-dihydroisoquinolin-1-one |
| 58 | 2-[(2R)-3-(3,4-dihydro-1H-isoquinolin-2-yl)-2-hydroxy-propyl]-6-piperazin-1-yl-3,4-dihydroisoquinolin-1-one |
| 59 | 2-[(2R)-3-(3,4-dihydro-1H-isoquinolin-2-yl)-2-hydroxy-propyl]-6-(4-methylsulfonylpiperazin-1-yl)-3,4-dihydroisoquinolin-1-one |
| 60 | methyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate |
| 61 | 6-(1-acetyl-3,6-dihydro-2H-pyridin-4-yl)-2-[(2R)-3-(3,4-dihydro-1H-isoquinolin-2-yl)-2-hydroxy-propyl]-3,4-dihydroisoquinolin-1-one |
| 62 | 2-[(2R)-3-(3,4-dihydro-1H-isoquinolin-2-yl)-2-hydroxy-propyl]-6-[4-(2,2,2-trifluoroacetyl)piperazin-1-yl]-3,4-dihydroisoquinolin-1-one |
| 63 | tert-butyl 4-[2-[(2R)-3-(3,4-dihydro-1H-isoquinolin-2-yl)-2-hydroxy-propyl]-1-oxo-3,4-dihydroisoquinolin-6-yl]piperidine-1-carboxylate |
| 64 | [(2R)-3-(3,4-dihydro-1H-isoquinolin-2-yl)-2-hydroxy-propyl]-6-(4-isopropylpiperazin-1-yl)-3,4-dihydroisoquinolin-1-one |
| 65 | ethyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate |
| 66 | 2-[(2R)-3-(3,4-dihydro-1H-isoquinolin-2-yl)-2-hydroxy-propyl]-6-[(4-methoxy-1-piperidyl)methyl]-3,4-dihydroisoquinolin-1-one |
| 67 | 6-(1-acetyl-4-piperidyl)-2-[(2R)-3-(3,4-dihydro-1H-isoquinolin-2-yl)-2-hydroxy-propyl]-3,4-dihydroisoquinolin-1-one |
| 68 | 6-[(4-acetylpiperazin-1-yl)methyl]-2-[(2R)-3-(3,4-dihydro-1H-isoquinolin-2-yl)-2-hydroxy-propyl]-3,4-dihydroisoquinolin-1-one |
| 69 | 2-[(2R)-3-(3,4-dihydro-1H-isoquinolin-2-yl)-2-hydroxy-propyl]-6-(4-propanoylpiperazin-1-yl)-3,4-dihydroisoquinolin-1-one |
| 70 | 2-[(2R)-3-(3,4-dihydro-1H-isoquinolin-2-yl)-2-hydroxy-propyl]-6-[4-(2-methylpropanoyl)piperazin-1-yl]-3,4-dihydroisoquinolin-1-one |
| 71 | 2-[(2R)-3-(3,4-dihydro-1H-isoquinolin-2-yl)-2-hydroxy-propyl]-6-[4-(2,2-dimethylpropanoyl)piperazin-1-yl]-3,4-dihydroisoquinolin-1-one |
| 72 | tert-butyl 5-[2-[(2R)-3-(3,4-dihydro-1H-isoquinolin-2-yl)-2-hydroxy-propyl]-1-oxo-3,4-dihydroisoquinolin-6-yl]-2,5-diazabicyclo[2.2.1]heptane-2-carboxylate |
| 73 | 2-[(2R)-3-(3,4-dihydro-1H-isoquinolin-2-yl)-2-hydroxy-propyl]-6-(2-oxa-5-azabicyclo[2.2.1]heptan-5-yl)-3,4-dihydroisoquinolin-1-one |
| 74 | 2-[(2R)-3-(3,4-dihydro-1H-isoquinolin-2-yl)-2-hydroxy-propyl]-6-hydroxy-3,4-dihydroisoquinolin-1-one |
| 75 | 2-chloro-6-[(2R)-3-(3,4-dihydro-1H-isoquinolin-2-yl)-2-hydroxy-propyl]-7,8-dihydro-1,6-naphthyridin-5-one |
| 76 | 6-(2,5-diazabicyclo[2.2.1]heptan-2-yl)-2-[(2R)-3-(3,4-dihydro-1H-isoquinolin-2-yl)-2-hydroxy-propyl]-3,4-dihydroisoquinolin-1-one |
| 77 | 2-[(2R)-3-(3,4-dihydro-1H-isoquinolin-2-yl)-2-hydroxy-propyl]-6-(3-piperidylamino)-3,4-dihydroisoquinolin-1-one |
| 78 | tert-butyl 4-[2-[(2R)-3-(3,4-dihydro-1H-isoquinolin-2-yl)-2-hydroxy-propyl]-1-oxo-3,4-dihydroisoquinolin-6-yl]-1,4-diazepane-1-carboxylate |
| 79 | 2-[(2R)-3-(3,4-dihydro-1H-isoquinolin-2-yl)-2-hydroxy-propyl]-6-(4-methyl-3-oxo-1,4-diazepan-1-yl)-3,4-dihydroisoquinolin-1-one |
| 80 | 6-(4-acetyl-1,4-diazepan-1-yl)-2-[(2R)-3-(3,4-dihydro-1H-isoquinolin-2-yl)-2-hydroxy-propyl]-3,4-dihydroisoquinolin-1-one |
| 81 | 6-(5-acetyl-2,5-diazabicyclo[2.2.1]heptan-2-yl)-2-[(2R)-3-(3,4-dihydro-1H-isoquinolin-2-yl)-2-hydroxy-propyl]-3,4-dihydroisoquinolin-1-one |
| 82 | 6-(4-acetyl-4,7-diazaspiro[2.5]octan-7-yl)-2-[(2R)-3-(3,4-dihydro-1H-isoquinolin-2-yl)-2-hydroxy-propyl]-3,4-dihydroisoquinolin-1-one |
| 83 | 6-[(1-acetyl-4-piperidyl)methoxy]-2-[(2R)-3-(3,4-dihydro-1H-isoquinolin-2-yl)-2-hydroxy-propyl]-3,4-dihydroisoquinolin-1-one |
| 84 | 2-[(2R)-3-(3,4-dihydro-1H-isoquinolin-2-yl)-2-hydroxy-propyl]-6-(4-methyl-5-oxo-1,4-diazepan-1-yl)-3,4-dihydroisoquinolin-1-one |
| 85 | 2-[(2R)-3-(3,4-dihydro-1H-isoquinolin-2-yl)-2-hydroxy-propyl]-6-(4-isopropyl-3-oxo-piperazin-1-yl)-3,4-dihydroisoquinolin-1-one |
| 86 | 6-(4-acetyl-2-oxo-piperazin-1-yl)-2-[(2R)-3-(3,4-dihydro-1H-isoquinolin-2-yl)-2-hydroxy-propyl]-3,4-dihydroisoquinolin-1-one |
| 87 | 4-[2-[(2R)-3-(3,4-dihydro-1H-isoquinolin-2-yl)-2-hydroxy-propyl]-1-oxo-3,4-dihydroisoquinolin-6-yl]piperazine-1-carbaldehyde |
| 88 | 2-(4-acetylpiperazin-1-yl)-6-[(2R)-3-(3,4-dihydro-1H-isoquinolin-2-yl)-2-hydroxy-propyl]-7,8-dihydro-1,6-naphthyridin-5-one |
| 89 | 6-[(2R)-3-(3,4-dihydro-1H-isoquinolin-2-yl)-2-hydroxy-propyl]-2-morpholino-7,8-dihydro-1,6-naphthyridin-5-one |
| 90 | N-[1-[2-[(2R)-3-(3,4-dihydro-1H-isoquinolin-2-yl)-2-hydroxy-propyl]-1-oxo-3,4-dihydroisoquinolin-6-yl]-4-piperidyl]-N-methyl-acetamide |
| 91 | 2-[(2R)-3-(3,4-dihydro-1H-isoquinolin-2-yl)-2-hydroxy-propyl]-6-tetrahydropyran-4-yloxy-3,4-dihydroisoquinolin-1-one |
| 92 | N-[1-[2-[(2R)-3-(3,4-dihydro-1H-isoquinolin-2-yl)-2-hydroxy-propyl]-1-oxo-3,4-dihydroisoquinolin-6-yl]-4-piperidyl]acetamide |
| 93 | 6-[(1-acetyl-3-piperidyl)amino]-2-[(2R)-3-(3,4-dihydro-1H-isoquinolin-2-yl)-2-hydroxy-propyl]-3,4-dihydroisoquinolin-1-one |
| 94 | 7-[2-[(2R)-3-(3,4-dihydro-1H-isoquinolin-2-yl)-2-hydroxy-propyl]-1-oxo-3,4-dihydroisoquinolin-6-yl]-5,6,8,8a-tetrahydro-1H-oxazolo[3,4-a]pyrazin-3-one |
| 95 | 6-[(1-acetyl-4-piperidyl)oxy]-2-[(2R)-3-(3,4-dihydro-1H-isoquinolin-2-yl)-2-hydroxy-propyl]-3,4-dihydroisoquinolin-1-one |

TABLE 1-continued

| No. | Compound Name |
|---|---|
| 96 | 6-(1-acetylazetidin-3-yl)oxy-2-[(2R)-3-(3,4-dihydro-1H-isoquinolin-2-yl)-2-hydroxy-propyl]-3,4-dihydroisoquinolin-1-one |
| 97 | 1-[2-[(2R)-3-(3,4-dihydro-1H-isoquinolin-2-yl)-2-hydroxy-propyl]-1-oxo-3,4-dihydroisoquinolin-6-yl]-N,N-dimethyl-piperidine-4-carboxamide |
| 98 | 6-[(1-acetylazepan-4-yl)amino]-2-[(2R)-3-(3,4-dihydro-1H-isoquinolin-2-yl)-2-hydroxy-propyl]-3,4-dihydroisoquinolin-1-one |
| 99 | 6-[(1-acetylpyrrolidin-3-yl)amino]-2-[(2R)-3-(3,4-dihydro-1H-isoquinolin-2-yl)-2-hydroxy-propyl]-3,4-dihydroisoquinolin-1-one |
| 100 | 4-[2-[(2R)-3-(3,4-dihydro-1H-isoquinolin-2-yl)-2-hydroxy-propyl]-1-oxo-3,4-dihydroisoquinolin-6-yl]piperazine-1-carboxamide |
| 101 | 4-[2-[(2R)-3-(3,4-dihydro-1H-isoquinolin-2-yl)-2-hydroxy-propyl]-1-oxo-3,4-dihydroisoquinolin-6-yl]piperazine-1-carbonitrile |
| 102 | 6-(6,8-dihydro-5H-imidazo[1,2-a]pyrazin-7-yl)-2-[(2R)-3-(3,4-dihydro-1H-isoquinoline-2-yl)-2-hydroxy-propyl]-3,4-dihydroisoquinolin-1-one |
| 103 | 2-[(2R)-3-(3,4-dihydro-1H-isoquinolin-2-yl)-2-hydroxy-propyl]-6-(3,4-dimethyl-5-oxo-piperazin-1-yl)-3,4-dihydroisoquinolin-1-one |
| 104 | 6-(4-acetylpiperazin-1-yl)-2-[(2R)-3-(3,4-dihydro-1H-isoquinolin-2-yl)-2-hydroxy-propyl]-4,4-dimethyl-3H-isoquinolin-1-one |
| 105 | 6-(4-acetylpiperazin-1-yl)-2-[(2R)-3-(3,4-dihydro-1H-isoquinolin-2-yl)-2-hydroxy-propyl]spiro[3H-isoquinoline-4,1'-cyclopropane]-1-one |
| 106 | 2-[(2R)-3-(3,4-dihydro-1H-isoquinolin-2-yl)-2-hydroxy-propyl]-6-(4-pyrrolidin-1-yl-1-piperidyl)-3,4-dihydroisoquinolin-1-one |
| 107 | 2-[(2R)-3-(3,4-dihydro-1H-isoquinolin-2-yl)-2-hydroxy-propyl]-6-[4-(1-piperidyl)-1-piperidyl]-3,4-dihydroisoquinolin-1-one |
| 108 | 2-[(2R)-3-(3,4-dihydro-1H-isoquinolin-2-yl)-2-hydroxy-propyl]-6-(4-morpholino-1-piperidyl)-3,4-dihydroisoquinolin-1-one |
| 109 | 2-[(2R)-3-(3,4-dihydro-1H-isoquinolin-2-yl)-2-hydroxy-propyl]-6-[4-(2-methoxyethyl)piperazin-1-yl]-3,4-dihydroisoquinolin-1-one |
| 110 | 2-[(2R)-3-(3,4-dihydro-1H-isoquinolin-2-yl)-2-hydroxy-propyl]-6-[4-(dimethylamino)-1-piperidyl]-3,4-dihydroisoquinolin-1-one |
| 111 | 2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one |
| 112 | 2-[(2R)-3-(3,4-dihydro-1H-isoquinolin-2-yl)-2-hydroxy-propyl]-4,4-dimethyl-6-morpholino-3H-isoquinolin-1-one |
| 113 | 2-[(2R)-3-(3,4-dihydro-1H-isoquinolin-2-yl)-2-hydroxy-propyl]-6-(2-morpholinoethoxy)-3,4-dihydroisoquinolin-1-one |
| 114 | 2-[(2R)-3-(3,4-dihydro-1H-isoquinolin-2-yl)-2-hydroxy-propyl]-6-[(1-ethyl-4-piperidyl)oxy]-3,4-dihydroisoquinolin-1-one |
| 115 | 2-[(2R)-3-(3,4-dihydro-1H-isoquinolin-2-yl)-2-hydroxy-propyl]-6-[(1-ethyl-4-piperidyl)methyloxy]-3,4-dihydroisoquinolin-1-one |
| 116 | 2-[(2R)-3-(3,4-dihydro-1H-isoquinolin-2-yl)-2-hydroxy-propyl]-6-[3-(dimethylamino)-1-piperidyl]-3,4-dihydroisoquinolin-1-one |
| 117 | 2-[(2R)-3-(3,4-dihydro-1H-isoquinolin-2-yl)-2-hydroxy-propyl]-6-[4-[(dimethylamino)methyl]-1-piperidyl]-3,4-dihydroisoquinolin-1-one |
| 118 | 6-[4-(diethylamino)-1-piperidyl]-2-[(2R)-3-(3,4-dihydro-1H-isoquinolin-2-yl)-2-hydroxy-propyl]-3,4-dihydroisoquinolin-1-one |
| 119 | 2-[(2R)-3-(3,4-dihydro-1H-isoquinolin-2-yl)-2-hydroxy-propyl]-6-[4-[2-(dimethylamino)ethoxy]-1-piperidyl]-3,4-dihydroisoquinolin-1-one |
| 120 | 2-[(2R)-3-(3,4-dihydro-1H-isoquinolin-2-yl)-2-hydroxy-propyl]-6-[4-[2-methoxyethyl(methyl)amino]-1-piperidyl]-3,4-dihydroisoquinolin-1-one |
| 121 | 2-[(2R)-3-(3,4-dihydro-1H-isoquinolin-2-yl)-2-hydroxy-propyl]-6-[4-(oxetan-3-yl)piperazin-1-yl]-3,4-dihydroisoquinolin-1-one |
| 122 | 2-[(2R)-3-(3,4-dihydro-1H-isoquinolin-2-yl)-2-hydroxy-propyl]-6-(4-tetrahydropyran-4-ylpiperazin-1-yl)-3,4-dihydroisoquinolin-1-one |
| 123 | 6-[4-(diethylamino)-1-piperidyl]-2-[(2R)-3-(3,4-dihydro-1H-isoquinolin-2-yl)-2-hydroxy-propyl]-4,4-dimethyl-3H-isoquinolin-1-one |
| 124 | 2-[(2R)-3-(3,4-dihydro-1H-isoquinolin-2-yl)-2-hydroxy-propyl]-4,4-dimethyl-6-(4-pyrrolidin-1-yl-1-piperidyl)-3H-isoquinolin-1-one |
| 125 | 4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde |
| 126 | 2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one; dihydrochloride |
| 127 | 2-[(2R)-3-(3,4-dihydro-1H-isoquinolin-2-yl)-2-hydroxy-propyl]-6-(4-tetrahydrofuran-3-ylpiperazin-1-yl)-3,4-dihydroisoquinolin-1-one |
| 128 | 6-(4-acetylpiperazin-1-yl)-2-[(2R)-3-(3,4-dihydro-1H-isoquinolin-2-yl)-2-hydroxy-propyl]-8-fluoro-3,4-dihydroisoquinolin-1-one |
| 129 | 6-(4-acetylpiperazin-1-yl)-2-[3-(3,4-dihydro-1H-isoquinolin-2-yl)-2-hydroxy-1-methyl-propyl]-3,4-dihydroisoquinolin-1-one |
| 130 | 4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde; hydrochloride |
| 131 | 2-[(2R)-3-(3,4-dihydro-1H-isoquinolin-2-yl)-2-hydroxy-propyl]-6-[(1-ethyl-4-piperidyl)oxy]-4,4-dimethyl-3H-isoquinolin-1-one |
| 132 | 2-[(2R)-3-(3,4-dihydro-1H-isoquinolin-2-yl)-2-hydroxy-propyl]-4,4-difluoro-6-morpholino-3H-isoquinolin-1-one |
| 133 | 2-[(2R)-3-(3,4-dihydro-1H-isoquinolin-2-yl)-2-hydroxy-propyl]-6-(1-methylpyrrolidin-3-yl)oxy-3,4-dihydroisoquinolin-1-one |
| 134 | 2-[(2R)-3-(3,4-dihydro-1H-isoquinolin-2-yl)-2-hydroxy-propyl]-6-(1-ethylpyrrolidin-3-yl)oxy-3,4-dihydroisoquinolin-1-one |

TABLE 1-continued

| No. | Compound Name |
|---|---|
| 135 | 2-[(2R)-3-(3,4-dihydro-1H-isoquinolin-2-yl)-2-hydroxy-propyl]-6-[(1-methyl-4-piperidyl)oxy]-3,4-dihydroisoquinolin-1-one |
| 136 | 2-[(2R)-3-(3,4-dihydro-1H-isoquinolin-2-yl)-2-hydroxy-propyl]-6-[[1-(oxetan-3-yl)-4-piperidyl]oxy]-3,4-dihydroisoquinolin-1-one |
| 137 | 2-[(2R)-3-(3,4-dihydro-1H-isoquinolin-2-yl)-2-hydroxypropyl]-6-(3-hydroxyprop-1-ynyl)-3,4-dihydroisoquinolin-1-one |
| 138 | 2-[(2R)-3-(3,4-dihydro-1H-isoquinolin-2-yl)-2-hydroxypropyl]-6-[2-(4-pyridyl)ethynyl]-3,4-dihydroisoquinolin-1-one |
| 139 | 2-[(2R)-3-(3,4-dihydro-1H-isoquinolin-2-yl)-2-hydroxypropyl]-6-[(1-methyl-3-piperidyl)oxy]-3,4-dihydroisoquinolin-1-one |
| 140 | 2-[(2R)-3-(3,4-dihydro-1H-isoquinolin-2-yl)-2-hydroxypropyl]-6-[[1-(2-fluoroethyl)-3-piperidyl]oxy]-3,4-dihydroisoquinolin-1-one |
| 141 | 2-[(2R)-3-(3,4-dihydro-1H-isoquinolin-2-yl)-2-hydroxypropyl]-6-[3-(dimethylamino)prop-1-ynyl]-3,4-dihydroisoquinolin-1-one |
| 142 | 2-[(2R)-3-(3,4-dihydro-1H-isoquinolin-2-yl)-2-hydroxy-propyl]-6-[[1-(2-methoxyethyl)-4-piperidyl]oxy]-3,4-dihydroisoquinolin-1-one |
| 143 | 6-[(2R)-3-(3,4-dihydro-1H-isoquinolin-2-yl)-2-hydroxypropyl]-2-[[1-(2-methoxyethyl)-4-piperidyl]oxy]-7,8-dihydro-1,6-naphthyridin-5-one |
| 144 | 6-[(2R)-3-(3,4-dihydro-1H-isoquinolin-2-yl)-2-hydroxypropyl]-2-[[1-[(2R)-2-hydroxypropyl]-4-piperidyl]oxy]-7,8-dihydro-1,6-naphthyridin-5-one |
| 145 | 6-[(2R)-3-(3,4-dihydro-1H-isoquinolin-2-yl)-2-hydroxypropyl]-2-[[1-(2-hydroxy-2-methyl-propyl)-4-piperidyl]oxy]-7,8-dihydro-1,6-naphthyridin-5-one |
| 146 | 6-[(2R)-3-(3,4-dihydro-1H-isoquinolin-2-yl)-2-hydroxypropyl]-2-[[1-(oxetan-3-yl)-4-piperidyl]oxy]-7,8-dihydro-1,6-naphthyridin-5-one |

Since the compounds according to the present invention may have an asymmetric carbon center and an asymmetric axis or an asymmetric plane, they may exist as substantially pure enantiomers, such as R and S enantiomers, as well as all optical and stereoisomeric forms including mixture racemates, and all isomers and compounds thereof are within the scope of the present invention. With respect to a pure enantiomer, the enantiomeric excess of such enantiomer and pharmaceutically acceptable salt thereof represented by Formula 1 may be preferably 60% ee or more, more preferably 95% ee ore more, and most preferably 98% ee or more.

The term "ee" refers to an enantiomeric excess. For example, one enantiomer in a particular compound is present as a mixture of enantiomers in the compound in a larger amount than the other enantiomers. Enantiomerically enriched forms may include enantiomeric compounds of a particular compound in which a single enantiomeric concentration in the enantiomeric mixture of the particular compound is at least 50%, more typically at least 60%, 70%, 80%, or 90%, or more (e.g., >95%, >97%, >98%, >99%, >99.5%) with respect to other enantiomers of the compound.

Herein, unless stated otherwise, the compound represented by Formula 1 is used as a meaning including all of compound represented by Formula 1, an optical isomer, a stereoisomer, an isotopic variant thereof, and a pharmaceutically acceptable salt thereof.

Herein the term "isotopic variant" refers to a compound that contains unnatural proportions of isotopes at one or more of the atoms that constitute such compound. For example, an isotopic variant of a compound may be radiolabeled; hydrogen atom may be selected from hydrogen, deuterium and tritium; and may contain carbon-13 ($^{13}$C), nitrogen-15 ($^{15}$N) or the like.

The compound of Formula 1, or an optical isomer, a stereoisomer or an isotopic variant thereof according to the present invention may form a pharmaceutically acceptable salt. The pharmaceutically acceptable salts include acid or base addition salts and their stereochemical isomers form. The salt may include any salt that maintains the activity of a parent compound in a subject to be administered and does not cause any undesirable effect, but is not limited thereto. The salts include inorganic salts and organic salts, and may be acid addition salts—for example, acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, ethanesulfonic acid, lactic acid, bicarbonic acid, bisulfuric acid, bitartaric acid, oxalic acid, butylic acid, calcium edatate, camsylic acid, carbonic acid, chlorobenzoic acid, citric acid, edetic acid, toluenesulfonic acid, edicylinic acid, ecylinic acid, fumaric acid, gluceptic acid, pamoic acid, gluconic acid, glycollarsanylic acid, methyl nitrate, polygalacturonic acid, hexyllisorcynonic acid, malonic acid, hydrabamic acid, hydrochlorinic acid, hydroiodic acid, hydroxynaphtholic acid, isethionic acid, lactobionic acid, mandelic acid, estolinic acid, mucic acid, naphthenic acid, muconic acid, p-nitromethanesulfonic acid, hexamic acid, pantothenic acid, monohydrogen phosphoric acid, dihydrogen phosphoric acid, salicylic acid, sulfamine acid, sulfanilic acid, methanesulfonic acid or theoclic acid. In addition, examples of basic salts include alkali and alkaline earth metal salts such as ammonium salts, lithium salts, sodium salts, potassium salts, magnesium salts, and calcium salts, salts having organic bases such as benzathine, N-methyl-D-glucamine, and hydrabamine salts, and salts having amino acids such as arginine and lysine. In addition, the salt form may be converted into a free form by treatment with an appropriate base or acid. As used herein, the term "additional salt" may be taken to include solvates obtainable from any of the compound represented by Formula 1 and salts thereof. Examples of these solvates are hydrates or alcoholates.

Terms and abbreviations used in the present specification have their original meanings unless stated otherwise.

The present invention also provides a method for preparing a compound of Formula 1. Hereinafter, a method of preparing the compound of Formula 1 will be described based on an exemplary reaction scheme for better understanding of the present invention. However, it should be construed that those of ordinary skill in the art may prepare the compound of Formula 1 by various methods using known compounds based on the structure of Formula 1 or compounds that may be easily prepared therefrom, and be construed that all the methods may be included in the scope of the present invention. That is, the compound of Formula 1 may be prepared by arbitrarily combining several synthesis methods described in the present specification or disclosed in the prior art, and thus the following description related to the method of preparing the compound of Formula 1 is merely illustrative, and if necessary, the order of unit operations may be selectively changed, and the scope of the method of preparing the present invention is not limited thereto.

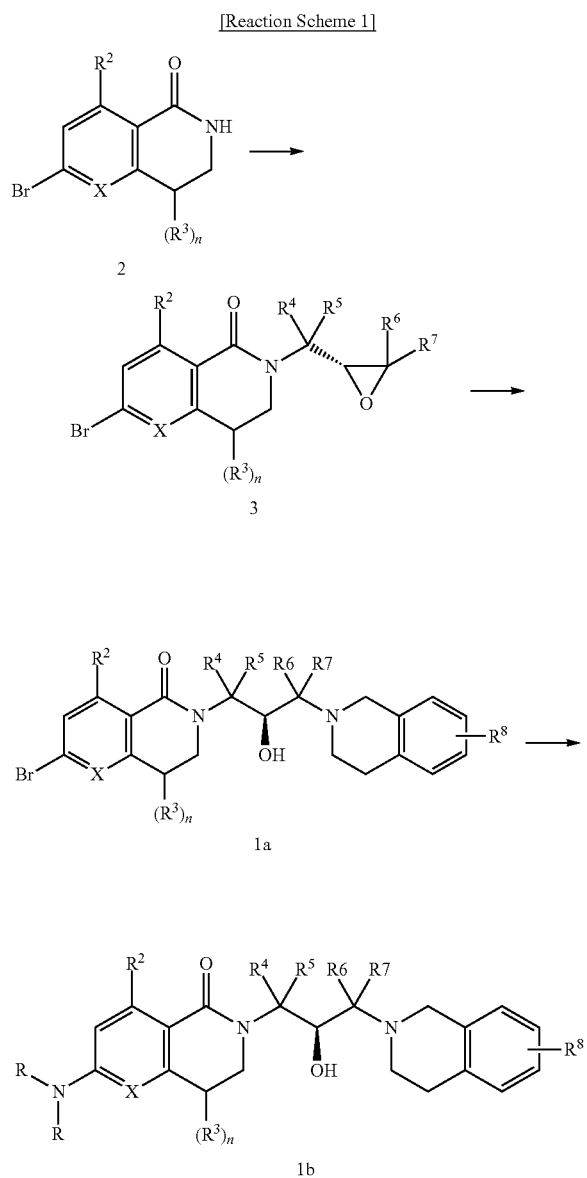

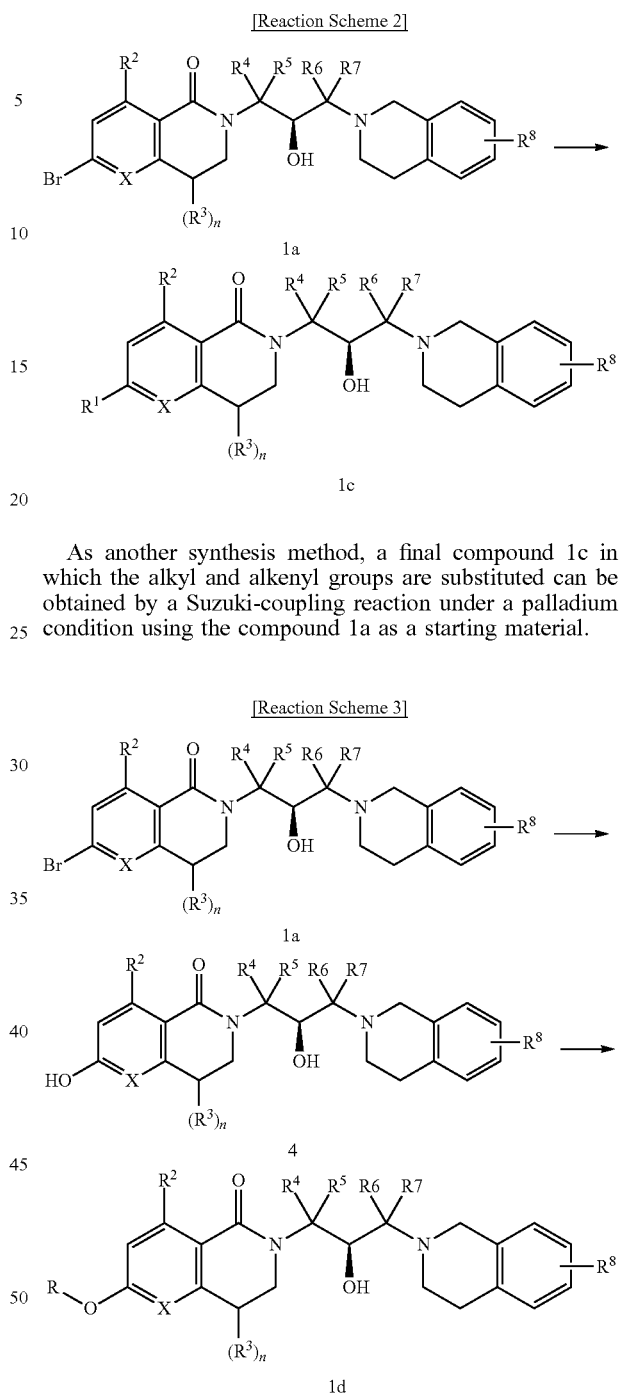

In a general synthesis method, an intermediate 3 in which oxirane is introduced is obtained through a substitution reaction from the starting material 2, and a compound 1a can be obtained through addition of tetrahydroisoquinoline. Additionally, by using the compound 1a as an intermediate, a final compound 1b in which the amine group is substituted can be obtained by a Buchwald-Hartwig amination reaction under a palladium condition.

As another synthesis method, a final compound 1c in which the alkyl and alkenyl groups are substituted can be obtained by a Suzuki-coupling reaction under a palladium condition using the compound 1a as a starting material.

As still another synthesis method, an intermediate 4 in which the bromine group is substituted with a hydroxyl group can be obtained by using potassium hydroxide under a palladium condition and the compound 1a as a starting material, and then a final compound 1d in which the ether group is substituted through a substitution reaction can be obtained.

According to another aspect of the present invention, there is provided a pharmaceutical composition for the prevention or treatment of a disease associated with PRMT5 inhibition comprising a therapeutically effective amount of the compound, or optical isomer, stereoisomer or isotopic variant thereof, or pharmaceutically acceptable salt thereof as an active ingredient, together with a pharmaceutically acceptable carrier. In addition, prodrugs having various forms that are converted to a compound of Formula 1 as desired in vivo are also within the scope of the present invention. The pharmaceutical composition may further include one or more additives selected from the group consisting of a pharmaceutically acceptable carrier, diluent and adjuvant.

As used herein, the term "treatment" refers to the interruption, delay or alleviation of disease progression when used in a subject having a symptom.

As used herein, the term "prevention" refers to reduce the possibility of disease or eliminate the possibility of disease.

As used herein, the term "pharmaceutical composition" may include other chemical components, such as carriers, diluents, excipients, and the like in addition to the active compounds according to the present invention. Accordingly, the pharmaceutical composition may include a pharmaceutically acceptable carrier, diluent, excipient, or a combination thereof, if necessary. The pharmaceutical composition facilitates administration of the active compound into the organism. A variety of techniques for administering pharmaceutical compositions comprising a compound are known, in which the techniques include oral, injection, aerosol, parenteral, and topical administration, but not limited thereto. In addition, the pharmaceutical composition may be sterilized, may further include an adjuvant such as a preservative, a stabilizer, a hydrating or an emulsifying accelerator, a salt for osmotic pressure regulation, and/or a buffer, may further include other therapeutically useful substances, and may be formulated according to conventional methods of mixing, granulating or coating.

As used herein, the term "carrier" refers to a compound that facilitates injection of a compound into a cell or tissue. For example, dimethylsulfoxide (DMSO) is a common carrier for easy input of a large amount of organic compounds into cells or tissues of an organism.

As used herein, the term "diluent" refers to a compound that stabilizes the biologically active form of the compound of interest, and is diluted in water that dissolves the compound. The salt dissolved in the buffer is used as a diluent in the art. A commonly used buffer is phosphate-buffered saline that imitates the salt form of a human body solution. Since the buffer salt is capable of controlling the pH of the solution at low concentrations, the buffer diluent rarely modifies the biological activity of the compound.

As used herein, the term "pharmaceutically acceptable" refers to a property that does not damage biological activity and physical properties of a compound.

In addition, the pharmaceutical composition may be a composition for the prevention and/or treatment of diseases associated with PRMT5 inhibition. The diseases associated with the PRMT5 inhibition may be, for example, cancer, blood disease, autoimmune disease, inflammatory disease or neurodegenerative disease, and may include any disease known to be related to PRMT5.

The cancer includes, but is not limited to, acoustic neuroma, adenocarcinoma, adrenal cancer, anal cancer, angiosarcoma, benign monoclonal gammaglobulinopathy, cholangiocarcinoma, bladder cancer, breast cancer, brain cancer, lymphoma, multiple myeloma, lacrimal gland tumor, bronchial cancer, cervical cancer, craniopharyngioma, colorectal cancer, epithelial carcinoma, epithelial cell tumor, endothelial sarcoma, endometrial cancer, esophageal cancer, Barrett's adenocarcinoma, Ewing's sarcoma, eye cancer, gallbladder cancer, gastric cancer, gastrointestinal stromal tumor (GIST), head and neck cancer, oral cancer (oral squamous cell carcinoma, OSCC), throat cancer, hematopoietic cancer, hemangioblastoma, inflammatory myofibroblast tumor, immune cell amyloidosis, kidney cancer, liver cancer, lung cancer, myelodysplastic syndrome (MDS), mesothelioma, myeloproliferative disorder (MPD), chronic idiopathic myelofibrosis, chronic myelogenous leukemia (CML), chronic neutrophilic leukemia (CNL), neuroblastoma, neurofibroma, neuroendocrine cancer, osteosarcoma, ovarian cancer, papillary adenocarcinoma, pancreatic cancer, penile cancer, prostate cancer, rectal cancer, rhabdomyosarcoma, salivary gland cancer, skin cancer, small intestine cancer, soft tissue sarcoma, thyroid cancer, urethral cancer, vaginal cancer and vulvar cancer. The brain cancer may include, but is not limited to, meningioma, glioma, medulloblastoma, glioblastoma and brain metastasis cancer.

The blood disease may be hemoglobinemia or sickle cell anemia, but is not limited thereto.

The autoimmune disease may include, but is not limited to, rheumatoid arthritis, spinal arthritis, gouty arthritis, degenerative joint disease, osteoarthritis, systemic lupus erythematosus, multiple sclerosis, psoriatic arthritis, juvenile arthritis, asthma, atherosclerosis, osteoporosis, bronchitis, tendinitis, psoriasis, eczema, burns, dermatitis, pruritus, enuresis, eosinophilic disease, peptic ulcer, localized enteritis, diverticulitis, gastrointestinal bleeding, eosinophilic esophagitis, eosinophilic gastritis, eosinophilic gastroenteritis and eosinophilic colitis.

The inflammatory disease may include, but is not limited to, acne-related inflammation, aplastic anemia, hemolytic autoimmune anemia, rhinitis, asthma, polyarteritis, temporal arteritis, periarteritis nodosa, Takayasu's arteritis, crystalline arthritis, osteoarthritis, psoriatic arthritis, gouty arthritis, reactive arthritis, rheumatoid arthritis, amyotrophic lateral sclerosis, autoimmune disease, allergic or allergic reaction, atherosclerosis, bronchitis, bursitis, chronic prostatitis, conjunctivitis, chronic obstructive pulmonary disease, dermatitis, type 1 diabetes, type 2 diabetes, psoriasis, eczema, eczema hypersensitivity reaction, burn, dermatitis, pruritus, endometriosis, infection, ischemic heart disease, glomerulonephritis, gingivitis, irritability, migraine, tension headache, postoperative intestinal obstruction, intestinal obstruction during sepsis, idiopathic thrombocytopenia purpura, bladder pain syndrome, peptic ulcer, localized enteritis, diverticulitis, gastric bleeding, eosinophilic esophagitis, eosinophilic gastritis, eosinophilic gastroenteritis, eosinophilic colitis, gastritis, diarrhea, gastroesophageal reflux disease, Crohn's disease, ulcerative colitis, collagenous colitis, lymphocytic colitis, ischemic colitis, bypass colitis, Behcet's syndrome, indeterminate colitis, inflammatory bowel syndrome (IBS), lupus, ecchymosis, myasthenia gravis and myocardial ischemia.

The neurodegenerative disease may include, but is not limited to, motor neuron disease, Pick's disease, Alzheimer's disease, AIDS-related dementia, Parkinson's disease, amyotrophic lateral sclerosis, retinal pigmentation, spinal muscular atrophy and cerebellar degeneration.

The pharmaceutical composition may be formulated in various oral or parenteral dosage forms. For example, the pharmaceutical composition may be formulated into any dosage form for oral administration, such as tablets, pills, hard/soft capsules, solutions, suspensions, emulsifiers, syrups, granules or elixirs. The formulation for oral administration may include, for example, a pharmaceutically acceptable carrier, such as a diluent, such as lactose, dextrose, sucrose, mannitol, sorbitol, cellulose, and/or glycine, or a lubricant, such as silica, talc, stearic acid, magnesium or calcium salt thereof, and/or polyethylene glycol, in addition to the active ingredient, according to the typical configuration of each formulation.

In addition, when the formulation for oral administration is a tablet, the formulation may include a binder such as magnesium aluminum silicate, starch paste, gelatin, tragacanth, methylcellulose, sodium carboxymethyl cellulose, and/or polyvinylpyrrolidine, and optionally, may include a disintegrant such as starch, agar, alginic acid or a sodium salt thereof, a boiling mixture, and/or an absorbent, a colorant, a flavoring agent, or a sweetening agent.

When the pharmaceutical composition is formulated into a parenteral dosage form, the pharmaceutical composition may be administered by a parenteral administration method such as subcutaneous injection, intravenous injection, intramuscular injection or intrathoracic injection. The pharmaceutical composition may be prepared as a solution or a suspension by mixing an active ingredient—i.e., a compound of Formula 1, or an optical isomer, a stereoisomer or an isotopic variant thereof, or a pharmaceutically acceptable salt thereof, with a stabilizer or a buffer in water, and the solution or the suspension may be prepared as a unit dosage form of an ampoule or a vial.

In addition, the pharmaceutical composition may be sterilized or further include adjuvants such as preservatives, stabilizers, hydrating agents or emulsification accelerators, salts and/or buffers for controlling osmotic pressure, or other therapeutically useful agents, and may be formulated according to a conventional method of mixing, granulating or coating.

The active ingredient—i.e., a compound of Formula 1, or an optical isomer, a stereoisomer or an isotopic variant thereof, or a pharmaceutically acceptable salt thereof may be included in the pharmaceutical composition in an effective amount of 0.1 to 500 mg/kg (body weight), preferably 0.5 to 100 mg/kg (body weight) per day, with respect to mammals including humans, and the pharmaceutical composition may be divided once or twice a day and administered via an oral or parenteral route.

Advantageous Effects of Invention

According to the present invention, there are provided compounds based on a 6-6 bicyclic ring which exhibit excellent PRMT5 inhibitory effect, or optical isomers, stereoisomers or isotopic variants thereof, or pharmaceutically acceptable salts thereof. Therefore, such compounds, or optical isomers, stereoisomers or isotopic variants thereof, or pharmaceutically acceptable salts thereof, can be effectively used to prevent or treat diseases associated with PRMT5 inhibition such as cancer, blood diseases, autoimmune diseases, inflammatory diseases or neurodegenerative diseases.

In addition, the compounds according to the present invention, or optical isomers, stereoisomers or isotopic variants thereof, or pharmaceutically acceptable salts thereof, may have improved blood-brain barrier permeability, superior efficacy or improved pharmacokinetic properties.

DETAILED DESCRIPTION

Hereinafter, the present invention is explained in more detail with the following examples. However, it must be understood that the protection scope of the present disclosure is not limited to the examples.

The abbreviations and terms used in the following Examples are as follows:
BINAP: 2,2'-bis(diphenylphosphino)-1,1'-binaphthyl
$Cs_2CO_3$: cesium carbonate
$NaBH_3CN$: sodium cyanoborohydride
NaOt-Bu: sodium tert-butoxide
$Pd(dppf)Cl_2$: 1,1'-bis(diphenylphosphino)ferrocene-palladium(II) dichloride
$Pd(dba)_2$: bis(dibenzylideneacetone)palladium(0)
$Pd_2(dba)_3$: tris(dibenzylideneacetone)dipalladium(0)
tBuXphos: 2-di-tert-butylphosphino-2',4',6'-trisisopropylbiphenyl
Xantphos: 4,5-bis(diphenylphosphino)-9,9-dimethylxanthene
Xphos: 2-dicyclohexylphosphino-2',4',6'-trisisopropylbiphenyl Example 1: Synthesis of 6-bromo-2-[(2R)-3-(3,4-dihydro-1H-isoquinolin-2-yl)-2-hydroxy-propyl]-3,4-dihydroisoquinolin-1-one

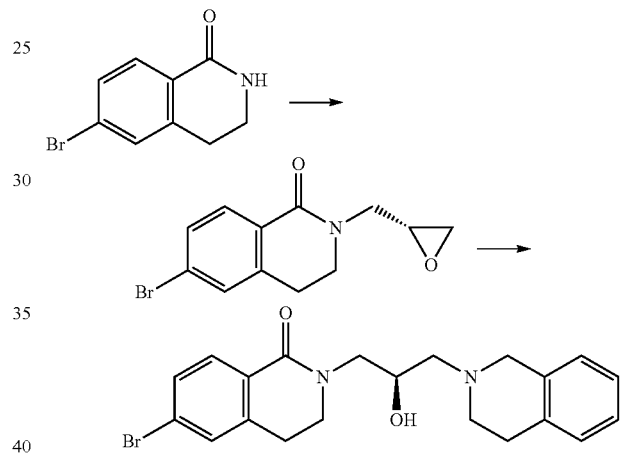

Example 1-1: Synthesis of 6-bromo-2-[[(2R)-oxiran-2-yl]methyl]-3,4-dihydroisoquinolin-1-one 6-Bromo-3,4-dihydro-2H-isoquinolin-1-one (3.6 g, 15.92 mmol) was dissolved in dimethylformamide, and 60% sodium hydride (828 mg, 20.7 mmol) was added at 0° C. and stirred for 30 minutes. (R)-(−)-glycidyl nosylate (4.95 g, 19.11 mmol) was slowly added to the reaction solution, followed by stirring at room temperature. Methanol was added to the reaction mixture to terminate the reaction, and ethyl acetate was added. The reaction mixture was washed with a saturated aqueous ammonium chloride solution and a saturated aqueous sodium chloride solution, and the organic layer was dried over anhydrous magnesium sulfate. The solvent was removed by evaporation under reduced pressure, and 2 g of the title compound was obtained by flash chromatography.

Example 1-2: Synthesis of 6-bromo-2-[(2R)-3-(3,4-dihydro-1H-isoquinolin-2-yl)-2-hydroxy-propyl]-3,4-dihydroisoquinolin-1-one 6-Bromo-2-[[(2R)-oxiran-2-yl]methyl]-3,4-dihydroisoquinolin-1-one (2 g, 7.09 mmol) was dissolved in 53 mL of isopropanol, and tetrahydrogen isoquinoline (0.89 mL, 7.09 mmol) was added dropwise, followed by stirring at 80° C. After completion of the reaction, the solvent was dried under reduced pressure and purified by flash chromatography to obtain 2.2 g of the title compound.

$^1$H NMR (400 MHz, Methanol-d$_4$) δ 7.84 (d, J=8.2 Hz, 1H), 7.57-7.49 (m, 2H), 7.17-7.01 (m, 4H), 4.29-4.20 (m, 1H), 3.91 (dd, J=13.7, 4.0 Hz, 1H), 3.84-3.67 (m, 4H), 3.39 (dd, J=13.6, 7.7 Hz, 1H), 3.04 (t, J=6.8 Hz, 2H), 2.97-2.85 (m, 4H), 2.71-2.59 (m, 2H).

Example 2: Synthesis of 2-[(2R)-3-(3,4-dihydro-1H-isoquinolin-2-yl)-2-hydroxy-propyl]-6-pyrrolidin-1-yl-3,4-dihydroisoquinolin-1-one

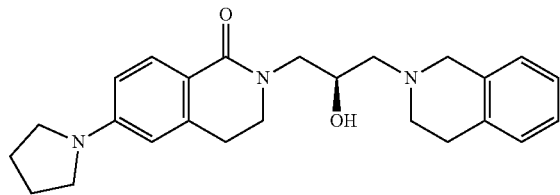 [SMILES: O=C1c2ccc(N3CCCC3)cc2CCN1C[C@H](O)CN1CCc2ccccc2C1]

6-Bromo-2-[(2R)-3-(3,4-dihydro-1H-isoquinolin-2-yl)-2-hydroxy-propyl]-3,4-dihydroisoquinolin-1-one (100 mg, 0.24 mmol) obtained in Example 1, pyrrolidine (0.12 mL, 0.96 mmol), Pd$_2$(dba)$_3$ (11 mg, 0.01 mmol), NaOt-Bu (35 mg, 0.03 mmol) and BINAP (15 mg, 0.02 mmol) were dissolved in 4 mL of toluene and stirred in a microwave at 120° C. for 2 hours. The reaction mixture was diluted with ethyl acetate and filtered through Celite. The solvent was dried under reduced pressure and purified by flash chromatography to obtain 40 mg of the title compound.

$^1$H NMR (400 MHz, Methanol-d$_4$) δ 7.76 (d, J=8.7 Hz, 1H), 7.18-7.01 (m, 4H), 6.51 (d, J=8.8 Hz, 1H), 6.36 (s, 1H), 4.28-4.18 (m, 1H), 3.87 (dd, J=14.0, 4.3 Hz, 1H), 3.84-3.61 (m, 4H), 3.36 (d, J=6.0 Hz, 4H), 2.97-2.91 (m, 6H), 2.76-2.61 (m, 2H), 2.14-2.00 (m, 4H).

Example 3: Synthesis of 6-(cyclohexylamino)-2-[(2R)-3-(3,4-dihydro-1H-isoquinolin-2-yl)-2-hydroxy-propyl]-3,4-dihydroisoquinolin-1-one

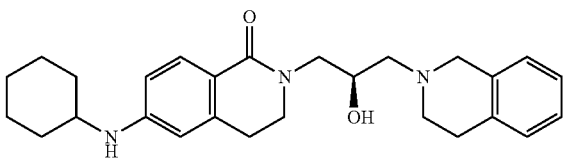 [SMILES: O=C1c2ccc(NC3CCCCC3)cc2CCN1C[C@H](O)CN1CCc2ccccc2C1]

The title compound was synthesized in the same manner as in Example 2, except that cyclohexanamine was used instead of pyrrolidine.

$^1$H NMR (400 MHz, Chloroform-d) δ 7.92 (d, J=8.3 Hz, 1H), 7.53-7.40 (m, 1H), 7.36 (d, J=1.9 Hz, 1H), 7.12 (qd, J=8.4, 7.3, 4.0 Hz, 3H), 7.05-6.91 (m, 1H), 4.12 (ddt, J=10.1, 7.0, 3.5 Hz, 1H), 3.96-3.68 (m, 5H), 3.62 (d, J=14.9 Hz, 2H), 3.45 (ddd, J=20.6, 13.8, 6.6 Hz, 2H), 3.04-2.78 (m, 6H), 2.77-2.58 (m, 2H), 2.53 (dd, J=12.3, 10.1 Hz, 2H), 1.35-1.10 (m, 4H), 0.99-0.71 (m, 2H).

Example 4: Synthesis of 2-[(2R)-3-(3,4-dihydro-1H-isoquinolin-2-yl)-2-hydroxy-propyl]-6-morpholino-3,4-dihydroisoquinoline-1-one

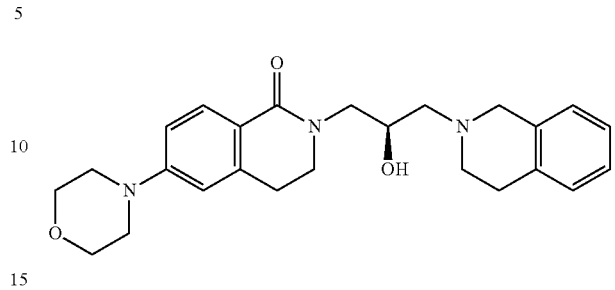

The title compound was synthesized in the same manner as in Example 2, except that morpholine was used instead of pyrrolidine.

$^1$H NMR (400 MHz, Methanol-d$_4$) δ 7.82 (d, J=8.8 Hz, 1H), 7.17-7.07 (m, 3H), 7.05 (d, J=7.0 Hz, 1H), 6.91 (dd, J=8.7, 2.5 Hz, 1H), 6.78 (d, J=2.5 Hz, 1H), 4.23 (td, J=7.3, 3.8 Hz, 1H), 3.93-3.81 (m, 5H), 3.79-3.64 (m, 4H), 3.40-3.34 (m, 1H), 3.29 (t, J=4.9 Hz, 4H), 3.03-2.96 (m, 2H), 2.92 (d, J=5.5 Hz, 2H), 2.87 (t, J=5.5 Hz, 2H), 2.69-2.58 (m, 2H).

Example 5: Synthesis of 2-[(2R)-3-(3,4-dihydro-1H-isoquinolin-2-yl)-2-hydroxy-propyl]-6-(tetrahydropyran-4-ylamino)-3,4-dihydroisoquinolin-1-one

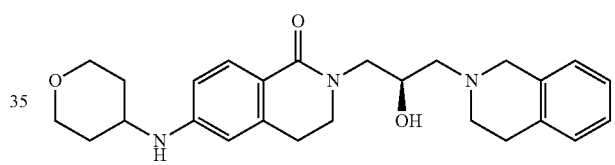

The title compound was synthesized in the same manner as in Example 2, except that tetrahydropyran-4-amine was used instead of pyrrolidine.

$^1$H NMR (400 MHz, Chloroform-d) δ 7.88 (d, J=8.5 Hz, 1H), 7.23-7.04 (m, 3H), 7.06-6.93 (m, 1H), 6.51 (dd, J=8.6, 2.4 Hz, 1H), 6.31 (d, J=2.3 Hz, 1H), 4.17-3.39 (m, 14H), 2.80-2.48 (m, 4H), 2.04 (d, J=12.7 Hz, 3H), 1.51 (td, J=14.4, 7.4 Hz, 3H).

Example 6: Synthesis of 6-(cyclohexylmethylamino)-2-[(2R)-3-(3,4-dihydro-1H-isoquinolin-2-yl)-2-hydroxy-propyl]-3,4-dihydroisoquinolin-1-one

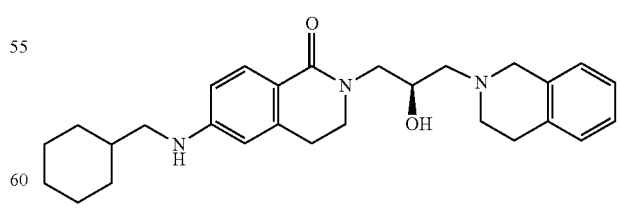

The title compound was synthesized in the same manner as in Example 2, except that cyclohexylmethanamine was used instead of pyrrolidine.

$^1$H NMR (400 MHz, Chloroform-d) δ 7.86 (d, J=8.5 Hz, 1H), 7.12 (qd, J=8.5, 7.2, 3.9 Hz, 3H), 7.07-6.94 (m, 1H), 6.49 (dd, J=8.6, 2.4 Hz, 1H), 6.28 (d, J=2.4 Hz, 1H), 4.10 (d, J=7.7 Hz, 2H), 3.93-3.57 (m, 5H), 3.48 (dd, J=13.9, 6.0 Hz, 1H), 2.99 (t, J=6.1 Hz, 2H), 2.90 (d, J=6.4 Hz, 4H), 2.78-2.48 (m, 3H), 1.91-1.49 (m, 7H), 1.40-1.12 (m, 3H), 0.98 (q, J=11.8 Hz, 2H).

Example 7: Synthesis of 6-(benzylamino)-2-[(2R)-3-(3,4-dihydro-1H-isoquinolin-2-yl)-2-hydroxy-propyl]-3,4-dihydroisoquinolin-1-one

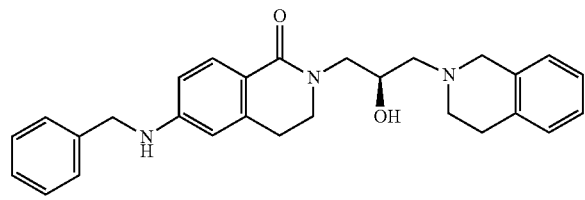 [SMILES: O=C1c2ccc(NCc3ccccc3)cc2CCN1C[C@H](O)CN1CCc2ccccc2C1]

The title compound was synthesized in the same manner as in Example 2, except that phenylmethanamine was used instead of pyrrolidine.

$^1$H NMR (400 MHz, Chloroform-d) δ 7.88 (d, J=8.4 Hz, 1H), 7.41-7.20 (m, 5H), 7.12 (qd, J=8.6, 7.3, 4.0 Hz, 3H), 7.04-6.93 (m, 1H), 6.55 (dd, J=8.6, 2.4 Hz, 1H), 6.34 (d, J=2.3 Hz, 1H), 4.44 (s, 1H), 4.37 (s, 2H), 4.11 (dt, J=10.7, 4.3 Hz, 1H), 3.90-3.74 (m, 2H), 3.66 (qd, J=14.7, 13.7, 6.6 Hz, 3H), 3.46 (dd, J=14.0, 6.0 Hz, 1H), 2.88 (q, J=7.7, 6.4 Hz, 5H), 2.77-2.47 (m, 3H).

Example 8: Synthesis of 2-[(2R)-3-(3,4-dihydro-1H-isoquinolin-2-yl)-2-hydroxy-propyl]-6-(4-pyridyl)-3,4-dihydroisoquinolin-1-one

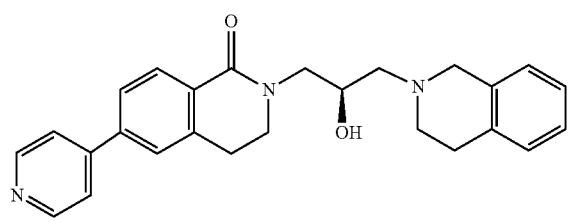 [SMILES: O=C1c2ccc(-c3ccncc3)cc2CCN1C[C@H](O)CN1CCc2ccccc2C1]

6-Bromo-2-[(2R)-3-(3,4-dihydro-1H-isoquinolin-2-yl)-2-hydroxy-propyl]-3,4-dihydroisoquinolin-1-one (100 mg, 0.24 mmol) obtained in Example 1, 4-pyridylboronic acid (60 mg, 0.48 mmol), Pd((dppf)Cl$_2$ (20 mg, 0.02 mmol) and K$_2$CO$_3$ (100 mg, 0.72 mmol) were dissolved in 3 mL of 1,4-dioxane and 1 mL of H$_2$O, followed by stirring in a microwave at 120° C. for 2 hours. The reaction mixture was diluted with ethyl acetate and filtered through Celite. The solvent was dried under reduced pressure, and the purification was carried out by flash chromatography to obtain 35 mg of the title compound.

$^1$H NMR (400 MHz, Chloroform-d) δ 8.69 (d, J=5.1 Hz, 2H), 8.18 (d, J=8.1 Hz, 1H), 7.67-7.42 (m, 4H), 7.13 (dp, J=8.9, 6.4, 4.3 Hz, 3H), 7.05-6.94 (m, 1H), 4.16 (ddt, J=10.2, 7.0, 3.6 Hz, 1H), 4.02-3.71 (m, 4H), 3.64 (d, J=14.6 Hz, 1H), 3.48 (dd, J=13.9, 6.3 Hz, 1H), 3.09 (t, J=6.7 Hz, 2H), 2.93 (tt, J=10.7, 4.8 Hz, 3H), 2.82-2.49 (m, 3H).

Example 9: Synthesis of 2-[(2R)-3-(3,4-dihydro-1H-isoquinolin-2-yl)-2-hydroxy-propyl]-6-(3-pyridyl)-3,4-dihydroisoquinolin-1-one

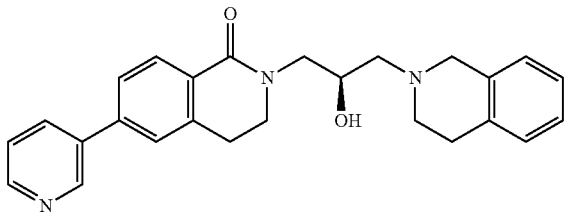 [SMILES: O=C1c2ccc(-c3cccnc3)cc2CCN1C[C@H](O)CN1CCc2ccccc2C1]

The title compound was synthesized in the same manner as in Example 8, except that 3-pyridylboronic acid was used instead of 4-pyridylboronic acid.

$^1$H NMR (400 MHz, Chloroform-d) δ 8.87 (d, J=2.4 Hz, 1H), 8.63 (dd, J=4.8, 1.7 Hz, 1H), 8.18 (d, J=8.1 Hz, 1H), 7.91 (dt, J=8.1, 2.1 Hz, 1H), 7.56 (dd, J=8.0, 1.9 Hz, 1H), 7.47-7.33 (m, 2H), 7.21-7.06 (m, 3H), 7.06-6.91 (m, 1H), 4.16 (dtt, J=14.3, 10.7, 5.4 Hz, 1H), 3.93 (dd, J=14.0, 3.1 Hz, 1H), 3.88-3.73 (m, 3H), 3.68-3.57 (m, 1H), 3.49 (dd, J=14.0, 6.2 Hz, 1H), 3.10 (q, J=8.0, 6.6 Hz, 2H), 2.93 (tt, J=10.3, 4.7 Hz, 3H), 2.80-2.53 (m, 3H).

Example 10: Synthesis of 2-[(2R)-3-(3,4-dihydro-1H-isoquinolin-2-yl)-2-hydroxy-propyl]-6-(4-pyridylmethylamino)-3,4-dihydroisoquinolin-1-one

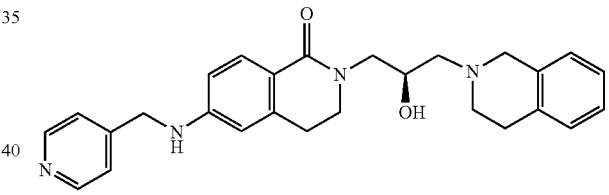

The title compound was synthesized in the same manner as in Example 2, except that 4-pyridylmethanamine was used instead of pyrrolidine.

$^1$H NMR (400 MHz, Methanol-d$_4$) δ 8.46 (d, J=5.9 Hz, 2H), 7.69 (d, J=8.5 Hz, 1H), 7.42 (d, J=5.2 Hz, 2H), 7.15-6.95 (m, 4H), 6.53 (dd, J=8.6, 2.3 Hz, 1H), 6.37 (d, J=2.3 Hz, 1H), 4.20 (tt, J=7.7, 4.6 Hz, 1H), 3.84 (dd, J=13.8, 4.2 Hz, 1H), 3.77-3.51 (m, 4H), 3.33 (d, J=21.3 Hz, 3H), 2.88 (dt, J=25.3, 6.4 Hz, 6H), 2.66-2.54 (m, 2H).

Example 11: Synthesis of 6-[cyclohexyl(methyl)amino]-2-[(2R)-3-(3,4-dihydro-1H-isoquinolin-2-yl)-2-hydroxy-propyl]-3,4-dihydroisoquinolin-1-one

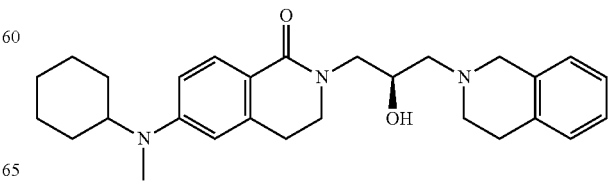

The title compound was synthesized in the same manner as in Example 2, except that N-methylcyclohexanamine was used instead of pyrrolidine.

$^1$H NMR (400 MHz, Methanol-$d_4$) δ 7.76 (d, J=8.8 Hz, 1H), 7.18-6.94 (m, 4H), 6.72 (dd, J=8.9, 2.6 Hz, 1H), 6.56 (d, J=2.6 Hz, 1H), 4.22 (tt, J=7.7, 4.6 Hz, 1H), 3.87 (dd, J=13.7, 4.3 Hz, 1H), 3.79-3.61 (m, 5H), 3.37 (d, J=7.3 Hz, 1H), 3.01-2.87 (m, 5H), 2.71-2.60 (m, 2H), 2.04 (d, J=9.6 Hz, 1H), 1.88 (d, J=12.9 Hz, 2H), 1.81-1.66 (m, 3H), 1.65-1.39 (m, 5H), 1.38-1.17 (m, 3H).

Example 12: Synthesis of 2-[(2R)-3-(3,4-dihydro-1H-isoquinolin-2-yl)-2-hydroxy-propyl]-6-(2-fluoro-4-pyridyl)-3,4-dihydroisoquinolin-1-one

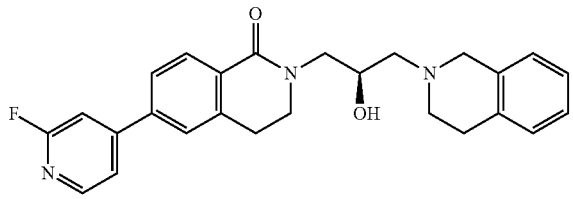 [SMILES: O=C1c2ccc(-c3ccnc(F)c3)cc2CCN1C[C@H](O)CN1CCc2ccccc2C1]

The title compound was synthesized in the same manner as in Example 8, except that (2-fluoro-4-pyridyl)boronic acid was used instead of 4-pyridylboronic acid.

$^1$H NMR (400 MHz, Methanol-$d_4$) δ 8.30 (d, J=5.3 Hz, 1H), 8.09 (d, J=8.1 Hz, 1H), 7.85-7.73 (m, 1H), 7.72 (s, 1H), 7.67 (d, J=5.3 Hz, 1H), 7.45 (s, 1H), 7.17-7.07 (m, 3H), 7.05 (d, J=6.5 Hz, 1H), 4.27 (dd, J=11.1, 5.3 Hz, 1H), 3.95 (dd, J=13.7, 4.1 Hz, 1H), 3.91-3.73 (m, 4H), 3.43 (dd, J=13.7, 7.8 Hz, 1H), 3.21-3.10 (m, 2H), 2.91 (dt, J=9.6, 5.1 Hz, 4H), 2.74-2.61 (m, 2H).

Example 13: Synthesis of 2-[(2R)-3-(3,4-dihydro-1H-isoquinolin-2-yl)-2-hydroxy-propyl]-6-propyl-3,4-dihydroisoquinolin-1-one

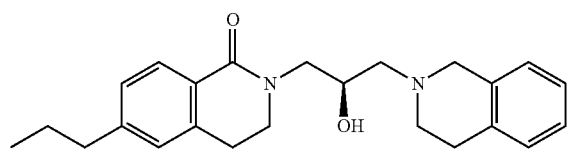 [SMILES: CCCc1ccc2c(c1)CCN(C[C@H](O)CN1CCc3ccccc3C1)C2=O]

The title compound was synthesized in the same manner as in Example 8, except that propylboronic acid was used instead of 4-pyridylboronic acid.

$^1$H NMR (400 MHz, Methanol-$d_4$) δ 7.85 (d, J=7.9 Hz, 1H), 7.22-6.99 (m, 6H), 4.26 (h, J=6.3, 5.5 Hz, 1H), 3.91 (dd, J=13.7, 4.2 Hz, 1H), 3.83-3.66 (m, 4H), 3.39 (dd, J=13.7, 7.7 Hz, 1H), 3.06-2.97 (m, 2H), 2.91 (dd, J=14.3, 4.8 Hz, 4H), 2.71-2.60 (m, 2H), 1.67 (hept, J=7.4 Hz, 2H), 1.30 (q, J=6.8, 6.3 Hz, 2H), 0.97 (t, J=7.4 Hz, 3H).

Example 14: Synthesis of 2-[(2R)-3-(3,4-dihydro-1H-isoquinolin-2-yl)-2-hydroxy-propyl]-6-[(2R,6S)-2,6-dimethylmorpholin-4-yl]-3,4-dihydroisoquinolin-1-one

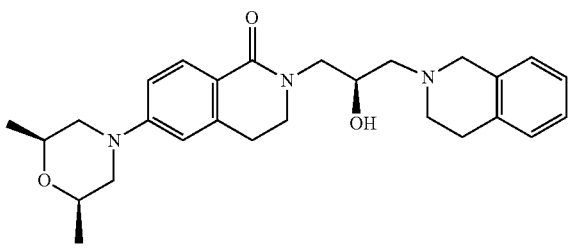 [SMILES: C[C@@H]1CN(c2ccc3c(c2)CCN(C[C@H](O)CN2CCc4ccccc4C2)C3=O)C[C@H](C)O1]

The title compound was synthesized in the same manner as in Example 2, except that (2R,6S)-2,6-dimethylmorpholine was used instead of pyrrolidine.

$^1$H NMR (400 MHz, Methanol-$d_4$) δ 7.81 (d, J=8.7 Hz, 1H), 7.20-6.98 (m, 4H), 6.90 (dd, J=8.8, 2.5 Hz, 1H), 6.77 (d, J=2.5 Hz, 1H), 4.32-4.11 (m, 1H), 3.88 (dd, J=13.8, 4.2 Hz, 1H), 3.80-3.64 (m, 8H), 3.42-3.34 (m, 1H), 3.01-2.83 (m, 6H), 2.72-2.58 (m, 2H), 2.43 (dd, J=12.2, 10.3 Hz, 2H), 1.25 (d, J=6.2 Hz, 6H).

Example 15: Synthesis of 2-[(2R)-3-(3,4-dihydro-1H-isoquinolin-2-yl)-2-hydroxy-propyl]-6-(6-fluoro-3-pyridyl)-3,4-dihydroisoquinolin-1-one

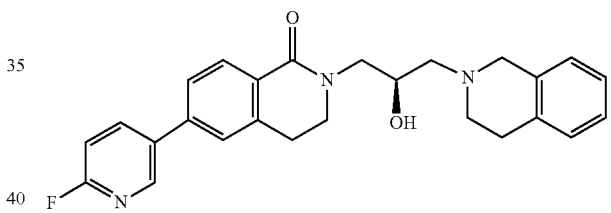

The title compound was synthesized in the same manner as in Example 8, except that (6-fluoro-3-pyridyl)boronic acid was used instead of 4-pyridylboronic acid.

$^1$H NMR (400 MHz, Methanol-$d_4$) δ 8.53 (d, J=2.6 Hz, 1H), 8.27 (td, J=8.1, 2.6 Hz, 1H), 8.06 (d, J=8.1 Hz, 1H), 7.71-7.52 (m, 2H), 7.20 (dd, J=8.6, 2.6 Hz, 1H), 7.14-7.01 (m, 4H), 4.28 (tt, J=8.1, 4.7 Hz, 1H), 3.95 (dd, J=13.7, 4.1 Hz, 1H), 3.90-3.74 (m, 4H), 3.43 (dd, J=13.7, 7.7 Hz, 1H), 3.19-3.07 (m, 2H), 3.00-2.83 (m, 4H), 2.76-2.58 (m, 2H).

Example 16: Synthesis of 2-[(2R)-3-(3,4-dihydro-1H-isoquinolin-2-yl)-2-hydroxy-propyl]-6-[(2R)-2-methylmorpholin-4-yl]-3,4-dihydroisoquinolin-1-one

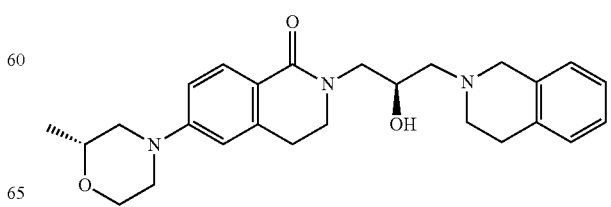

The title compound was synthesized in the same manner as in Example 2, except that (2R)-2-methylmorpholine was used instead of pyrrolidine.

¹H NMR (400 MHz, Methanol-d₄) δ 7.81 (d, J=8.7 Hz, 1H), 7.20-7.00 (m, 4H), 6.91 (d, J=8.4 Hz, 1H), 6.78 (s, 1H), 4.22 (dt, J=8.1, 4.7 Hz, 1H), 4.06-3.94 (m, 1H), 3.88 (dd, J=13.9, 4.2 Hz, 1H), 3.81-3.61 (m, 8H), 3.43-3.35 (m, 1H), 3.06-2.78 (m, 7H), 2.73-2.58 (m, 2H), 2.50 (t, J=11.6 Hz, 1H), 1.25 (d, J=6.3 Hz, 3H).

Example 17: Synthesis of 2-[(2R)-3-(3,4-dihydro-1H-isoquinolin-2-yl)-2-hydroxy-propyl]-6-(4-methylpiperazin-1-yl)-3,4-dihydroisoquinolin-1-one

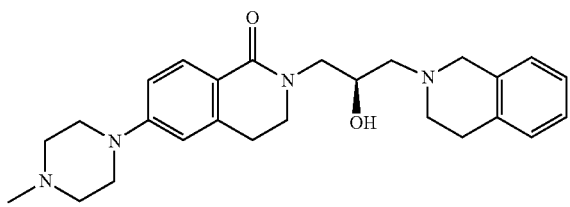 [SMILES: CN1CCN(c2ccc3c(c2)CCN(C[C@H](O)CN2CCc4ccccc4C2)C3=O)CC1]

The title compound was synthesized in the same manner as in Example 2, except that N-methylpiperazine was used instead of pyrrolidine.

¹H NMR (400 MHz, Methanol-d₄) δ 7.81 (d, J=8.8 Hz, 1H), 7.18-7.03 (m, 4H), 6.97-6.85 (m, 1H), 6.79 (s, 1H), 4.34-4.17 (m, 1H), 3.88 (dd, J=13.9, 4.2 Hz, 1H), 3.83-3.66 (m, 4H), 3.58 (t, J=4.8 Hz, 1H), 3.38 (q, J=6.0, 4.6 Hz, 5H), 3.03-2.88 (m, 5H), 2.72-2.65 (m, 2H), 2.63 (t, J=5.1 Hz, 3H), 2.38 (s, 3H).

Example 18: Synthesis of 2-[(2R)-3-(3,4-dihydro-1H-isoquinolin-2-yl)-2-hydroxy-propyl]-6-(2-oxopyrrolidin-1-yl)-3,4-dihydroisoquinolin-1-one

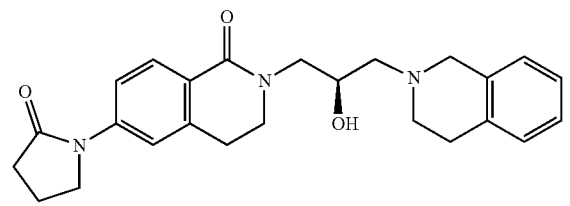 [SMILES: O=C1c2ccc(N3CCCC3=O)cc2CCN1C[C@H](O)CN1CCc2ccccc2C1]

6-Bromo-2-[(2R)-3-(3,4-dihydro-1H-isoquinolin-2-yl)-2-hydroxy-propyl]-3,4-dihydroisoquinolin-1-one (100 mg, 0.24 mmol) obtained in Example 1, pyrrolidin-2-one (74 µL, 0.96 mmol), Pd₂(dba)₃ (11 mg, 0.01 mmol), Cs₂CO₃ (110 mg, 0.34 mmol) and Xantphos (21 mg, 0.036 mmol) were dissolved in 4 mL of 1,4-dioxane and stirred in a microwave at 120° C. for 2 hours. The reaction mixture was diluted with ethyl acetate and filtered through Celite. The solvent was dried under reduced pressure, and the purification was carried out by flash chromatography to obtain 38 mg of the title compound.

¹H NMR (400 MHz, Methanol-d₄) δ 7.95 (d, J=8.6 Hz, 1H), 7.75-7.57 (m, 2H), 7.18-6.97 (m, 4H), 4.24 (q, J=6.4 Hz, 1H), 4.04-3.87 (m, 3H), 3.85-3.66 (m, 5H), 3.58 (t, J=4.7 Hz, 1H), 3.40 (q, J=6.0 Hz, 1H), 3.13-3.01 (m, 2H), 2.90 (dd, J=17.2, 5.2 Hz, 4H), 2.72-2.58 (m, 4H).

Example 19: Synthesis of N-[2-[(2R)-3-(3,4-dihydro-1H-isoquinolin-2-yl)-2-hydroxy-propyl]-1-oxo-3,4-dihydroisoquinolin-6-yl]-2,2-dimethylpropanamide

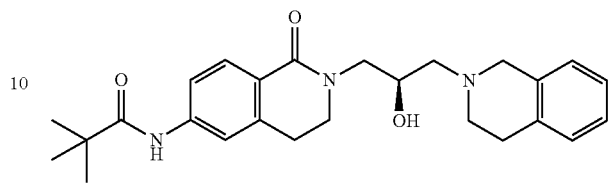

The title compound was synthesized in the same manner as in Example 18, except that 2,2-dimethylpropanamide was used instead of pyrrolidin-2-one.

¹H NMR (400 MHz, Methanol-d₄) δ 7.89 (d, J=8.5 Hz, 1H), 7.63 (s, 1H), 7.52 (d, J=8.5 Hz, 1H), 7.18-7.00 (m, 4H), 4.25 (tt, J=8.2, 4.7 Hz, 1H), 3.90 (dd, J=13.7, 4.1 Hz, 1H), 3.84-3.66 (m, 4H), 3.39 (dd, J=13.8, 7.6 Hz, 1H), 3.09-2.99 (m, 2H), 2.92 (dq, J=10.8, 6.7, 6.0 Hz, 4H), 2.73-2.61 (m, 2H), 1.32 (s, 9H).

Example 20: Synthesis of 2-[(2R)-3-(3,4-dihydro-1H-isoquinolin-2-yl)-2-hydroxy-propyl]-6-(2-oxoazetidin-1-yl)-3,4-dihydroisoquinolin-1-one

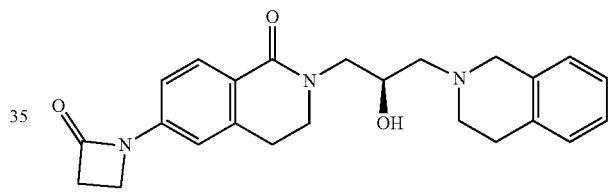

The title compound was synthesized in the same manner as in Example 18, except that azetidin-2-one was used instead of pyrrolidin-2-one.

¹H NMR (400 MHz, Methanol-d₄) δ 7.94 (d, J=8.9 Hz, 1H), 7.32 (d, J=7.0 Hz, 2H), 7.17-6.99 (m, 4H), 4.25 (tt, J=7.6, 4.6 Hz, 1H), 3.90 (dd, J=13.8, 4.1 Hz, 1H), 3.85-3.67 (m, 6H), 3.39 (dd, J=13.8, 7.7 Hz, 1H), 3.15 (t, J=4.6 Hz, 2H), 3.09-2.98 (m, 2H), 2.92 (dp, J=8.7, 4.4, 3.3 Hz, 4H), 2.72-2.59 (m, 2H).

Example 21: Synthesis of 2-[(2R)-3-(3,4-dihydro-1H-isoquinolin-2-yl)-2-hydroxy-propyl]-6-(2-oxo-1-piperidyl)-3,4-dihydroisoquinolin-1-one

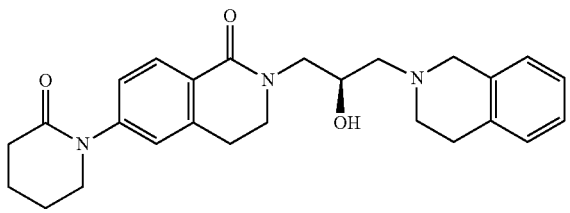 [SMILES: O=C1c2ccc(N3CCCCC3=O)cc2CCN1C[C@H](O)CN1CCc2ccccc2C1]

The title compound was synthesized in the same manner as in Example 18, except that piperidin-2-one was used instead of pyrrolidin-2-one.

$^1$H NMR (400 MHz, Methanol-d$_4$) δ 7.99 (d, J=8.2 Hz, 1H), 7.33-7.17 (m, 2H), 7.20-6.99 (m, 3H), 3.92 (dd, J=13.8, 4.1 Hz, 1H), 3.87-3.66 (m, 5H), 3.58 (t, J=4.7 Hz, 1H), 3.41 (dd, J=13.8, 7.6 Hz, 1H), 3.12-3.01 (m, 2H), 2.93 (d, J=6.4 Hz, 3H), 2.76-2.62 (m, 2H), 2.55 (t, J=6.2 Hz, 2H), 2.07-1.93 (m, 4H), 1.34 (m, 2H).

Example 22: Synthesis of 2-[(2R)-3-(3,4-dihydro-1H-isoquinolin-2-yl)-2-hydroxy-propyl]-6-(3-pyridylmethylamino)-3,4-dihydroisoquinolin-1-one

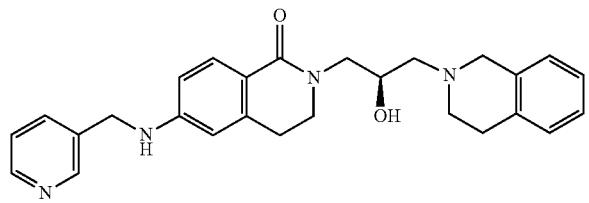 [SMILES: O=C1c2ccc(NCc3cccnc3)cc2CCN1C[C@H](O)CN1CCc2ccccc2C1]

The title compound was synthesized in the same manner as in Example 2, except that 3-pyridylmethanamine was used instead of pyrrolidine.

$^1$H NMR (400 MHz, Methanol-d$_4$) δ 8.56 (d, J=2.2 Hz, 1H), 8.43 (d, J=5.0 Hz, 1H), 7.85 (d, J=8.0 Hz, 1H), 7.70 (d, J=8.6 Hz, 1H), 7.41 (dd, J=7.9, 4.9 Hz, 1H), 7.18-7.00 (m, 4H), 6.57 (dd, J=8.7, 2.3 Hz, 1H), 6.42 (d, J=2.4 Hz, 1H), 4.47 (s, 2H), 4.20 (dq, J=7.8, 4.7, 3.9 Hz, 1H), 3.85 (dd, J=13.8, 4.2 Hz, 1H), 3.76-3.57 (m, 4H), 3.33 (d, J=21.3 Hz, 1H), 2.89 (dq, J=15.4, 6.3 Hz, 6H), 2.68-2.55 (m, 2H).

Example 23: Synthesis of 2-[(2R)-3-(3,4-dihydro-1H-isoquinolin-2-yl)-2-hydroxy-propyl]-6-(tetrahydropyran-4-ylmethylamino)-3,4-dihydroisoquinolin-1-one

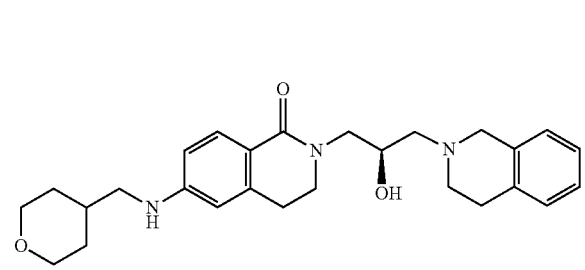 [SMILES: O=C1c2ccc(NCC3CCOCC3)cc2CCN1C[C@H](O)CN1CCc2ccccc2C1]

The title compound was synthesized in the same manner as in Example 2, except that tetrahydropyran-4-ylmethanamine was used instead of pyrrolidine.

$^1$H NMR (400 MHz, Methanol-d$_4$) δ 7.69 (d, J=8.6 Hz, 1H), 7.20-6.96 (m, 4H), 6.54 (dd, J=8.7, 2.3 Hz, 1H), 6.39 (d, J=2.3 Hz, 1H), 4.21 (tt, J=7.7, 4.6 Hz, 1H), 3.97 (dd, J=11.4, 4.6 Hz, 2H), 3.86 (dd, J=13.8, 4.2 Hz, 1H), 3.78-3.59 (m, 4H), 3.49-3.33 (m, 4H), 3.05 (d, J=6.8 Hz, 2H), 2.88 (dt, J=19.7, 6.1 Hz, 6H), 2.69-2.57 (m, 2H), 1.89 (dqt, J=14.8, 10.9, 6.0 Hz, 1H), 1.79-1.68 (m, 1H), 1.33 (qd, J=14.6, 13.4, 5.8 Hz, 2H).

Example 24: Synthesis of 6-[(1-acetyl-4-piperidyl)methylamino]-2-[(2R)-3-(3,4-dihydro-1H-isoquinolin-2-yl)-2-hydroxy-propyl]-3,4-dihydroisoquinolin-1-one

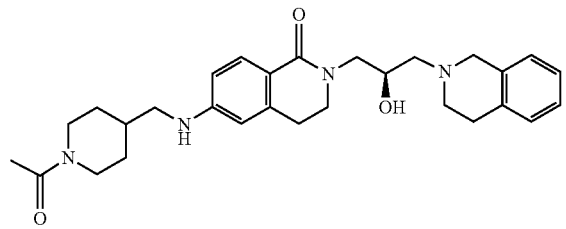 [SMILES: CC(=O)N1CCC(CNc2ccc3c(c2)CCN(C[C@H](O)CN2CCc4ccccc4C2)C3=O)CC1]

The title compound was synthesized in the same manner as in Example 2, except that 1-[4-(aminomethyl)-1-piperidyl]ethanone was used instead of pyrrolidine.

$^1$H NMR (400 MHz, Methanol-d$_4$) δ 7.69 (d, J=8.6 Hz, 1H), 7.17-6.94 (m, 4H), 6.55 (dd, J=8.6, 2.3 Hz, 1H), 6.44-6.30 (m, 1H), 4.55 (d, J=13.2 Hz, 1H), 4.21 (tt, J=7.8, 4.6 Hz, 1H), 3.95 (d, J=13.8 Hz, 1H), 3.86 (dd, J=13.8, 4.2 Hz, 1H), 3.79-3.58 (m, 4H), 3.34 (d, J=21.4 Hz, 1H), 3.09 (dd, J=14.0, 4.3 Hz, 3H), 2.89 (dt, J=15.3, 5.9 Hz, 6H), 2.72-2.55 (m, 3H), 2.11 (s, 3H), 1.88 (dd, J=19.9, 13.8 Hz, 3H), 1.40-1.06 (m, 2H).

Example 25: Synthesis of 2-[(2R)-3-(3,4-dihydro-1H-isoquinolin-2-yl)-2-hydroxy-propyl]-6-[(2-hydroxy-2-methyl-propyl)amino]-3,4-dihydroisoquinolin-1-one

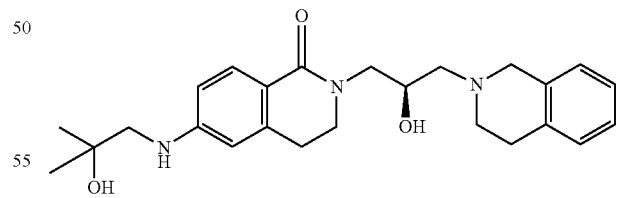

The title compound was synthesized in the same manner as in Example 2, except that 1-amino-2-methyl-propan-2-ol was used instead of pyrrolidine.

$^1$H NMR (400 MHz, Methanol-d$_4$) δ 7.69 (d, J=8.6 Hz, 1H), 7.28-6.96 (m, 4H), 6.60 (dd, J=8.6, 2.3 Hz, 1H), 6.52-6.31 (m, 1H), 4.21 (dq, J=7.9, 4.8, 4.0 Hz, 1H), 3.87 (dd, J=13.8, 4.2 Hz, 1H), 3.80-3.48 (m, 4H), 3.37 (s, 1H), 3.16 (s, 2H), 2.90 (dd, J=17.7, 5.9 Hz, 6H), 2.73-2.55 (m, 2H), 1.27 (s, 6H).

Example 26: Synthesis of N-[2-[(2R)-3-(3,4-dihydro-1H-isoquinolin-2-yl)-2-hydroxy-propyl]-1-oxo-3,4-dihydroisoquinolin-6-yl]pyridine-3-carboxamide

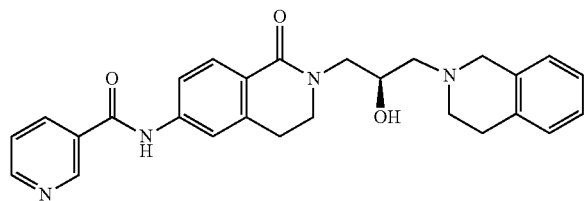 [SMILES: O=C(Nc1ccc2c(c1)CCN(C[C@H](O)CN1CCc3ccccc3C1)C2=O)c1cccnc1]

The title compound was synthesized in the same manner as in Example 18, except that pyridine-3-carboxamide was used instead of pyrrolidin-2-one.

$^1$H NMR (400 MHz, Methanol-$d_4$) δ 9.11 (d, J=2.3 Hz, 1H), 8.75 (d, J=4.9 Hz, 1H), 8.45-8.28 (m, 1H), 7.95 (d, J=8.5 Hz, 1H), 7.79 (d, J=2.1 Hz, 1H), 7.64 (ddd, J=24.1, 8.2, 3.5 Hz, 2H), 7.19-6.99 (m, 4H), 4.27 (tt, J=8.0, 4.6 Hz, 1H), 3.91 (dd, J=13.8, 4.1 Hz, 1H), 3.86-3.67 (m, 4H), 3.40 (dd, J=13.8, 7.6 Hz, 1H), 3.14-2.98 (m, 2H), 2.92 (dt, J=9.5, 4.8 Hz, 4H), 2.78-2.59 (m, 2H).

Example 27: Synthesis of N-[2-[(2R)-3-(3,4-dihydro-1H-isoquinolin-2-yl)-2-hydroxy-propyl]-1-oxo-3,4-dihydroisoquinolin-6-yl]pyridine-4-carboxamide

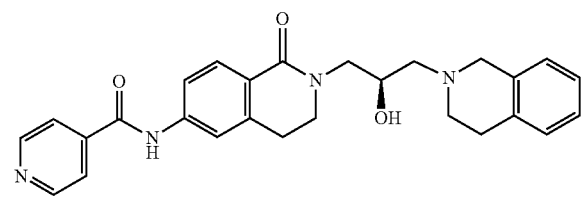 [SMILES: O=C(Nc1ccc2c(c1)CCN(C[C@H](O)CN1CCc3ccccc3C1)C2=O)c1ccncc1]

The title compound was synthesized in the same manner as in Example 18, except that pyridine-4-carboxamide was used instead of pyrrolidin-2-one.

$^1$H NMR (400 MHz, Methanol-$d_4$) δ 8.86-8.65 (m, 2H), 8.05-7.88 (m, 3H), 7.81 (d, J=2.1 Hz, 1H), 7.68 (dd, J=8.5, 2.1 Hz, 1H), 7.18-6.94 (m, 4H), 4.28 (tt, J=8.0, 4.6 Hz, 1H), 3.92 (dd, J=13.8, 4.1 Hz, 1H), 3.87-3.71 (m, 4H), 3.41 (dd, J=13.8, 7.6 Hz, 1H), 3.08 (q, J=8.7, 7.0 Hz, 2H), 2.93 (p, J=5.5, 4.6 Hz, 4H), 2.76-2.65 (m, 2H).

Example 28: Synthesis of 2-[(2R)-3-(3,4-dihydro-1H-isoquinolin-2-yl)-2-hydroxy-propyl]-6-(3,5-dimethyl-1-piperidyl)-3,4-dihydroisoquinolin-1-one

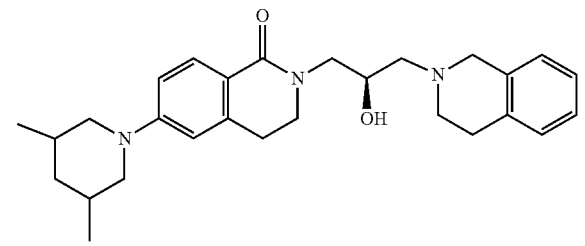 [SMILES: CC1CC(C)CN(c2ccc3c(c2)CCN(C[C@H](O)CN2CCc4ccccc4C2)C3=O)C1]

The title compound was synthesized in the same manner as in Example 2, except that 3,5-dimethylpiperidine was used instead of pyrrolidine.

$^1$H NMR (400 MHz, Methanol-$d_4$) δ 7.76 (t, J=8.0 Hz, 1H), 7.18-6.98 (m, 4H), 6.86 (dd, J=8.9, 2.6 Hz, 1H), 6.77-6.65 (m, 1H), 4.22 (tt, J=7.7, 4.6 Hz, 1H), 3.86 (ddd, J=11.9, 8.0, 4.0 Hz, 3H), 3.81-3.52 (m, 4H), 3.36 (d, J=7.7 Hz, 1H), 3.04-2.83 (m, 6H), 2.73-2.59 (m, 2H), 2.33 (t, J=12.0 Hz, 2H), 1.84 (d, J=13.0 Hz, 1H), 1.73 (qp, J=10.5, 3.8, 2.8 Hz, 2H), 1.08-0.88 (m, 6H), 0.79 (q, J=12.1 Hz, 1H).

Example 29: Synthesis of 2-[(2R)-3-(3,4-dihydro-1H-isoquinolin-2-yl)-2-hydroxy-propyl]-6-(3,5-dimethylpiperazin-1-yl)-3,4-dihydroisoquinolin-1-one

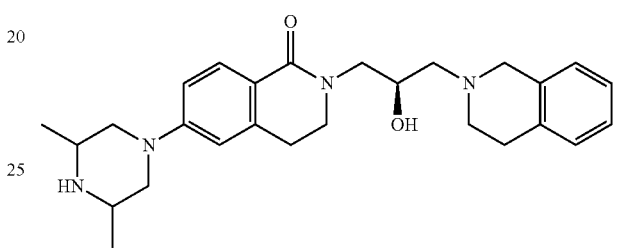

The title compound was synthesized in the same manner as in Example 2, except that 2,6-dimethylpiperazine was used instead of pyrrolidine.

$^1$H NMR (400 MHz, Methanol-$d_4$) δ 7.80 (d, J=8.7 Hz, 1H), 7.16-6.98 (m, 4H), 6.89 (dd, J=8.9, 2.5 Hz, 1H), 6.76 (d, J=2.5 Hz, 1H), 4.22 (tt, J=7.9, 4.5 Hz, 1H), 3.88 (dd, J=13.8, 4.2 Hz, 1H), 3.81-3.63 (m, 6H), 3.36 (d, J=7.5 Hz, 1H), 3.03-2.80 (m, 8H), 2.71-2.56 (m, 2H), 2.37 (t, J=11.5 Hz, 2H), 1.18 (d, J=6.3 Hz, 6H).

Example 30: Synthesis of 2-[(2R)-3-(3,4-dihydro-1H-isoquinolin-2-yl)-2-hydroxy-propyl]-6-(tetrahydrofuran-3-ylmethylamino)-3,4-dihydroisoquinolin-1-one

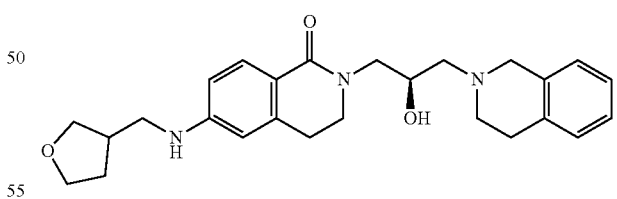

The title compound was synthesized in the same manner as in Example 2, except that tetrahydrofuran-3-ylmethanamine was used instead of pyrrolidine.

$^1$H NMR (400 MHz, Methanol-$d_4$) δ 7.71 (d, J=8.6 Hz, 1H), 7.18-6.97 (m, 4H), 6.55 (dd, J=8.7, 2.3 Hz, 1H), 6.40 (d, J=2.3 Hz, 1H), 4.21 (tt, J=7.8, 4.5 Hz, 1H), 3.88 (dp, J=13.0, 4.8 Hz, 3H), 3.80-3.67 (m, 4H), 3.67-3.54 (m, 2H), 3.33 (d, J=21.3 Hz, 1H), 3.14 (d, J=7.4 Hz, 2H), 2.87 (dt, J=18.1, 6.1 Hz, 6H), 2.68-2.52 (m, 3H), 2.10 (tp, J=11.2, 5.4 Hz, 1H), 1.69 (dq, J=13.4, 7.0 Hz, 1H).

Example 31: Synthesis of 2-[(2R)-3-(3,4-dihydro-1H-isoquinolin-2-yl)-2-hydroxy-propyl]-6-(4-piperidylmethylamino)-3,4-dihydroisoquinolin-1-one

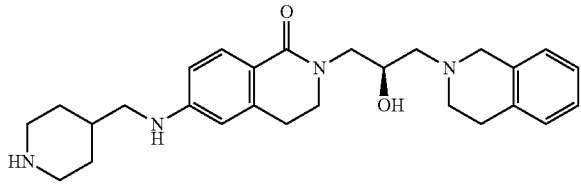 [SMILES: O=C1c2ccc(NCC3CCNCC3)cc2CCN1C[C@H](O)CN1CCc2ccccc2C1]

6-[(1-Acetyl-4-piperidyl)methylamino]-2-[(2R)-3-(3,4-dihydro-1H-isoquinolin-2-yl)-2-hydroxy-propyl]-3,4-dihydroisoquinolin-1-one (10 mg, 0.02 mmol) obtained in Example 24 was dissolved in 4 mL of methanol:$H_2O$ (1:1) solution, and NaOH was added in excess, heated and stirred under reflux. After completion of the reaction, the reaction mixture was extracted with ethyl acetate to obtain 3 mg of the title compound.

$^1$H NMR (400 MHz, Methanol-$d_4$) δ 7.69 (d, J=8.6 Hz, 1H), 7.17-6.97 (m, 4H), 6.53 (dd, J=8.8, 2.3 Hz, 1H), 6.39 (s, 1H), 4.28-4.12 (m, 1H), 3.87 (dd, J=13.8, 4.2 Hz, 1H), 3.78-3.60 (m, 4H), 3.34 (d, J=21.7 Hz, 1H), 3.08 (dd, J=20.6, 9.4 Hz, 4H), 2.97-2.79 (m, 6H), 2.63 (q, J=9.3, 6.6 Hz, 4H), 1.82 (t, J=15.1 Hz, 3H), 1.35-1.20 (m, 3H).

Example 32: Synthesis of 6-[(1-acetyl-4-piperidyl)amino]-2-[(2R)-3-(3,4-dihydro-1H-isoquinolin-2-yl)-2-hydroxy-propyl]-3,4-dihydroisoquinolin-1-one

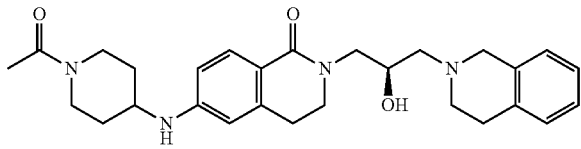 [SMILES: CC(=O)N1CCC(Nc2ccc3c(c2)CCN(C[C@H](O)CN2CCc4ccccc4C2)C3=O)CC1]

The title compound was synthesized in the same manner as in Example 2, except that 1-(4-amino-1-piperidyl)ethanone was used instead of pyrrolidine.

$^1$H NMR (400 MHz, Methanol-$d_4$) δ 7.71 (d, J=8.6 Hz, 1H), 7.16-6.99 (m, 4H), 6.58 (dd, J=8.7, 2.3 Hz, 1H), 6.45 (d, J=2.2 Hz, 1H), 4.40 (dd, J=13.6, 4.8 Hz, 1H), 4.21 (tt, J=8.0, 4.6 Hz, 1H), 3.88 (ddd, J=18.1, 13.5, 6.8 Hz, 2H), 3.80-3.57 (m, 5H), 3.39-3.24 (m, 1H), 2.99-2.79 (m, 7H), 2.72-2.58 (m, 2H), 2.12 (s, 3H), 2.07-1.97 (m, 2H), 1.51-1.28 (m, 3H).

Example 33: Synthesis of N-[2-[(2R)-3-(3,4-dihydro-1H-isoquinolin-2-yl)-2-hydroxy-propyl]-1-oxo-3,4-dihydroisoquinolin-6-yl]-2-morpholino-acetamide

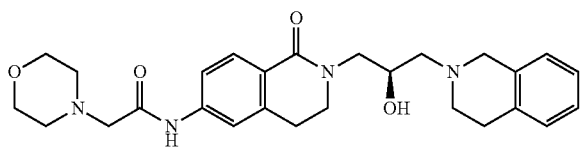 [SMILES: O=C(CN1CCOCC1)Nc1ccc2c(c1)CCN(C[C@H](O)CN1CCc3ccccc3C1)C2=O]

The title compound was synthesized in the same manner as in Example 18, except that 2-morpholinoacetamide was used instead of pyrrolidin-2-one.

$^1$H NMR (400 MHz, Chloroform-d) δ 9.21 (s, 1H), 8.04 (d, J=8.4 Hz, 1H), 7.73 (d, J=2.1 Hz, 1H), 7.34-7.22 (m, 1H), 7.12 (qd, J=8.6, 7.3, 4.1 Hz, 3H), 7.05-6.91 (m, 1H), 4.13 (ddt, J=10.4, 7.1, 3.7 Hz, 1H), 3.89 (dd, J=14.0, 3.2 Hz, 1H), 3.85-3.76 (m, 5H), 3.76-3.68 (m, 2H), 3.63 (d, J=14.9 Hz, 1H), 3.45 (dd, J=14.0, 6.3 Hz, 1H), 3.16 (s, 2H), 3.06-2.97 (m, 2H), 2.97-2.86 (m, 3H), 2.74 (dd, J=9.8, 5.7 Hz, 1H), 2.64 (q, J=6.5, 4.8 Hz, 4H), 2.59-2.51 (m, 2H).

Example 34: Synthesis of 2-[(2R)-3-(3,4-dihydro-1H-isoquinolin-2-yl)-2-hydroxy-propyl]-6-(4-piperidylamino)-3,4-dihydroisoquinolin-1-one

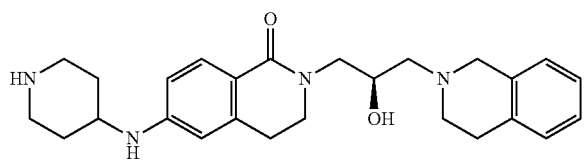 [SMILES: O=C1c2ccc(NC3CCNCC3)cc2CCN1C[C@H](O)CN1CCc2ccccc2C1]

6-[(1-Acetyl-4-piperidyl)amino]-2-[(2R)-3-(3,4-dihydro-1H-isoquinolin-2-yl)-2-hydroxy-propyl]-3,4-dihydroisoquinolin-1-one obtained in Example 32 as a starting material was used in the same manner as in Example 31 to obtain the title compound.

$^1$H NMR (400 MHz, Methanol-$d_4$) δ 7.69 (d, J=8.5 Hz, 1H), 7.23-6.96 (m, 4H), 6.56 (dd, J=8.6, 2.3 Hz, 1H), 6.47-6.31 (m, 1H), 4.21 (tt, J=8.2, 4.6 Hz, 1H), 3.87 (dd, J=13.8, 4.2 Hz, 1H), 3.77-3.61 (m, 4H), 3.51-3.44 (m, 1H), 3.37 (s, 1H), 3.12 (dt, J=13.0, 3.8 Hz, 2H), 2.98-2.81 (m, 6H), 2.76 (td, J=12.3, 2.7 Hz, 2H), 2.69-2.56 (m, 2H), 2.10-1.99 (m, 2H), 1.50-1.37 (m, 2H).

Example 35: Synthesis of 2-[(2R)-3-(3,4-dihydro-1H-isoquinolin-2-yl)-2-hydroxy-propyl]-6-[4-(hydroxymethyl)-1-piperidyl]-3,4-dihydroisoquinolin-1-one

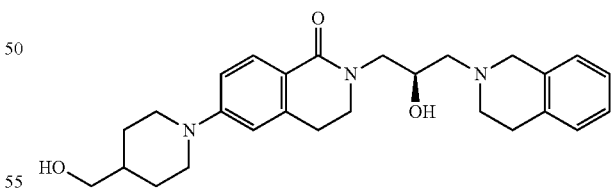

The title compound was synthesized in the same manner as in Example 2, except that 4-piperidylmethanol was used instead of pyrrolidine.

$^1$H NMR (400 MHz, Methanol-$d_4$) δ 7.78 (d, J=8.7 Hz, 1H), 7.19-6.97 (m, 4H), 6.87 (dd, J=8.9, 2.5 Hz, 1H), 6.74 (d, J=2.5 Hz, 1H), 4.22 (tt, J=7.6, 4.6 Hz, 1H), 4.02-3.81 (m, 3H), 3.81-3.60 (m, 4H), 3.44 (d, J=6.3 Hz, 2H), 3.36 (d, J=7.4 Hz, 1H), 3.02-2.75 (m, 8H), 2.71-2.57 (m, 2H), 1.91-1.77 (m, 2H), 1.69 (ttt, J=10.2, 6.5, 3.7 Hz, 1H), 1.32 (tt, J=12.5, 6.3 Hz, 2H).

Example 36: Synthesis of 2-[(2R)-3-(3,4-dihydro-1H-isoquinolin-2-yl)-2-hydroxy-propyl]-6-[3-(hydroxymethyl)-1-piperidyl]-3,4-dihydroisoquinolin-1-one

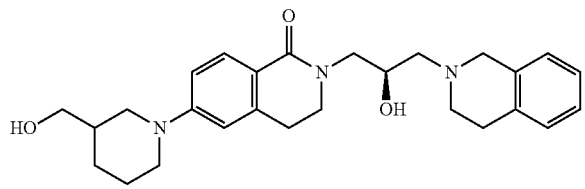 [SMILES: O=C1c2ccc(N3CCCC(CO)C3)cc2CCN1C[C@H](O)CN1CCc2ccccc2C1]

The title compound was synthesized in the same manner as in Example 2, except that 3-piperidylmethanol was used instead of pyrrolidine.

$^1$H NMR (400 MHz, Methanol-$d_4$) δ 7.78 (d, J=8.8 Hz, 1H), 7.17-6.99 (m, 4H), 6.87 (dd, J=8.8, 2.5 Hz, 1H), 6.74 (d, J=2.5 Hz, 1H), 4.21 (td, J=7.5, 3.8 Hz, 1H), 4.00-3.90 (m, 1H), 3.87 (dd, J=13.8, 4.2 Hz, 1H), 3.83-3.76 (m, 1H), 3.76-3.61 (m, 4H), 3.53 (dd, J=10.9, 5.1 Hz, 1H), 3.45 (dd, J=10.9, 7.5 Hz, 1H), 3.36 (d, J=7.4 Hz, 1H), 3.00-2.79 (m, 7H), 2.66-2.58 (m, 3H), 1.89-1.73 (m, 3H), 1.64 (qt, J=12.6, 4.5 Hz, 1H), 1.30-1.16 (m, 1H).

Example 37: Synthesis of 2-[(2R)-3-(3,4-dihydro-1H-isoquinolin-2-yl)-2-hydroxy-propyl]-6-(4-hydroxy-1-piperidyl)-3,4-dihydroisoquinolin-1-one

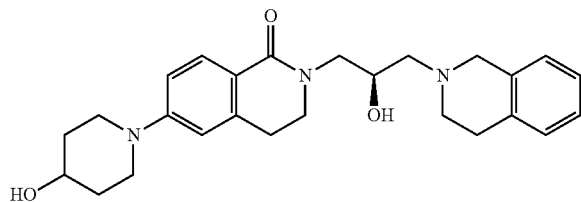 [SMILES: O=C1c2ccc(N3CCC(O)CC3)cc2CCN1C[C@H](O)CN1CCc2ccccc2C1]

The title compound was synthesized in the same manner as in Example 2, except that 4-hydroxypiperidine was used instead of pyrrolidine.

$^1$H NMR (400 MHz, Methanol-$d_4$) δ 7.78 (d, J=8.8 Hz, 1H), 7.20-6.97 (m, 4H), 6.89 (dd, J=8.8, 2.5 Hz, 1H), 6.76 (d, J=2.5 Hz, 1H), 4.22 (tt, J=7.7, 4.7 Hz, 1H), 3.95-3.58 (m, 8H), 3.37 (d, J=7.5 Hz, 1H), 3.13-2.79 (m, 8H), 2.71-2.55 (m, 2H), 1.95 (dq, J=12.6, 4.0 Hz, 2H), 1.59 (dtd, J=13.2, 9.6, 3.8 Hz, 2H).

Example 38: Synthesis of 2-[(2R)-3-(3,4-dihydro-1H-isoquinolin-2-yl)-2-hydroxy-propyl]-6-(3-hydroxy-1-piperidyl)-3,4-dihydroisoquinolin-1-one

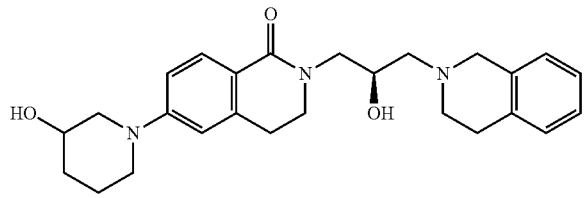 [SMILES: O=C1c2ccc(N3CCCC(O)C3)cc2CCN1C[C@H](O)CN1CCc2ccccc2C1]

The title compound was synthesized in the same manner as in Example 2, except that 3-hydroxypiperidine was used instead of pyrrolidine.

$^1$H NMR (400 MHz, Methanol-$d_4$) δ 7.78 (d, J=8.8 Hz, 1H), 7.19-6.97 (m, 4H), 6.87 (dd, J=8.8, 2.5 Hz, 1H), 6.74 (d, J=2.5 Hz, 1H), 4.22 (tt, J=7.7, 4.6 Hz, 1H), 3.87 (dd, J=13.8, 4.2 Hz, 1H), 3.82-3.57 (m, 7H), 3.36 (d, J=7.5 Hz, 1H), 3.01-2.77 (m, 8H), 2.69-2.58 (m, 2H), 2.00 (d, J=5.0 Hz, 1H), 1.87 (dh, J=12.8, 4.3 Hz, 1H), 1.63 (dtt, J=14.2, 10.6, 3.9 Hz, 1H), 1.48 (tdd, J=12.0, 9.0, 4.0 Hz, 1H).

Example 39: Synthesis of 2-[(2R)-3-(3,4-dihydro-1H-isoquinolin-2-yl)-2-hydroxy-propyl]-6-oxazolidin-3-yl-3,4-dihydroisoquinolin-1-one

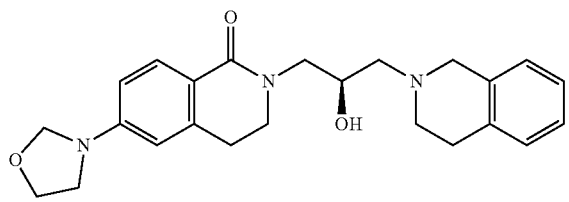 [SMILES: O=C1c2ccc(N3CCOC3)cc2CCN1C[C@H](O)CN1CCc2ccccc2C1]

The title compound was synthesized in the same manner as in Example 2, except that oxazolidine was used instead of pyrrolidine.

$^1$H NMR (400 MHz, Methanol-$d_4$) δ 7.81 (d, J=8.6 Hz, 1H), 7.17-6.97 (m, 4H), 6.49 (dd, J=8.6, 2.4 Hz, 1H), 6.36 (d, J=2.4 Hz, 1H), 4.27-4.13 (m, 3H), 3.88 (dd, J=13.8, 4.2 Hz, 1H), 3.82-3.61 (m, 5H), 3.47 (t, J=6.4 Hz, 2H), 3.40-3.34 (m, 1H), 3.04-2.81 (m, 7H), 2.70-2.56 (m, 2H).

Example 40: Synthesis of 2-[(2R)-3-(3,4-dihydro-1H-isoquinolin-2-yl)-2-hydroxy-propyl]-6-(3-methylmorpholin-4-yl)-3,4-dihydroisoquinolin-1-one

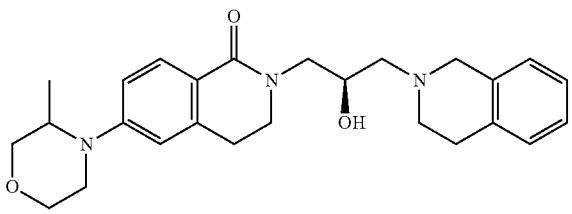 [SMILES: CC1COCCN1c1ccc2c(c1)CCN(C[C@H](O)CN1CCc3ccccc3C1)C2=O]

The title compound was synthesized in the same manner as in Example 2, except that 3-methylmorpholine was used instead of pyrrolidine.

$^1$H NMR (400 MHz, Methanol-$d_4$) δ 7.81 (d, J=8.7 Hz, 1H), 7.17-7.01 (m, 4H), 6.85 (dd, J=8.8, 2.5 Hz, 1H), 6.72 (d, J=2.5 Hz, 1H), 4.22 (tt, J=7.6, 4.6 Hz, 1H), 4.02 (td, J=12.5, 11.6, 5.3 Hz, 2H), 3.88 (dd, J=13.7, 4.2 Hz, 1H), 3.83-3.60 (m, 7H), 3.40-3.34 (m, 2H), 3.18 (td, J=12.2, 3.8 Hz, 1H), 3.01-2.78 (m, 6H), 2.68-2.58 (m, 2H), 1.16 (d, J=6.6 Hz, 3H).

Example 41: Synthesis of N-[2-[(2R)-3-(3,4-dihydro-1H-isoquinolin-2-yl)-2-hydroxy-propyl]-1-oxo-3,4-dihydroisoquinolin-6-yl]-2-hydroxy-acetamide

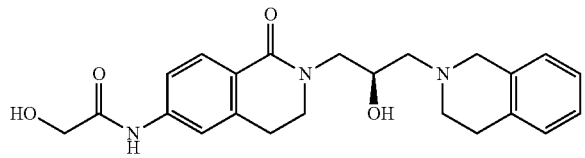 [SMILES: O=C(CO)Nc1ccc2c(c1)CCN(C[C@H](O)CN1CCc3ccccc3C1)C2=O]

The title compound was synthesized in the same manner as in Example 18, except that 2-hydroxyacetamide was used instead of pyrrolidin-2-one.

$^1$H NMR (400 MHz, Methanol-$d_4$) δ 7.91 (d, J=8.5 Hz, 1H), 7.69 (d, J=2.1 Hz, 1H), 7.57 (dd, J=8.4, 2.1 Hz, 1H), 7.17-7.09 (m, 3H), 7.06 (d, J=5.8 Hz, 1H), 4.27 (tt, J=8.1, 4.7 Hz, 1H), 4.15 (s, 2H), 3.90 (dd, J=13.8, 4.2 Hz, 1H), 3.85-3.67 (m, 4H), 3.41 (dd, J=13.8, 7.5 Hz, 1H), 3.04 (q, J=8.6, 7.0 Hz, 2H), 2.95 (s, 4H), 2.77-2.66 (m, 2H).

Example 42: Synthesis of N-[2-[(2R)-3-(3,4-dihydro-1H-isoquinolin-2-yl)-2-hydroxy-propyl]-1-oxo-3,4-dihydroisoquinolin-6-yl]acetamide

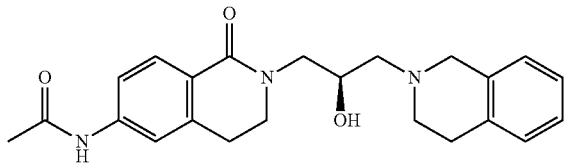 [SMILES: CC(=O)Nc1ccc2c(c1)CCN(C[C@H](O)CN1CCc3ccccc3C1)C2=O]

The title compound was synthesized in the same manner as in Example 18, except that acetamide was used instead of pyrrolidin-2-one.

$^1$H NMR (400 MHz, Methanol-$d_4$) δ 7.88 (d, J=8.5 Hz, 1H), 7.62 (d, J=2.1 Hz, 1H), 7.45 (dd, J=8.6, 2.1 Hz, 1H), 7.16-6.99 (m, 4H), 4.24 (tt, J=7.6, 4.6 Hz, 1H), 3.90 (dd, J=13.8, 4.1 Hz, 1H), 3.83-3.63 (m, 4H), 3.37 (dd, J=13.7, 7.6 Hz, 1H), 3.07-2.81 (m, 6H), 2.69-2.60 (m, 2H), 2.16 (s, 3H).

Example 43: Synthesis of 2-[(2R)-3-(3,4-dihydro-1H-isoquinolin-2-yl)-2-hydroxy-propyl]-6-(morpholinomethyl)-3,4-dihydroisoquinolin-1-one

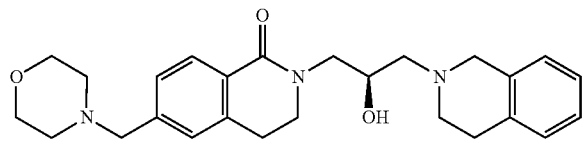 [SMILES: O=C1c2ccc(CN3CCOCC3)cc2CCN1C[C@H](O)CN1CCc2ccccc2C1]

6-Bromo-2-[(2R)-3-(3,4-dihydro-1H-isoquinolin-2-yl)-2-hydroxy-propyl]-3,4-dihydroisoquinolin-1-one (100 mg, 0.24 mmol) obtained in Example 1, potassium (morpholin-4-yl)methyltrifluoroborate (55 mg, 0.26 mmol), palladium acetate (3 mg, 0.012 mmol), XPhos (11 mg, 0.023 mmol) and Cs$_2$CO$_3$ (228 mg, 0.70 mmol) were dissolved in 3 mL of tetrahydrofuran:distilled water (=10:1) solvent, filled with nitrogen and stirred at 80° C. for 16 hours. The reaction solution was cooled to room temperature, diluted with ethyl acetate and filtered through Celite. The obtained solution was concentrated under reduced pressure and purified by flash chromatography to obtain 26 mg of the title compound (white).

$^1$H NMR (400 MHz, Methanol-$d_4$) δ 7.91 (d, J=7.9 Hz, 1H), 7.35 (d, J=8.0 Hz, 1H), 7.28 (s, 1H), 7.15-7.00 (m, 4H), 4.25 (tt, J=7.8, 4.6 Hz, 1H), 3.91 (dd, J=13.8, 4.2 Hz, 1H), 3.85-3.66 (m, 8H), 3.56 (s, 2H), 3.39 (dd, J=13.7, 7.7 Hz, 1H), 3.09-2.98 (m, 2H), 2.96-2.82 (m, 4H), 2.70-2.61 (m, 2H), 2.47 (t, J=4.6 Hz, 4H).

Example 44: Synthesis of 2-[(2R)-3-(3,4-dihydro-1H-isoquinolin-2-yl)-2-hydroxy-propyl]-6-(2-oxa-6-azaspiro[3.3]heptan-6-yl)-3,4-dihydroisoquinolin-1-one

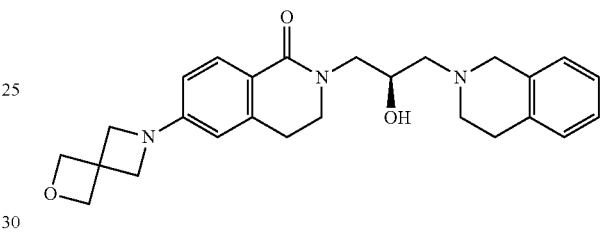

The title compound was synthesized in the same manner as in Example 43, except that 2-oxa-6-azaspiro[3.3]heptane was used instead of potassium (morpholin-4-yl)methyltrifluoroborate.

$^1$H NMR (400 MHz, Methanol-$d_4$) δ 7.77 (d, J=8.5 Hz, 1H), 7.19-6.98 (m, 4H), 6.39 (dd, J=8.5, 2.3 Hz, 1H), 6.26 (d, J=2.3 Hz, 1H), 4.86 (s, 4H), 4.24 (tt, J=7.8, 4.5 Hz, 1H), 4.11 (s, 4H), 3.86 (d, J=17.1 Hz, 3H), 3.79-3.59 (m, 2H), 3.37 (dd, J=13.9, 7.3 Hz, 1H), 2.95 (d, J=6.2 Hz, 6H), 2.81-2.64 (m, 2H).

Example 45: Synthesis of 3-[2-[(2R)-3-(3,4-dihydro-1H-isoquinolin-2-yl)-2-hydroxy-propyl]-1-oxo-3,4-dihydroisoquinolin-6-yl]oxazolidin-2-one

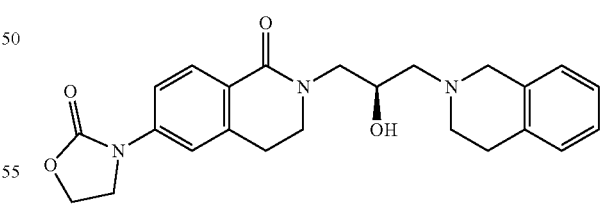

The title compound was synthesized in the same manner as in Example 18, except that oxazolidin-2-one was used instead of pyrrolidin-2-one.

$^1$H NMR (400 MHz, Methanol-$d_4$) δ 7.95 (d, J=8.6 Hz, 1H), 7.63-7.47 (m, 2H), 7.16-6.97 (m, 4H), 4.52 (t, J=8.0 Hz, 2H), 4.25 (tt, J=7.9, 4.6 Hz, 1H), 4.17-4.06 (m, 2H), 3.91 (dd, J=13.8, 4.1 Hz, 1H), 3.85-3.68 (m, 4H), 3.38 (dd, J=13.7, 7.7 Hz, 1H), 3.10-2.98 (m, 2H), 2.98-2.81 (m, 4H), 2.71-2.58 (m, 2H).

Example 46: Synthesis of 2-[(2R)-3-(3,4-dihydro-1H-isoquinolin-2-yl)-2-hydroxy-propyl]-6-[3-(hydroxymethyl)azetidin-1-yl]-3,4-dihydroisoquinolin-1-one

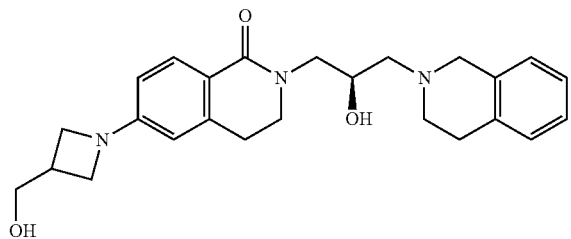 [SMILES: O=C1c2ccc(N3CC(CO)C3)cc2CCN1C[C@H](O)CN1CCc2ccccc2C1]

The title compound was synthesized in the same manner as in Example 2, except that azetidin-3-ylmethanol was used instead of pyrrolidine.

$^1$H NMR (400 MHz, Methanol-$d_4$) δ 7.76 (d, J=8.5 Hz, 1H), 7.19-6.99 (m, 4H), 6.35 (dd, J=8.5, 2.3 Hz, 1H), 6.22 (d, J=2.4 Hz, 1H), 4.22 (tt, J=8.1, 4.7 Hz, 1H), 4.00 (t, J=7.8 Hz, 2H), 3.87 (dd, J=13.8, 4.2 Hz, 1H), 3.79-3.59 (m, 8H), 3.36 (d, J=7.4 Hz, 1H), 2.98-2.80 (m, 7H), 2.69-2.57 (m, 2H).

Example 47: Synthesis of 2-[(2R)-3-(3,4-dihydro-1H-isoquinolin-2-yl)-2-hydroxy-propyl]-6-[(2S)-2-methylmorpholin-4-yl]-3,4-dihydroisoquinolin-1-one

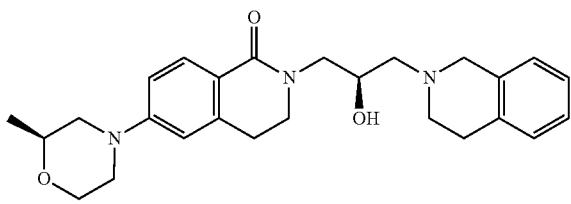 [SMILES: C[C@H]1CN(c2ccc3c(c2)CCN(C[C@H](O)CN2CCc4ccccc4C2)C3=O)CCO1]

The title compound was synthesized in the same manner as in Example 2, except that (2S)-2-methylmorpholine was used instead of pyrrolidine.

$^1$H NMR (400 MHz, Methanol-$d_4$) δ 7.81 (d, J=8.7 Hz, 1H), 7.16-6.99 (m, 4H), 6.88 (dd, J=8.9, 2.5 Hz, 1H), 6.75 (d, J=2.5 Hz, 1H), 4.21 (tt, J=7.7, 4.6 Hz, 1H), 3.98 (dd, J=11.4, 3.3 Hz, 1H), 3.87 (dd, J=13.8, 4.1 Hz, 1H), 3.81-3.56 (m, 8H), 3.34 (d, J=13.4 Hz, 1H), 3.02-2.77 (m, 7H), 2.70-2.55 (m, 2H), 2.48 (dd, J=12.5, 10.6 Hz, 1H), 1.24 (d, J=6.1 Hz, 3H).

Example 48: Synthesis of 2-[(2R)-3-(3,4-dihydro-1H-isoquinolin-2-yl)-2-hydroxy-propyl]-6-(4-methoxy-1-piperidyl)-3,4-dihydroisoquinolin-1-one

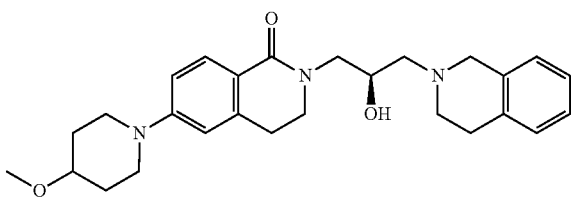 [SMILES: COC1CCN(c2ccc3c(c2)CCN(C[C@H](O)CN2CCc4ccccc4C2)C3=O)CC1]

The title compound was synthesized in the same manner as in Example 2, except that 4-methoxypiperidine was used instead of pyrrolidine.

$^1$H NMR (400 MHz, Methanol-$d_4$) δ 7.78 (d, J=8.7 Hz, 1H), 7.19-6.99 (m, 4H), 6.87 (dd, J=8.9, 2.5 Hz, 1H), 6.74 (d, J=2.5 Hz, 1H), 4.21 (tt, J=7.8, 4.6 Hz, 1H), 3.87 (dd, J=13.8, 4.1 Hz, 1H), 3.78-3.59 (m, 6H), 3.45 (tt, J=8.2, 3.9 Hz, 1H), 3.38 (s, 4H), 3.08 (ddd, J=12.8, 9.3, 3.2 Hz, 2H), 2.99-2.77 (m, 6H), 2.67-2.55 (m, 2H), 1.99 (dq, J=13.0, 4.6, 3.7 Hz, 2H), 1.60 (dtd, J=12.8, 9.0, 3.6 Hz, 2H).

Example 49: Synthesis of 2-[(2R)-3-(3,4-dihydro-1H-isoquinolin-2-yl)-2-hydroxy-propyl]-6-(1,1-dioxo-1,4-thiazinan-4-yl)-3,4-dihydroisoquinolin-1-one

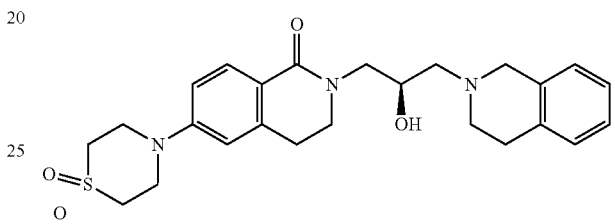

The title compound was synthesized in the same manner as in Example 2, except that 1,4-thiazinane 1,1-dioxide was used instead of pyrrolidine.

$^1$H NMR (400 MHz, Methanol-$d_4$) δ 7.85 (d, J=8.7 Hz, 1H), 7.16-6.99 (m, 4H), 6.96 (dd, J=8.8, 2.6 Hz, 1H), 6.85 (d, J=2.6 Hz, 1H), 4.22 (tt, J=7.8, 4.6 Hz, 1H), 3.97 (t, J=5.1 Hz, 4H), 3.87 (dd, J=13.8, 4.2 Hz, 1H), 3.79-3.62 (m, 4H), 3.40-3.30 (m, 1H), 3.10 (t, J=5.0 Hz, 4H), 3.07-2.76 (m, 6H), 2.67-2.54 (m, 2H).

Example 50: Synthesis of 2-[(2R)-3-(3,4-dihydro-1H-isoquinolin-2-yl)-2-hydroxy-propyl]-6-(tetrahydrofuran-3-ylamino)-3,4-dihydroisoquinolin-1-one

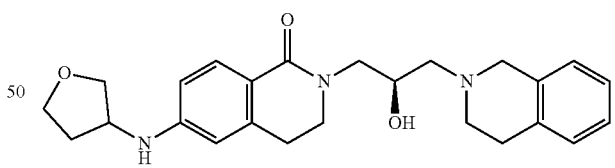

The title compound was synthesized in the same manner as in Example 2, except that tetrahydrofuran-3-amine was used instead of pyrrolidine.

$^1$H NMR (400 MHz, Methanol-$d_4$) δ 7.71 (d, J=8.6 Hz, 1H), 7.18-7.00 (m, 4H), 6.56 (dd, J=8.5, 2.3 Hz, 1H), 6.42 (s, 1H), 4.22 (dp, J=7.6, 4.5 Hz, 1H), 4.14 (q, J=7.0 Hz, 1H), 4.03-3.92 (m, 2H), 3.86 (dq, J=14.1, 5.6, 4.5 Hz, 2H), 3.78-3.59 (m, 5H), 3.36 (d, J=7.3 Hz, 1H), 2.90 (dt, J=18.5, 5.8 Hz, 6H), 2.69-2.56 (m, 2H), 2.29 (dt, J=14.8, 7.4 Hz, 1H), 1.91 (td, J=9.8, 9.1, 5.0 Hz, 1H).

Example 51: Synthesis of 2-[(2R)-3-(3,4-dihydro-1H-isoquinolin-2-yl)-2-hydroxy-propyl]-6-(oxetan-3-ylamino)-3,4-dihydroisoquinolin-1-one

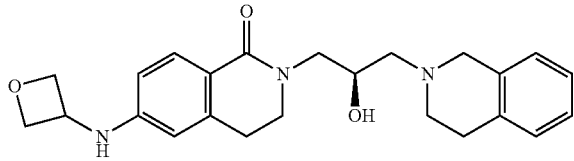 [SMILES: O=C1c2ccc(NC3COC3)cc2CCN1C[C@H](O)CN1CCc2ccccc2C1]

The title compound was synthesized in the same manner as in Example 2, except that oxetan-3-amine was used instead of pyrrolidine.

¹H NMR (400 MHz, Methanol-d₄) δ 7.72 (d, J=8.5 Hz, 1H), 7.16-7.00 (m, 4H), 6.47 (dd, J=8.6, 2.3 Hz, 1H), 6.31 (d, J=2.3 Hz, 1H), 4.99 (t, J=6.5 Hz, 2H), 4.68 (p, J=6.4 Hz, 1H), 4.56 (t, J=6.1 Hz, 2H), 4.21 (tt, J=7.8, 4.6 Hz, 1H), 3.86 (dd, J=13.8, 4.2 Hz, 1H), 3.76-3.58 (m, 4H), 3.35 (s, 1H), 2.87 (dt, J=22.0, 6.0 Hz, 6H), 2.72-2.55 (m, 2H).

Example 52: Synthesis of 6-(4-acetylpiperazin-1-yl)-2-[(2R)-3-(3,4-dihydro-1H-isoquinolin-2-yl)-2-hydroxy-propyl]-3,4-dihydroisoquinolin-1-one

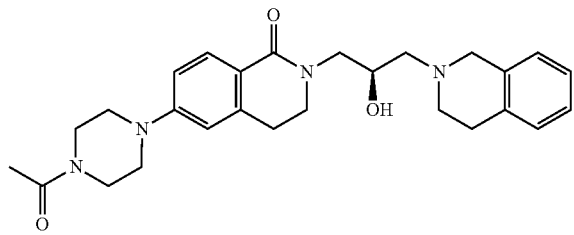

The title compound was synthesized in the same manner as in Example 2, except that N-acetylpiperazine was used instead of pyrrolidine.

¹H NMR (400 MHz, Methanol-d₄) δ 7.82 (d, J=8.7 Hz, 1H), 7.15-6.99 (m, 4H), 6.91 (dd, J=8.8, 2.5 Hz, 1H), 6.78 (d, J=2.6 Hz, 1H), 4.22 (tt, J=7.8, 4.7 Hz, 1H), 3.88 (dd, J=13.8, 4.1 Hz, 1H), 3.79-3.63 (m, 8H), 3.42-3.32 (m, 5H), 3.00-2.79 (m, 6H), 2.71-2.57 (m, 2H), 2.16 (s, 3H).

Example 53: Synthesis of tert-butyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate

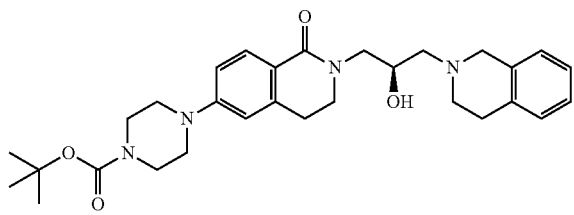 [SMILES: CC(C)(C)OC(=O)N1CCN(c2ccc3c(c2)CCN(C[C@H](O)CN2CCc4ccccc4C2)C3=O)CC1]

The title compound was synthesized in the same manner as in Example 2, except that tert-butyl piperazine-1-carboxylate was used instead of pyrrolidine.

¹H NMR (400 MHz, Methanol-d₄) δ 7.81 (d, J=8.7 Hz, 1H), 7.15-7.00 (m, 4H), 6.90 (dd, J=8.7, 2.5 Hz, 1H), 6.78 (d, J=2.6 Hz, 1H), 4.22 (tt, J=7.9, 4.6 Hz, 1H), 3.88 (dd, J=13.8, 4.1 Hz, 1H), 3.79-3.62 (m, 4H), 3.57 (t, J=4.9 Hz, 4H), 3.39-3.28 (m, 5H), 3.02-2.79 (m, 6H), 2.69-2.57 (m, 2H), 1.50 (s, 9H).

Example 54: Synthesis of 2-[(2R)-3-(3,4-dihydro-1H-isoquinolin-2-yl)-2-hydroxy-propyl]-6-(1,4-oxazepan-4-ylmethyl)-3,4-dihydroisoquinolin-1-one

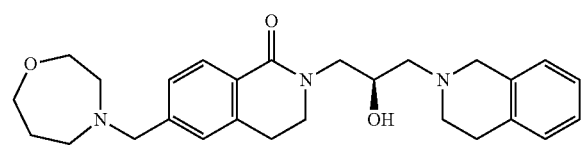 [SMILES: O=C1c2ccc(CN3CCCOCC3)cc2CCN1C[C@H](O)CN1CCc2ccccc2C1]

The title compound was synthesized in the same manner as in Example 43, except that potassium (1,4-oxazepan-4-yl)methyltrifluoroborate was used instead of potassium (morpholin-4-yl)methyltrifluoroborate.

¹H NMR (400 MHz, Methanol-d₄) δ 7.91 (d, J=7.9 Hz, 1H), 7.36 (d, J=8.0 Hz, 1H), 7.29 (s, 1H), 7.16-7.01 (m, 4H), 4.25 (tt, J=8.0, 4.6 Hz, 1H), 3.91 (dd, J=13.7, 4.2 Hz, 1H), 3.87-3.67 (m, 10H), 3.38 (dd, J=13.8, 7.6 Hz, 1H), 3.07-2.97 (m, 2H), 2.96-2.80 (m, 4H), 2.78-2.67 (m, 4H), 2.67-2.58 (m, 2H), 1.92 (p, J=5.9 Hz, 2H).

Example 55: Synthesis of 2-[(2R)-3-(3,4-dihydro-1H-isoquinolin-2-yl)-2-hydroxy-propyl]-6-(4-methyl-3-oxo-piperazin-1-yl)-3,4-dihydroisoquinolin-1-one

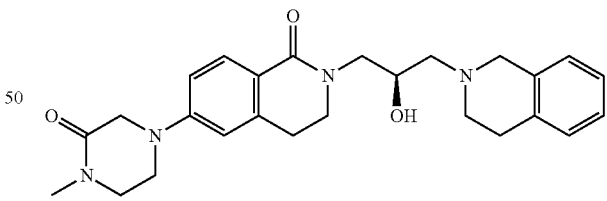

The title compound was synthesized in the same manner as in Example 2, except that 1-methylpiperazin-2-one was used instead of pyrrolidine.

¹H NMR (400 MHz, Methanol-d₄) δ 7.84 (d, J=8.7 Hz, 1H), 7.16-6.98 (m, 4H), 6.87 (dd, J=8.8, 2.5 Hz, 1H), 6.80-6.62 (m, 1H), 4.22 (dh, J=10.4, 5.6, 5.0 Hz, 1H), 3.95 (s, 2H), 3.88 (dd, J=13.8, 4.2 Hz, 1H), 3.81-3.60 (m, 6H), 3.54 (t, J=5.4 Hz, 2H), 3.37 (d, J=7.4 Hz, 1H), 3.04 (s, 3H), 3.02-2.81 (m, 6H), 2.69-2.59 (m, 2H).

Example 56: Synthesis of tert-butyl 4-[2-[(2R)-3-(3,4-dihydro-1H-isoquinolin-2-yl)-2-hydroxy-propyl]-1-oxo-3,4-dihydroisoquinolin-6-yl]-3,6-dihydro-2H-pyridine-1-carboxylate

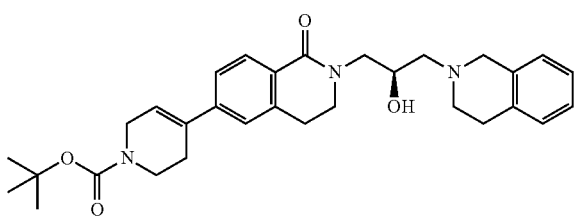 [SMILES: CC(C)(C)OC(=O)N1CC=C(c2ccc3c(c2)CCN(C[C@H](O)CN2CCc4ccccc4C2)C3=O)CC1]

The title compound was synthesized in the same manner as in Example 8, except that (1-tert-butoxycarbonyl-3,6-dihydro-2H-pyridin-4-yl)boronic acid pinacol ester was used instead of 4-pyridylboronic acid.

$^1$H NMR (400 MHz, Methanol-$d_4$) δ 7.91 (d, J=8.2 Hz, 1H), 7.44 (d, J=8.2 Hz, 1H), 7.35 (s, 1H), 7.16-6.96 (m, 4H), 6.25 (s, 1H), 4.32-4.20 (m, 1H), 4.11 (s, 2H), 3.92 (dd, J=13.7, 4.1 Hz, 1H), 3.77 (d, J=16.8 Hz, 4H), 3.66 (s, 2H), 3.39 (dd, J=13.7, 7.7 Hz, 1H), 3.10-2.97 (m, 2H), 2.90 (dd, J=18.0, 5.4 Hz, 4H), 2.71-2.61 (m, 2H), 2.57 (s, 2H), 1.51 (s, 9H).

Example 57: Synthesis of 2-[(2R)-3-(3,4-dihydro-1H-isoquinolin-2-yl)-2-hydroxy-propyl]-6-(1,2,3,6-tetrahydropyridin-4-yl)-3,4-dihydroisoquinolin-1-one

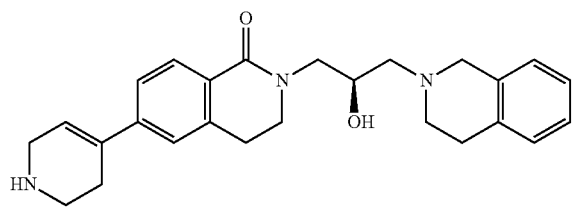 [SMILES: O=C1c2ccc(C3=CCNCC3)cc2CCN1C[C@H](O)CN1CCc2ccccc2C1]

Tert-butyl 4-[2-[(2R)-3-(3,4-dihydro-1H-isoquinolin-2-yl)-2-hydroxy-propyl]-1-oxo-3,4-dihydroisoquinolin-6-yl]-3,6-dihydro-2H-pyridine-1-carboxylate (44 mg, 0.08 mmol) obtained in Example 56 was dissolved in 4 mL of dichloromethane, and 4 M hydrochloric acid (solution in dioxane) solution was added in excess and stirred at room temperature. After completion of the reaction, the reaction mixture was neutralized with 2 N NaOH solution and extracted with a mixed solution of isopropanol and dichloromethane (1:10) to obtain 19 mg of the title compound.

$^1$H NMR (400 MHz, Methanol-$d_4$) δ 7.93 (d, J=8.2 Hz, 1H), 7.46 (d, J=8.2 Hz, 1H), 7.38 (s, 1H), 7.17-6.99 (m, 4H), 6.31 (d, J=4.5 Hz, 1H), 4.26 (t, J=5.6 Hz, 1H), 3.92 (dd, J=13.7, 4.1 Hz, 1H), 3.86-3.66 (m, 6H), 3.40 (dd, J=13.7, 7.7 Hz, 1H), 3.30 (d, J=6.0 Hz, 2H), 3.12-2.99 (m, 2H), 2.91 (dd, J=15.5, 5.4 Hz, 4H), 2.76-2.60 (m, 4H).

Example 58: Synthesis of 2-[(2R)-3-(3,4-dihydro-1H-isoquinolin-2-yl)-2-hydroxy-propyl]-6-piperazin-1-yl-3,4-dihydroisoquinolin-1-one

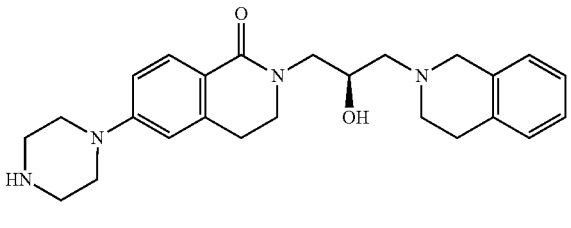 [SMILES: O=C1c2ccc(N3CCNCC3)cc2CCN1C[C@H](O)CN1CCc2ccccc2C1]

Tert-butyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate obtained in Example 53 as a starting material was used in the same manner as in Example 57 to obtain the title compound.

$^1$H NMR (400 MHz, Methanol-$d_4$) δ 7.81 (d, J=8.7 Hz, 1H), 7.18-7.00 (m, 4H), 6.96-6.87 (m, 1H), 6.79 (s, 1H), 4.23 (dp, J=8.4, 4.8 Hz, 1H), 3.88 (dd, J=13.8, 4.2 Hz, 1H), 3.82-3.64 (m, 4H), 3.37 (dd, J=11.5, 5.9 Hz, 5H), 3.04 (t, J=5.0 Hz, 4H), 3.01-2.83 (m, 6H), 2.66 (dd, J=6.1, 4.0 Hz, 2H).

Example 59: Synthesis of 2-[(2R)-3-(3,4-dihydro-1H-isoquinolin-2-yl)-2-hydroxy-propyl]-6-(4-methylsulfonylpiperazin-1-yl)-3,4-dihydroisoquinolin-1-one

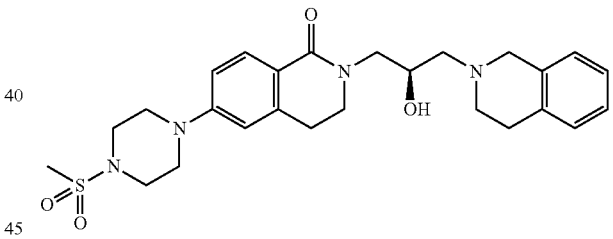

2-[(2R)-3-(3,4-dihydro-1H-isoquinolin-2-yl)-2-hydroxy-propyl]-6-piperazin-1-yl-3,4-dihydroisoquinolin-1-one (18 mg, 0.04 mmol) obtained in Example 58, triethylamine (12 μL, 0.08 mmol) and methanesulfonyl chloride (4 μL, 0.05 mmol) were dissolved in 3 mL of dichloromethane and stirred at room temperature. The reaction was terminated by adding a saturated aqueous solution of ammonium chloride to the reaction mixture, followed by extraction with ethyl acetate. The organic layer was dried over anhydrous magnesium sulfate. The solvent was dried under reduced pressure, and purification was carried out by flash chromatography to obtain 7 mg of the title compound.

$^1$H NMR (400 MHz, Methanol-$d_4$) δ 7.83 (d, J=8.7 Hz, 1H), 7.18-7.03 (m, 4H), 6.95 (d, J=9.2 Hz, 1H), 6.83 (d, J=2.4 Hz, 1H), 4.25 (s, 1H), 3.88 (dd, J=13.9, 4.2 Hz, 1H), 3.83-3.65 (m, 4H), 3.51-3.42 (m, 4H), 3.42-3.34 (m, 6H), 3.04-2.85 (m, 8H), 2.75-2.62 (m, 2H).

Example 60: Synthesis of methyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate

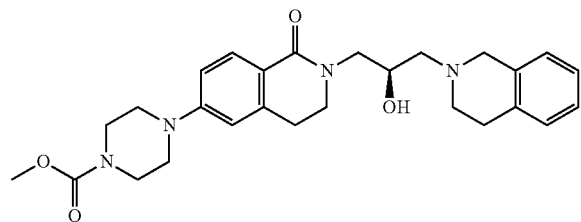 [SMILES: COC(=O)N1CCN(c2ccc3c(c2)CCN(C[C@H](O)CN2CCc4ccccc4C2)C3=O)CC1]

The title compound was synthesized in the same manner as in Example 59, except that methyl chloroformate was used instead of methanesulfonyl chloride.

$^1$H NMR (400 MHz, Methanol-$d_4$) δ 7.81 (d, J=8.7 Hz, 1H), 7.16-7.00 (m, 4H), 6.92 (dd, J=8.8, 2.5 Hz, 1H), 6.84-6.72 (m, 1H), 4.23 (tt, J=7.8, 4.5 Hz, 1H), 3.89 (dd, J=13.8, 4.2 Hz, 1H), 3.83-3.66 (m, 7H), 3.63 (t, J=5.2 Hz, 4H), 3.37 (d, J=14.3 Hz, 4H), 3.10-2.80 (m, 7H), 2.74-2.57 (m, 2H).

Example 61: Synthesis of 6-(1-acetyl-3,6-dihydro-2H-pyridin-4-yl)-2-[(2R)-3-(3,4-dihydro-1H-isoquinolin-2-yl)-2-hydroxy-propyl]-3,4-dihydroisoquinolin-1-one

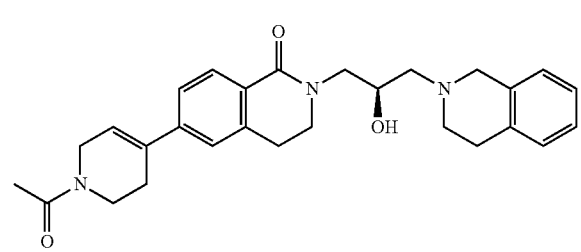 [SMILES: CC(=O)N1CC=C(c2ccc3c(c2)CCN(C[C@H](O)CN2CCc4ccccc4C2)C3=O)CC1]

2-[(2R)-3-(3,4-dihydro-1H-isoquinolin-2-yl)-2-hydroxy-propyl]-6-(1,2,3,6-tetrahydropyridin-4-yl)-3,4-dihydroisoquinolin-1-one obtained in Example 57 as a starting material was used in the same manner as in Example 59 to obtain the title compound, except that acetic anhydride was used instead of methanesulfonyl chloride.

$^1$H NMR (400 MHz, Methanol-$d_4$) δ 7.92 (d, J=8.2 Hz, 1H), 7.49-7.39 (m, 1H), 7.36 (s, 1H), 7.17-6.98 (m, 4H), 6.28 (d, J=5.0 Hz, 1H), 4.25 (td, J=7.9, 3.7 Hz, 3H), 3.92 (dd, J=13.8, 4.1 Hz, 1H), 3.86-3.67 (m, 6H), 3.39 (dd, J=13.8, 7.7 Hz, 1H), 3.05 (t, J=6.9 Hz, 2H), 2.92 (tt, J=10.5, 4.9 Hz, 4H), 2.73-2.52 (m, 4H), 2.18 (d, J=15.2 Hz, 3H).

Example 62: Synthesis of 2-[(2R)-3-(3,4-dihydro-1H-isoquinolin-2-yl)-2-hydroxy-propyl]-6-[4-(2,2,2-trifluoro acetyl)piperazin-1-yl]-3,4-dihydroisoquinolin-1-one

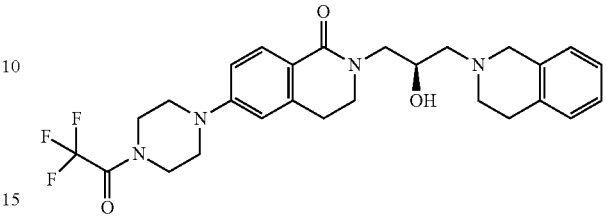

The title compound was synthesized in the same manner as in Example 59, except that trifluoroacetyl chloride was used instead of methanesulfonyl chloride.

$^1$H NMR (400 MHz, Methanol-$d_4$) δ 7.83 (d, J=8.7 Hz, 1H), 7.18-7.01 (m, 4H), 6.95 (d, J=9.1 Hz, 1H), 6.83 (s, 1H), 4.24 (d, J=4.6 Hz, 1H), 3.94-3.65 (m, 9H), 3.49-3.34 (m, 5H), 3.07-2.82 (m, 6H), 2.71-2.58 (m, 2H).

Example 63: Synthesis of tert-butyl 4-[2-[(2R)-3-(3,4-dihydro-1H-isoquinolin-2-yl)-2-hydroxy-propyl]-1-oxo-3,4-dihydroisoquinolin-6-yl]piperidine-1-carboxylate

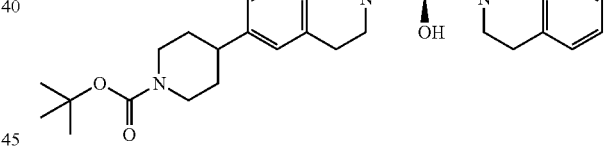

Tert-butyl 4-[2-[(2R)-3-(3,4-dihydro-1H-isoquinolin-2-yl)-2-hydroxy-propyl]-1-oxo-3,4-dihydroisoquinolin-6-yl]-3,6-dihydro-2H-pyridine-1-carboxylate (85 mg, 0.16 mmol) obtained in Example 56 was dissolved in methanol (5 mL), and palladium-charcoal was added and stirred while charging hydrogen gas. After completion of the reaction, the reaction mixture was filtered through Celite. The solvent was dried under reduced pressure, and the purification was carried out by flash chromatography to obtain 5 mg of the title compound.

$^1$H NMR (400 MHz, Methanol-$d_4$) δ 7.88 (d, J=7.9 Hz, 1H), 7.25 (d, J=7.6 Hz, 2H), 7.20-7.02 (m, 4H), 4.25 (t, J=11.9 Hz, 3H), 3.94-3.81 (m, 2H), 3.74 (tt, J=12.6, 6.5 Hz, 3H), 3.43 (td, J=13.8, 13.0, 7.9 Hz, 1H), 3.12-2.67 (m, 10H), 1.84 (d, J=13.1 Hz, 2H), 1.63 (qd, J=12.5, 4.2 Hz, 3H), 1.50 (s, 9H).

Example 64: Synthesis of [(2R)-3-(3,4-dihydro-1H-isoquinolin-2-yl)-2-hydroxy-propyl]-6-(4-isopropylpiperazin-1-yl)-3,4-dihydroisoquinolin-1-one

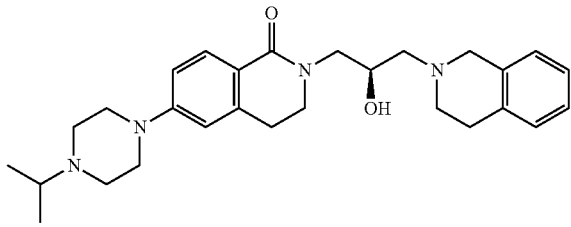 [SMILES: CC(C)N1CCN(c2ccc3c(c2)CCN(C[C@H](O)CN2CCc4ccccc4C2)C3=O)CC1]

The title compound was synthesized in the same manner as in Example 2, except that 4-isopropylpiperazine was used instead of pyrrolidine.

$^1$H NMR (400 MHz, Methanol-$d_4$) δ 7.80 (d, J=8.7 Hz, 1H), 7.17-6.99 (m, 4H), 6.95-6.86 (m, 1H), 6.78 (s, 1H), 4.25 (d, J=12.4 Hz, 1H), 3.89 (dd, J=13.8, 4.2 Hz, 1H), 3.82-3.63 (m, 4H), 3.37 (t, J=5.3 Hz, 6H), 3.05-2.82 (m, 6H), 2.78-2.69 (m, 4H), 2.65 (t, J=5.1 Hz, 2H), 1.15 (d, J=6.5 Hz, 6H).

Example 65: Synthesis of ethyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate

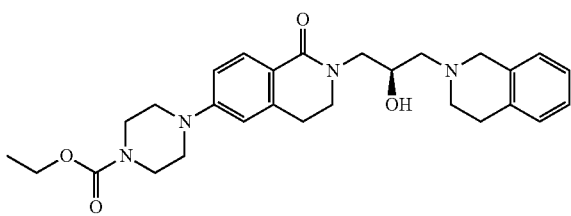 [SMILES: CCOC(=O)N1CCN(c2ccc3c(c2)CCN(C[C@H](O)CN2CCc4ccccc4C2)C3=O)CC1]

The title compound was synthesized in the same manner as in Example 2, except that ethyl piperazine-1-carboxylate was used instead of pyrrolidine.

$^1$H NMR (400 MHz, Methanol-$d_4$) δ 7.81 (d, J=8.7 Hz, 1H), 7.17-7.00 (m, 4H), 6.98-6.88 (m, 1H), 6.87-6.74 (m, 1H), 4.18 (hept, J=8.1 Hz, 3H), 3.89 (dd, J=13.8, 4.2 Hz, 1H), 3.83-3.54 (m, 7H), 3.37 (d, J=13.3 Hz, 6H), 3.05-2.76 (m, 6H), 2.64 (t, J=5.0 Hz, 2H), 1.30 (t, J=7.1 Hz, 3H).

Example 66: Synthesis of 2-[(2R)-3-(3,4-dihydro-1H-isoquinolin-2-yl)-2-hydroxy-propyl]-6-[(4-methoxy-1-piperidyl)methyl]-3,4-dihydroisoquinolin-1-one

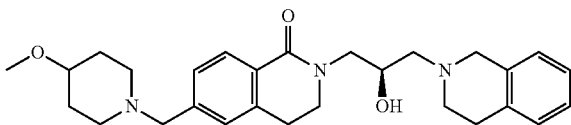 [SMILES: COC1CCN(Cc2ccc3c(c2)CCN(C[C@H](O)CN2CCc4ccccc4C2)C3=O)CC1]

The title compound was synthesized in the same manner as in Example 43, except that potassium (4-methoxy-1-piperidyl)methyltrifluoroborate was used instead of potassium (morpholin-4-yl)methyltrifluoroborate.

$^1$H NMR (400 MHz, Methanol-$d_4$) δ 7.91 (d, J=7.9 Hz, 1H), 7.33 (d, J=8.0 Hz, 1H), 7.28 (s, 1H), 7.15-7.00 (m, 4H), 4.25 (q, J=8.0, 6.7 Hz, 1H), 3.92 (dd, J=13.7, 4.2 Hz, 1H), 3.86-3.67 (m, 4H), 3.57 (s, 2H), 3.46-3.23 (m, 4H), 3.04 (t, J=6.8 Hz, 2H), 2.90 (dd, J=15.8, 5.1 Hz, 4H), 2.83-2.56 (m, 4H), 2.32-2.14 (m, 3H), 1.92 (s, 2H), 1.59 (d, J=11.1 Hz, 2H).

Example 67: Synthesis of 6-(1-acetyl-4-piperidyl)-2-[(2R)-3-(3,4-dihydro-1H-isoquinolin-2-yl)-2-hydroxy-propyl]-3,4-dihydroisoquinolin-1-one

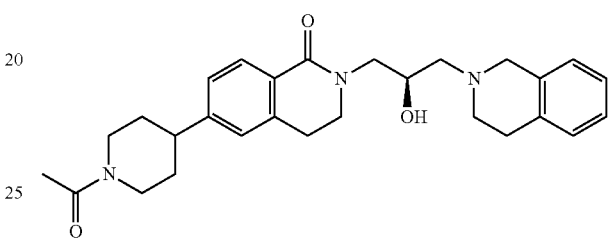

6-(1-Acetyl-3,6-dihydro-2H-pyridin-4-yl)-2-[(2R)-3-(3, 4-dihydro-1H-isoquinoline-2-yl)-2-hydroxy-propyl]-3,4-dihydroisoquinolin-1-one obtained in Example 61 as a starting material was used in the same manner as in Example 63 to obtain the title compound.

$^1$H NMR (400 MHz, Methanol-$d_4$) δ 7.89 (d, J=8.0 Hz, 1H), 7.27 (d, J=8.1 Hz, 1H), 7.19 (s, 1H), 7.14-7.02 (m, 4H), 4.78-4.60 (m, 1H), 4.25 (s, 1H), 4.07 (d, J=13.7 Hz, 1H), 3.91 (dd, J=13.9, 4.1 Hz, 1H), 3.76 (d, J=16.3 Hz, 4H), 3.39 (dd, J=13.8, 7.6 Hz, 1H), 3.31-3.20 (m, 1H), 3.03 (t, J=7.0 Hz, 2H), 2.98-2.82 (m, 4H), 2.80-2.62 (m, 3H), 2.16 (s, 3H), 2.05 (d, J=9.7 Hz, 1H), 1.98-1.81 (m, 2H), 1.68 (dqd, J=37.9, 12.7, 4.3 Hz, 2H).

Example 68: Synthesis of 6-[(4-acetylpiperazin-1-yl)methyl]-2-[(2R)-3-(3,4-dihydro-1H-isoquinolin-2-yl)-2-hydroxy-propyl]-3,4-dihydroisoquinolin-1-one

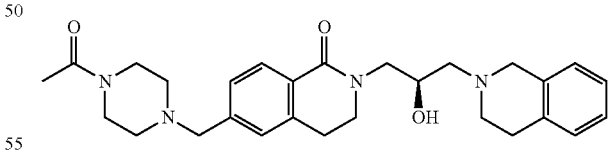

The title compound was synthesized in the same manner as in Example 43, except that potassium (4-acetylpiperazin-1-yl)methyltrifluoroborate was used instead of potassium (morpholin-4-yl)methyltrifluoroborate.

$^1$H NMR (400 MHz, Methanol-$d_4$) δ 7.92 (d, J=7.9 Hz, 1H), 7.36 (d, J=8.0 Hz, 1H), 7.30 (s, 1H), 7.17-7.02 (m, 4H), 4.27 (h, J=5.8, 4.8 Hz, 1H), 3.91 (dd, J=13.8, 4.2 Hz, 1H), 3.87-3.69 (m, 4H), 3.68-3.50 (m, 6H), 3.42 (dd, J=13.8, 7.4 Hz, 1H), 3.05 (t, J=6.9 Hz, 2H), 2.95 (s, 4H), 2.71 (h, J=7.6, 7.2 Hz, 2H), 2.48 (dt, J=20.9, 5.1 Hz, 4H), 2.10 (s, 3H).

Example 69: Synthesis of 2-[(2R)-3-(3,4-dihydro-1H-isoquinolin-2-yl)-2-hydroxy-propyl]-6-(4-propanoylpiperazin-1-yl)-3,4-dihydroisoquinolin-1-one

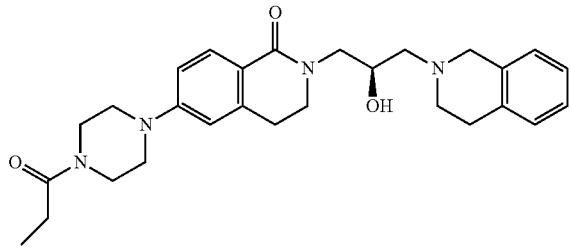 [SMILES: CCC(=O)N1CCN(c2ccc3c(c2)CCN(C[C@H](O)CN2CCc4ccccc4C2)C3=O)CC1]

The title compound was synthesized in the same manner as in Example 59, except that propionyl chloride was used instead of methanesulfonyl chloride.

¹H NMR (400 MHz, Methanol-$d_4$) δ 7.82 (d, J=8.7 Hz, 1H), 7.17-7.01 (m, 4H), 6.93 (d, J=8.8 Hz, 1H), 6.80 (s, 1H), 3.89 (dd, J=13.8, 4.2 Hz, 1H), 3.82-3.62 (m, 8H), 3.38 (dd, J=16.1, 5.9 Hz, 6H), 3.05-2.82 (m, 6H), 2.70-2.57 (m, 2H), 2.48 (q, J=7.5 Hz, 2H), 1.16 (t, J=7.5 Hz, 3H).

Example 70: Synthesis of 2-[(2R)-3-(3,4-dihydro-1H-isoquinolin-2-yl)-2-hydroxy-propyl]-6-[4-(2-methylpropanoyl)piperazin-1-yl]-3,4-dihydroisoquinolin-1-one

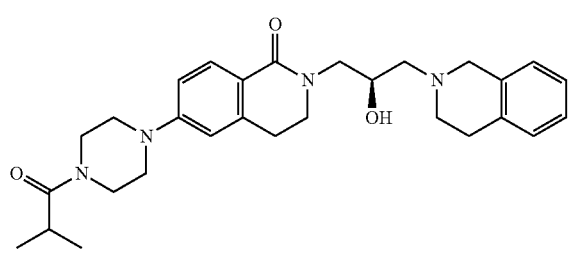 [SMILES: CC(C)C(=O)N1CCN(c2ccc3c(c2)CCN(C[C@H](O)CN2CCc4ccccc4C2)C3=O)CC1]

The title compound was synthesized in the same manner as in Example 59, except that isobutyryl chloride was used instead of methanesulfonyl chloride.

¹H NMR (400 MHz, Methanol-$d_4$) δ 7.82 (d, J=8.7 Hz, 1H), 7.19-7.00 (m, 4H), 6.91 (dd, J=8.8, 2.5 Hz, 1H), 6.79 (d, J=2.5 Hz, 1H), 4.22 (dq, J=7.9, 4.8, 3.9 Hz, 1H), 3.88 (dd, J=13.8, 4.2 Hz, 1H), 3.81-3.63 (m, 8H), 3.43-3.31 (m, 5H), 3.08-2.80 (m, 7H), 2.68-2.57 (m, 2H), 1.14 (d, J=6.6 Hz, 6H).

Example 71: Synthesis of 2-[(2R)-3-(3,4-dihydro-1H-isoquinolin-2-yl)-2-hydroxy-propyl]-6-[4-(2,2-dimethylpropanoyl)piperazin-1-yl]-3,4-dihydroisoquinolin-1-one

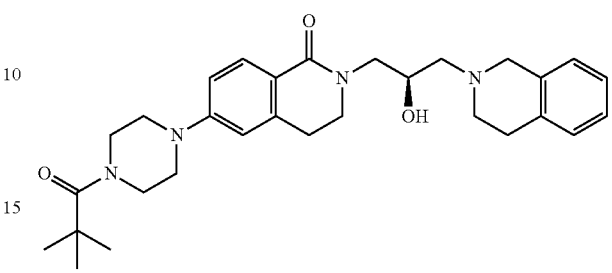

The title compound was synthesized in the same manner as in Example 59, except that pivaloyl chloride was used instead of methanesulfonyl chloride.

¹H NMR (400 MHz, Methanol-$d_4$) δ 7.70 (d, J=8.7 Hz, 1H), 7.05-6.88 (m, 4H), 6.80 (dd, J=8.9, 2.5 Hz, 1H), 6.68 (d, J=2.5 Hz, 1H), 4.11 (tt, J=7.9, 4.6 Hz, 1H), 3.82-3.68 (m, 5H), 3.68-3.51 (m, 4H), 3.23 (d, J=5.3 Hz, 5H), 2.90-2.69 (m, 6H), 2.59-2.40 (m, 2H), 1.21 (s, 9H).

Example 72: Synthesis of tert-butyl 5-[2-[(2R)-3-(3,4-dihydro-1H-isoquinolin-2-yl)-2-hydroxy-propyl]-1-oxo-3,4-dihydroisoquinolin-6-yl]-2,5-diazabicyclo[2.2.1]heptane-2-carboxylate

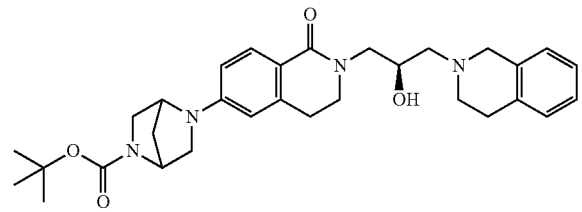 [SMILES: CC(C)(C)OC(=O)N1CC2CC1CN2c1ccc2c(c1)CCN(C[C@H](O)CN1CCc3ccccc3C1)C2=O]

The title compound was synthesized in the same manner as in Example 2, except that tert-butyl 2,5-diazabicyclo[2.2.1]heptane-2-carboxylate was used instead of pyrrolidine.

¹H NMR (400 MHz, Methanol-$d_4$) δ 7.78 (d, J=8.6 Hz, 1H), 7.18-6.97 (m, 4H), 6.57 (d, J=8.7 Hz, 1H), 6.49-6.36 (m, 1H), 4.60 (d, J=16.3 Hz, 2H), 4.22 (dt, J=8.0, 4.9 Hz, 1H), 3.88 (dd, J=13.8, 4.2 Hz, 1H), 3.79-3.57 (m, 5H), 3.48-3.35 (m, 3H), 3.20 (t, J=8.5 Hz, 1H), 3.02-2.79 (m, 6H), 2.64 (t, J=5.4 Hz, 2H), 2.07-1.95 (m, 2H), 1.45 (d, J=24.1 Hz, 9H).

Example 73: Synthesis of 2-[(2R)-3-(3,4-dihydro-1H-isoquinolin-2-yl)-2-hydroxy-propyl]-6-(2-oxa-5-azabicyclo[2.2.1]heptan-5-yl)-3,4-dihydroisoquinolin-1-one

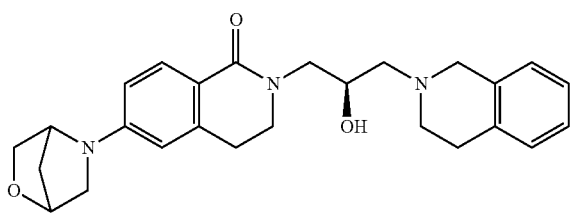 [SMILES: O=C1c2ccc(N3CC4CC3CO4)cc2CCN1C[C@H](O)CN1CCc2ccccc2C1]

The title compound was synthesized in the same manner as in Example 2, except that 2-oxa-5-azabicyclo[2.2.1]heptane was used instead of pyrrolidine.

$^1$H NMR (400 MHz, Methanol-$d_4$) δ 7.78 (d, J=8.6 Hz, 1H), 7.30-6.99 (m, 4H), 6.65-6.50 (m, 1H), 6.46 (s, 1H), 4.68 (d, J=20.8 Hz, 2H), 4.25 (s, 1H), 3.93-3.80 (m, 4H), 3.72 (tp, J=12.6, 6.6 Hz, 2H), 3.58 (d, J=9.6 Hz, 1H), 3.43-3.35 (m, 3H), 3.19 (d, J=9.7 Hz, 1H), 2.96 (s, 5H), 2.72 (t, J=5.7 Hz, 2H), 2.02 (q, J=10.0 Hz, 3H).

Example 74: Synthesis of 2-[(2R)-3-(3,4-dihydro-1H-isoquinolin-2-yl)-2-hydroxy-propyl]-6-hydroxy-3,4-dihydroisoquinolin-1-one

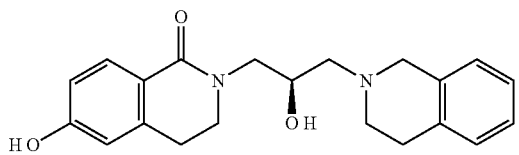

6-Bromo-2-[(2R)-3-(3,4-dihydro-1H-isoquinolin-2-yl)-2-hydroxy-propyl]-3,4-dihydroisoquinolin-1-one (543 mg, 1.31 mmol) obtained in Example 1, KOH (293 mg, 5.23 mmol), t-BuXPhos (56 mg, 0.13 mmol) and Pd(dba)$_2$ (38 mg, 0.07 mmol) were put into a microwave container together with 7 mL of 1,4-dioxane:H$_2$O (1:1) solution, and heated and stirred at 100° C. for 2 hours. After adding ethyl acetate, the reaction mixture was acidified with 2 N hydrochloric acid. The obtained aqueous layer was basified with a saturated K$_2$CO$_3$ solution, and then extracted with ethyl acetate. The organic layer was dried over anhydrous magnesium sulfate, the solvent was removed by evaporation under reduced pressure, and then used in the next reaction without further purification (product: 300 mg).

$^1$H NMR (400 MHz, Methanol-$d_4$) δ 7.80 (d, J=8.5 Hz, 1H), 7.23-7.05 (m, 4H), 6.78-6.71 (m, 1H), 6.65 (s, 1H), 4.30 (t, J=6.0 Hz, 1H), 3.99 (s, 2H), 3.85 (dd, J=13.9, 4.4 Hz, 1H), 3.73 (dtd, J=16.8, 11.6, 10.5, 5.7 Hz, 2H), 3.43 (dd, J=13.9, 7.1 Hz, 1H), 3.19-2.92 (m, 6H), 2.92-2.77 (m, 2H).

Example 75: Synthesis of 2-chloro-6-[(2R)-3-(3,4-dihydro-1H-isoquinolin-2-yl)-2-hydroxy-propyl]-7,8-dihydro-1,6-naphthyridin-5-one

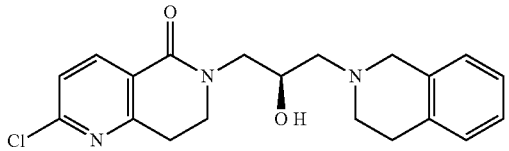

The title compound was synthesized in the same manner as in Example 1, except that 2-chloro-7,8-dihydro-6H-1,6-naphthyridin-5-one was used instead of 6-bromo-3,4-dihydro-2H-isoquinolin-1-one.

$^1$H NMR (400 MHz, Methanol-$d_4$) δ 8.23 (d, J=8.2 Hz, 1H), 7.43 (d, J=8.2 Hz, 1H), 7.15-6.99 (m, 4H), 4.24 (qt, J=12.3, 6.0 Hz, 1H), 3.93-3.70 (m, 5H), 3.41 (dd, J=13.8, 7.8 Hz, 1H), 3.16 (t, J=6.8 Hz, 2H), 2.91 (tt, J=10.1, 4.6 Hz, 4H), 2.72-2.59 (m, 2H).

Example 76: Synthesis of 6-(2,5-diazabicyclo[2.2.1]heptan-2-yl)-2-[(2R)-3-(3,4-dihydro-1H-isoquinolin-2-yl)-2-hydroxy-propyl]-3,4-dihydroisoquinolin-1-one

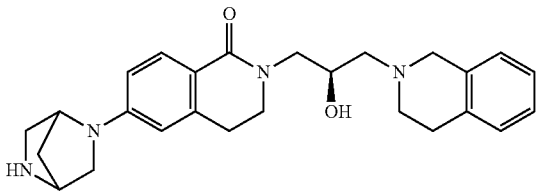 [SMILES: O=C1c2ccc(N3CC4CC3CN4)cc2CCN1C[C@H](O)CN1CCc2ccccc2C1]

Tert-butyl 5-[2-[(2R)-3-(3,4-dihydro-1H-isoquinolin-2-yl)-2-hydroxy-propyl]-1-oxo-3,4-dihydroisoquinolin-6-yl]-2,5-diazabicyclo[2.2.1]heptane-2-carboxylate obtained in Example 72 as a starting material was used in the same manner as in Example 57 to obtain the title compound.

$^1$H NMR (400 MHz, Methanol-$d_4$) δ 7.79 (d, J=8.6 Hz, 1H), 7.31-7.01 (m, 4H), 6.60 (d, J=8.8 Hz, 1H), 6.52-6.37 (m, 1H), 4.71 (d, J=22.1 Hz, 2H), 4.26 (s, 1H), 3.86 (t, J=6.1 Hz, 2H), 3.81-3.42 (m, 5H), 2.98 (s, 5H), 2.75 (q, J=7.1, 6.0 Hz, 2H), 2.27-1.91 (m, 6H).

Example 77: Synthesis of 2-[(2R)-3-(3,4-dihydro-1H-isoquinolin-2-yl)-2-hydroxy-propyl]-6-(3-piperidylamino)-3,4-dihydroisoquinolin-1-one

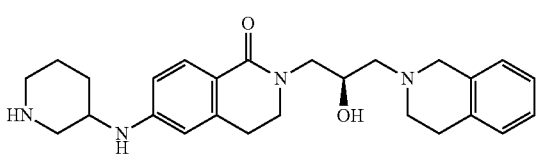 [SMILES: O=C1c2ccc(NC3CCCNC3)cc2CCN1C[C@H](O)CN1CCc2ccccc2C1]

Example 77-1: Synthesis of tert-butyl 3-[[2-[(2R)-3-(3,4-dihydro-1H-isoquinolin-2-yl)-2-hydroxy-propyl]-1-oxo-3,4-dihydroisoquinolin-6-yl]amino]piperidine-1-carboxylate The title compound was synthesized in the same manner as in Example 2, except that tert-butyl 3-aminopiperidine-1-carboxylate was used instead of pyrrolidine.

Example 77-2: Synthesis of 2-[(2R)-3-(3,4-dihydro-1H-isoquinolin-2-yl)-2-hydroxy-propyl]-6-(3-piperidylamino)-3,4-dihydroisoquinolin-1-one Tert-butyl 3-[[2-[(2R)-3-(3,4-dihydro-1H-isoquinolin-2-yl)-2-hydroxy-propyl]-1-oxo-3,4-dihydroisoquinolin-6-yl]amino]piperidine-1-carboxylate obtained in Example 77-1 as a starting material was used in the same manner as in Example 57 to obtain the title compound.

$^1$H NMR (400 MHz, Methanol-$d_4$) δ 7.70 (d, J=8.6 Hz, 1H), 7.19-6.97 (m, 4H), 6.57 (dd, J=8.6, 2.3 Hz, 1H), 6.44 (s, 1H), 4.21 (tt, J=7.9, 4.6 Hz, 1H), 3.86 (dd, J=13.8, 4.2 Hz, 1H), 3.79-3.58 (m, 4H), 3.50 (td, J=9.4, 4.6 Hz, 1H), 3.38-3.30 (m, 1H), 3.26 (d, J=3.7 Hz, 1H), 3.01 (dt, J=13.0, 4.0 Hz, 1H), 2.88 (dt, J=18.9, 6.1 Hz, 6H), 2.65 (td, J=9.8, 8.7, 3.8 Hz, 3H), 2.46 (dd, J=12.2, 9.4 Hz, 1H), 2.12-2.01 (m, 1H), 1.84 (dt, J=13.5, 4.0 Hz, 1H), 1.66 (ddt, J=21.0, 14.0, 7.0 Hz, 1H), 1.54-1.39 (m, 1H).

Example 78: Synthesis of tert-butyl 4-[2-[(2R)-3-(3,4-dihydro-1H-isoquinolin-2-yl)-2-hydroxy-propyl]-1-oxo-3,4-dihydroisoquinolin-6-yl]-1,4-diazepane-1-carboxylate

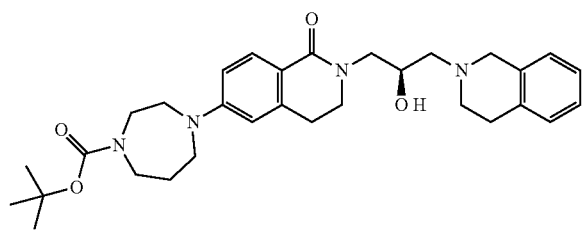

The title compound was synthesized in the same manner as in Example 2, except that tert-butyl 1,4-diazepane-1-carboxylate was used instead of pyrrolidine.

$^1$H NMR (400 MHz, Methanol-$d_4$) δ 7.77 (d, J=8.8 Hz, 1H), 7.16-6.98 (m, 4H), 6.73 (d, J=8.8 Hz, 1H), 6.59 (s, 1H), 4.28-4.09 (m, 1H), 3.87 (dd, J=13.8, 4.3 Hz, 1H), 3.79-3.57 (m, 9H), 3.37 (d, J=6.4 Hz, 4H), 3.03-2.78 (m, 6H), 2.73-2.55 (m, 2H), 1.95 (dq, J=19.3, 6.2 Hz, 2H), 1.34 (d, J=44.1 Hz, 9H).

Example 79: Synthesis of 2-[(2R)-3-(3,4-dihydro-1H-isoquinolin-2-yl)-2-hydroxy-propyl]-6-(4-methyl-3-oxo-1,4-diazepan-1-yl)-3,4-dihydroisoquinolin-1-one

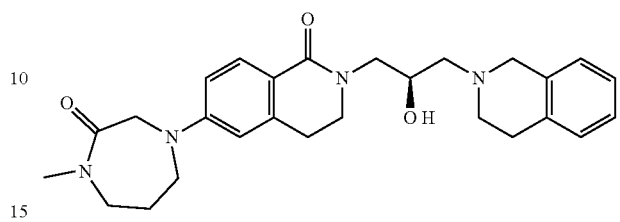

The title compound was synthesized in the same manner as in Example 2, except that 1-methyl-1,4-diazepan-2-one was used instead of pyrrolidine.

$^1$H NMR (400 MHz, Methanol-$d_4$) δ 7.78 (d, J=8.7 Hz, 1H), 7.17-6.98 (m, 4H), 6.84 (dd, J=8.9, 2.6 Hz, 1H), 6.72 (d, J=2.5 Hz, 1H), 4.25 (d, J=22.5 Hz, 3H), 3.87 (dd, J=13.8, 4.3 Hz, 1H), 3.82-3.62 (m, 6H), 3.62-3.53 (m, 2H), 3.39-3.31 (m, 1H), 2.93 (d, J=17.9 Hz, 7H), 2.86 (t, J=5.8 Hz, 2H), 2.70-2.56 (m, 2H), 1.90 (p, J=5.3 Hz, 2H).

Example 80: Synthesis of 6-(4-acetyl-1,4-diazepan-1-yl)-2-[(2R)-3-(3,4-dihydro-1H-isoquinolin-2-yl)-2-hydroxy-propyl]-3,4-dihydroisoquinolin-1-one

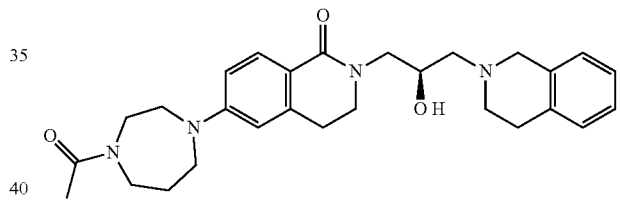

Example 80-1: Synthesis of 6-(1,4-diazepan-1-yl)-2-[(2R)-3-(3,4-dihydro-1H-isoquinolin-2-yl)-2-hydroxy-propyl]-3,4-dihydroisoquinolin-1-one Tert-butyl 4-[2-[(2R)-3-(3,4-dihydro-1H-isoquinolin-2-yl)-2-hydroxy-propyl]-1-oxo-3,4-dihydroisoquinolin-6-yl]-1,4-diazepane-1-carboxylate obtained in Example 78 as a starting material was used in the same manner as in Example 57 to obtain the title compound.

Example 80-2: Synthesis of 6-(4-acetyl-1,4-diazepan-1-yl)-2-[(2R)-3-(3,4-dihydro-1H-isoquinolin-2-yl)-2-hydroxy-propyl]-3,4-dihydroisoquinolin-1-one 6-(1,4-Diazepan-1-yl)-2-[(2R)-3-(3,4-dihydro-1H-isoquinolin-2-yl)-2-hydroxy-propyl]-3,4-dihydroisoquinolin-1-one obtained in Example 80-1 as a starting material was used in the same manner as in Example 59 to obtain the title compound, except that acetic anhydride was used instead of methanesulfonyl chloride.

$^1$H NMR (400 MHz, Methanol-$d_4$) δ 7.78 (dd, J=8.8, 4.3 Hz, 1H), 7.17-7.00 (m, 4H), 6.75 (t, J=7.3 Hz, 1H), 6.66-6.53 (m, 1H), 4.22 (dt, J=8.2, 5.2 Hz, 1H), 3.93-3.61 (m, 11H), 3.49 (q, J=5.2, 4.8 Hz, 2H), 3.41-3.34 (m, 1H), 2.93 (ddt, J=20.0, 10.9, 6.8 Hz, 6H), 2.72-2.56 (m, 2H), 2.15-1.87 (m, 5H).

Example 81: Synthesis of 6-(5-acetyl-2,5-diazabicyclo[2.2.1]heptan-2-yl)-2-[(2R)-3-(3,4-dihydro-1H-isoquinolin-2-yl)-2-hydroxy-propyl]-3,4-dihydroisoquinolin-1-one

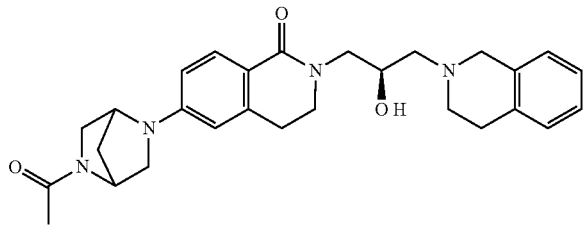

6-(2,5-Diazabicyclo[2.2.1]heptan-2-yl)-2-[(2R)-3-(3,4-dihydro-1H-isoquinoline-2-yl)-2-hydroxy-propyl]-3,4-dihydroisoquinolin-1-one obtained in Example 76 as a starting material was used in the same manner as in Example 59 to obtain the title compound, except that acetic anhydride was used instead of methanesulfonyl chloride.

$^1$H NMR (400 MHz, Methanol-d$_4$) δ 7.78 (d, J=8.6 Hz, 1H), 7.22-7.04 (m, 4H), 6.59 (d, J=8.7 Hz, 1H), 6.52-6.41 (m, 1H), 4.70 (d, J=22.3 Hz, 2H), 4.29 (q, J=6.1, 5.5 Hz, 1H), 3.97 (s, 2H), 3.85 (dd, J=13.8, 4.4 Hz, 1H), 3.80-3.50 (m, 4H), 3.49-3.36 (m, 2H), 3.25 (dd, J=29.9, 9.3 Hz, 1H), 3.14-2.92 (m, 6H), 2.83 (d, J=8.0 Hz, 2H), 2.23-1.89 (m, 5H).

Example 82: Synthesis of 6-(4-acetyl-4,7-diazaspiro[2.5]octan-7-yl)-2-[(2R)-3-(3,4-dihydro-1H-isoquinolin-2-yl)-2-hydroxy-propyl]-3,4-dihydroisoquinolin-1-one

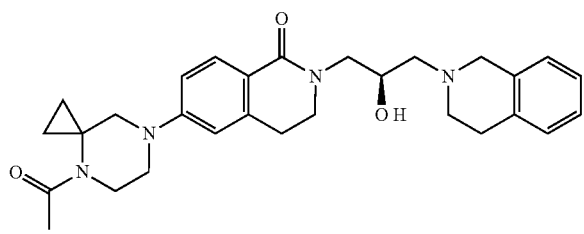

The title compound was synthesized in the same manner as in Example 2, except that 1-(4,7-diazaspiro[2.5]octan-4-yl)ethanone was used instead of pyrrolidine.

$^1$H NMR (400 MHz, Methanol-d$_4$) δ 7.80 (d, J=8.7 Hz, 1H), 7.17-7.00 (m, 4H), 6.94-6.83 (m, 1H), 6.74 (s, 1H), 4.32-4.13 (m, 1H), 3.98-3.61 (m, 7H), 3.47-3.34 (m, 3H), 3.21 (d, J=18.2 Hz, 2H), 3.03-2.76 (m, 6H), 2.70-2.55 (m, 2H), 2.19 (d, J=47.0 Hz, 3H), 1.26-1.05 (m, 4H).

Example 83: Synthesis of 6-[(1-acetyl-4-piperidyl)methoxy]-2-[(2R)-3-(3,4-dihydro-1H-isoquinolin-2-yl)-2-hydroxy-propyl]-3,4-dihydroisoquinolin-1-one

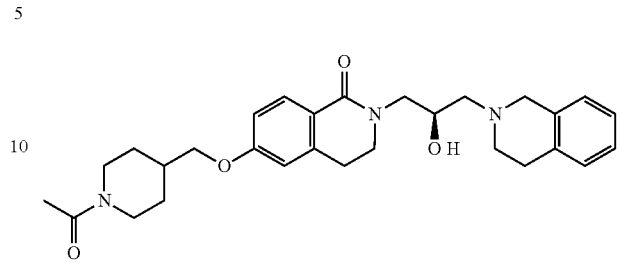

2-[(2R)-3-(3,4-dihydro-1H-isoquinolin-2-yl)-2-hydroxy-propyl]-6-hydroxy-3,4-dihydroisoquinolin-1-one (50 mg, 0.14 mmol) obtained in Example 74, (1-acetyl-4-piperidyl)methyl methanesulfonate (60 mg, 0.28 mmol) and Cs$_2$CO$_3$ (140 mg, 0.42 mmol) were dissolved in acetonitrile (4 mL) and stirred at 150° C. in a microwave tube. The reaction mixture was diluted with ethyl acetate, filtered through Celite. The solvent was dried under reduced pressure, and the purification was carried out by flash chromatography to obtain 27 mg of the title compound.

$^1$H NMR (400 MHz, Methanol-d$_4$) δ 7.88 (d, J=8.7 Hz, 1H), 7.17-6.98 (m, 4H), 6.90 (d, J=8.8 Hz, 1H), 6.82 (s, 1H), 4.59 (d, J=13.2 Hz, 1H), 4.24 (d, J=6.8 Hz, 1H), 4.07-3.84 (m, 4H), 3.84-3.63 (m, 4H), 3.42-3.34 (m, 1H), 3.18 (t, J=12.6 Hz, 1H), 3.07-2.79 (m, 6H), 2.78-2.58 (m, 3H), 2.13 (s, 3H), 1.92 (dd, J=25.6, 13.3 Hz, 2H), 1.47-1.19 (m, 3H).

Example 84: Synthesis of 2-[(2R)-3-(3,4-dihydro-1H-isoquinolin-2-yl)-2-hydroxy-propyl]-6-(4-methyl-5-oxo-1,4-diazepan-1-yl)-3,4-dihydroisoquinolin-1-one

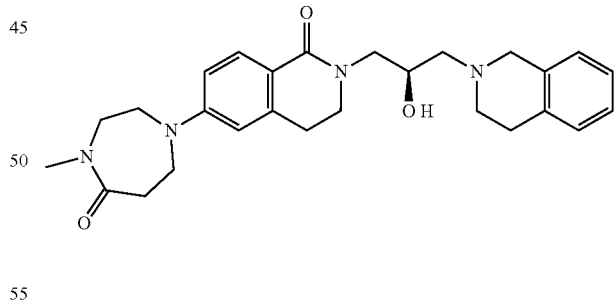

The title compound was synthesized in the same manner as in Example 2, except that 4-methyl-1,4-diazepan-5-one was used instead of pyrrolidine.

$^1$H NMR (400 MHz, Methanol-d$_4$) δ 7.80 (d, J=8.7 Hz, 1H), 7.18-6.99 (m, 4H), 6.86 (d, J=9.1 Hz, 1H), 6.73 (d, J=2.5 Hz, 1H), 4.22 (d, J=7.1 Hz, 1H), 3.88 (dd, J=13.8, 4.2 Hz, 1H), 3.80-3.71 (m, 3H), 3.67 (q, J=7.7, 7.0 Hz, 6H), 3.37 (d, J=7.4 Hz, 2H), 3.04-2.90 (m, 7H), 2.87 (d, J=5.4 Hz, 2H), 2.81 (t, J=5.6 Hz, 2H), 2.64 (t, J=5.2 Hz, 2H).

Example 85: Synthesis of 2-[(2R)-3-(3,4-dihydro-1H-isoquinolin-2-yl)-2-hydroxy-propyl]-6-(4-isopropyl-3-oxo-piperazin-1-yl)-3,4-dihydroisoquinolin-1-one

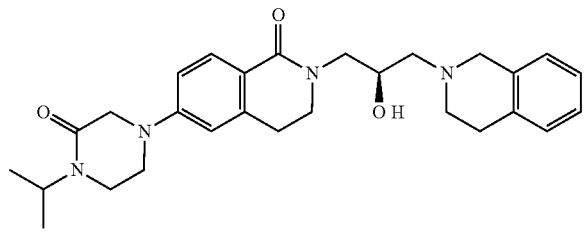

The title compound was synthesized in the same manner as in Example 2, except that 1-isopropylpiperazin-2-one was used instead of pyrrolidine.

$^1$H NMR (400 MHz, Methanol-$d_4$) δ 7.84 (d, J=8.7 Hz, 1H), 7.17-6.97 (m, 4H), 6.90-6.81 (m, 1H), 6.72 (s, 1H), 4.81 (p, J=6.8 Hz, 1H), 4.31-4.18 (m, 1H), 3.99 (s, 2H), 3.89 (dd, J=13.8, 4.2 Hz, 1H), 3.81-3.65 (m, 4H), 3.62 (t, J=5.3 Hz, 2H), 3.49 (t, J=5.2 Hz, 2H), 3.39 (t, J=9.6 Hz, 1H), 3.05-2.80 (m, 6H), 2.71-2.59 (m, 2H), 1.21 (d, J=6.8 Hz, 6H).

Example 86: Synthesis of 6-(4-acetyl-2-oxo-piperazin-1-yl)-2-[(2R)-3-(3,4-dihydro-1H-isoquinolin-2-yl)-2-hydroxy-propyl]-3,4-dihydroisoquinolin-1-one

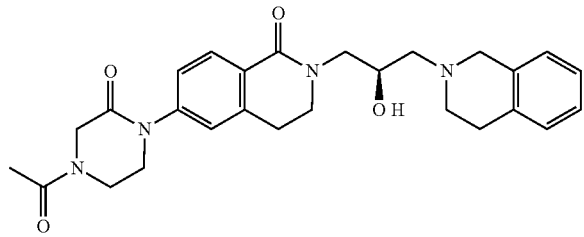

The title compound was synthesized in the same manner as in Example 18, except that 4-acetylpiperazin-2-one was used instead of pyrrolidin-2-one.

$^1$H NMR (400 MHz, Methanol-$d_4$) δ 8.01 (d, J=8.3 Hz, 1H), 7.35 (d, J=17.4 Hz, 2H), 7.16-7.00 (m, 4H), 4.37 (d, J=18.9 Hz, 2H), 4.26 (s, 1H), 4.04-3.87 (m, 4H), 3.87-3.68 (m, 4H), 3.40 (dd, J=13.7, 7.8 Hz, 2H), 3.11-2.99 (m, 2H), 2.92 (dd, J=13.3, 4.8 Hz, 4H), 2.73-2.62 (m, 2H), 2.20 (d, J=8.6 Hz, 3H).

Example 87: Synthesis of 4-[2-[(2R)-3-(3,4-dihydro-1H-isoquinolin-2-yl)-2-hydroxy-propyl]-1-oxo-3,4-dihydroisoquinolin-6-yl]piperazine-1-carbaldehyde The title compound was synthesized in the same manner as in Example 2, except that piperazine-1-carbaldehyde was used instead of pyrrolidine.

$^1$H NMR (400 MHz, Methanol-$d_4$) δ 8.12 (s, 1H), 7.82 (d, J=8.7 Hz, 1H), 7.19-7.01 (m, 4H), 6.94 (dd, J=8.8, 2.4 Hz, 1H), 6.82 (s, 1H), 4.22 (dt, J=8.1, 5.0 Hz, 1H), 3.88 (dd, J=13.8, 4.2 Hz, 1H), 3.82-3.64 (m, 6H), 3.64-3.55 (m, 2H), 3.43-3.34 (m, 5H), 3.04-2.83 (m, 6H), 2.75-2.55 (m, 2H).

Example 88: Synthesis of 2-(4-acetylpiperazin-1-yl)-6-[(2R)-3-(3,4-dihydro-1H-isoquinolin-2-yl)-2-hydroxy-propyl]-7,8-dihydro-1,6-naphthyridin-5-one

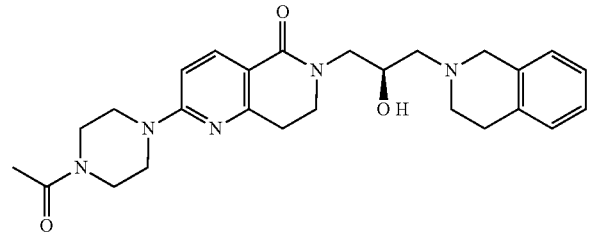

2-Chloro-6-[(2R)-3-(3,4-dihydro-1H-isoquinolin-2-yl)-2-hydroxy-propyl]-7,8-dihydro-1,6-naphthyridin-5-one (100 mg, 0.27 mmol) obtained in Example 75 and N-acetylpiperazine (100 μL, 1.08 mmol) were dissolved in ethanol and stirred at 110° C. in a microwave tube. The reaction mixture was dried under reduced pressure and purified by flash chromatography to obtain 41 mg of the title compound.

$^1$H NMR (400 MHz, Methanol-$d_4$) δ 8.00 (d, J=8.9 Hz, 1H), 7.17-6.95 (m, 4H), 6.76 (d, J=9.0 Hz, 1H), 4.22 (tt, J=7.8, 4.6 Hz, 1H), 3.94-3.61 (m, 10H), 3.42-3.34 (m, 1H), 3.05-2.80 (m, 6H), 2.71-2.54 (m, 2H), 2.17 (s, 3H).

Example 89: Synthesis of 6-[(2R)-3-(3,4-dihydro-1H-isoquinolin-2-yl)-2-hydroxy-propyl]-2-morpholino-7,8-dihydro-1,6-naphthyridin-5-one

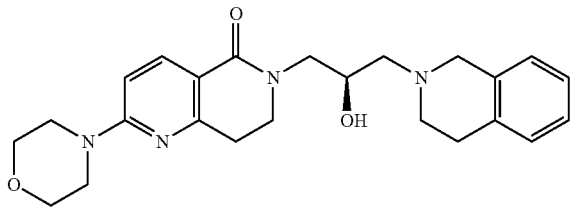 [SMILES: O=C1c2ccc(N3CCOCC3)nc2CCN1C[C@H](O)CN1CCc2ccccc2C1]

The title compound was synthesized in the same manner as in Example 88, except that morpholine was used instead of N-acetylpiperazine.

$^1$H NMR (400 MHz, Methanol-$d_4$) δ 7.99 (d, J=8.8 Hz, 1H), 7.16-7.00 (m, 4H), 6.72 (d, J=9.0 Hz, 1H), 4.21 (dq, J=7.9, 4.8, 3.9 Hz, 1H), 3.91-3.58 (m, 10H), 3.42-3.33 (m, 1H), 3.04-2.80 (m, 6H), 2.68-2.57 (m, 2H).

Example 90: Synthesis of N-[1-[2-[(2R)-3-(3,4-dihydro-1H-isoquinolin-2-yl)-2-hydroxy-propyl]-1-oxo-3,4-dihydroisoquinolin-6-yl]-4-piperidyl]-N-methyl-acetamide

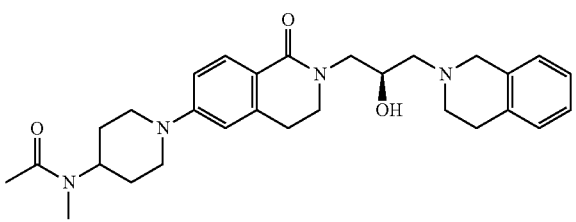 [SMILES: CC(=O)N(C)C1CCN(c2ccc3c(c2)CCN(C[C@H](O)CN2CCc4ccccc4C2)C3=O)CC1]

The title compound was synthesized in the same manner as in Example 2, except that N-methyl-N-(4-piperidyl)acetamide was used instead of pyrrolidine 1H NMR (400 MHz, Methanol-$d_4$) δ 7.82-7.73 (m, 1H), 7.17-6.99 (m, 4H), 6.92 (d, J=8.9 Hz, 1H), 6.79 (d, J=3.7 Hz, 1H), 4.60 (t, J=12.4 Hz, 1H), 4.23 (s, 1H), 4.03 (d, J=12.4 Hz, 2H), 3.88 (dd, J=13.9, 4.2 Hz, 1H), 3.81-3.62 (m, 4H), 3.41-3.35 (m, 1H), 3.05-2.76 (m, 10H), 2.64 (d, J=7.4 Hz, 2H), 2.17 (d, J=33.1 Hz, 3H), 2.07-1.62 (m, 5H).

Example 91: Synthesis of 2-[(2R)-3-(3,4-dihydro-1H-isoquinolin-2-yl)-2-hydroxy-propyl]-6-tetrahydropyran-4-yloxy-3,4-dihydroisoquinolin-1-one

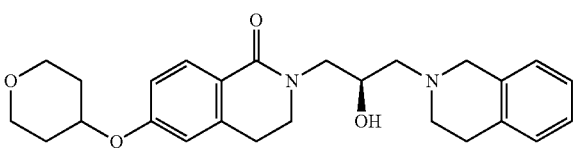 [SMILES: O=C1c2ccc(OC3CCOCC3)cc2CCN1C[C@H](O)CN1CCc2ccccc2C1]

The title compound was synthesized in the same manner as in Example 83, except that 4-bromotetrahydropyran was used instead of (1-acetyl-4-piperidyl)methyl methanesulfonate.

$^1$H NMR (400 MHz, Methanol-$d_4$) δ 7.88 (d, J=8.6 Hz, 1H), 7.17-7.01 (m, 4H), 6.92 (d, J=8.7 Hz, 1H), 6.84 (s, 1H), 4.68 (tt, J=8.4, 4.0 Hz, 1H), 4.23 (q, J=5.7, 5.1 Hz, 1H), 3.92 (ddd, J=29.3, 12.9, 5.2 Hz, 3H), 3.84-3.55 (m, 6H), 3.37 (dd, J=13.7, 7.4 Hz, 1H), 3.07-2.82 (m, 6H), 2.77-2.56 (m, 2H), 2.06 (dq, J=12.5, 3.9 Hz, 2H), 1.74 (dtd, J=12.7, 8.4, 3.7 Hz, 2H).

Example 92: Synthesis of N-[1-[2-[(2R)-3-(3,4-dihydro-1H-isoquinolin-2-yl)-2-hydroxy-propyl]-1-oxo-3,4-dihydroisoquinolin-6-yl]-4-piperidyl]acetamide

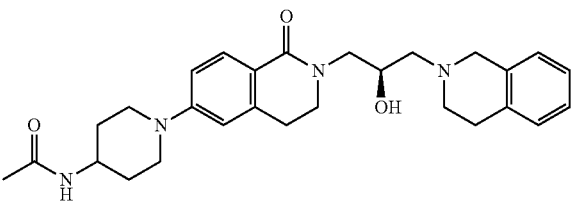 [SMILES: CC(=O)NC1CCN(c2ccc3c(c2)CCN(C[C@H](O)CN2CCc4ccccc4C2)C3=O)CC1]

The title compound was synthesized in the same manner as in Example 2, except that N-(4-piperidyl)acetamide was used instead of pyrrolidine.

$^1$H NMR (400 MHz, Methanol-$d_4$) δ 7.78 (d, J=8.7 Hz, 1H), 7.23-7.04 (m, 4H), 6.93-6.82 (m, 1H), 6.77 (s, 1H), 4.30 (tt, J=8.2, 4.6 Hz, 1H), 4.00 (s, 2H), 3.95-3.79 (m, 4H), 3.72 (dp, J=17.8, 6.2 Hz, 2H), 3.43 (dd, J=13.9, 6.9 Hz, 1H), 3.12 (t, J=6.2 Hz, 2H), 3.07-2.76 (m, 8H), 1.95 (s, 5H), 1.55 (qd, J=11.8, 3.8 Hz, 2H).

Example 93: Synthesis of 6-[(1-acetyl-3-piperidyl)amino]-2-[(2R)-3-(3,4-dihydro-1H-isoquinolin-2-yl)-2-hydroxy-propyl]-3,4-dihydroisoquinolin-1-one

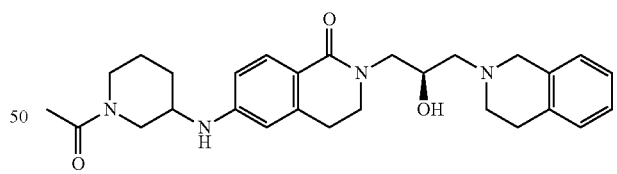

2-[(2R)-3-(3,4-dihydro-1H-isoquinolin-2-yl)-2-hydroxy-propyl]-6-(3-piperidylamino) 3,4-dihydroisoquinolin-1-one obtained in Example 77 as a starting material was used in the same manner as in Example 59 to obtain the title compound, except that acetic anhydride was used instead of methanesulfonyl chloride.

$^1$H NMR (400 MHz, Methanol-$d_4$) δ 7.71 (dd, J=12.4, 8.6 Hz, 1H), 7.22-6.99 (m, 4H), 6.61 (t, J=10.1 Hz, 1H), 6.49 (d, J=6.4 Hz, 1H), 4.22 (t, J=6.2 Hz, 1H), 3.93-3.56 (m, 7H), 3.45-3.13 (m, 4H), 3.02-2.82 (m, 6H), 2.64 (dt, J=19.5, 6.0 Hz, 2H), 2.21-1.97 (m, 3H), 1.92-1.47 (m, 4H).

Example 94: Synthesis of 7-[2-[(2R)-3-(3,4-di-hydro-1H-isoquinolin-2-yl)-2-hydroxy-propyl]-1-oxo-3,4-dihydroisoquinolin-6-yl]-5,6,8,8a-tetra-hydro-1H-oxazolo[3,4-a]pyrazin-3-one

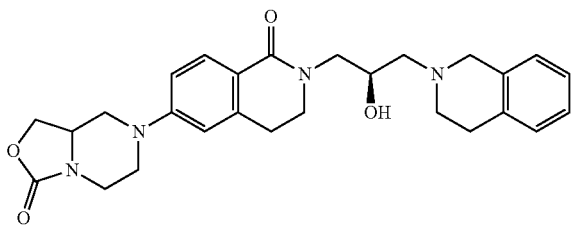 [SMILES: O=C1c2ccc(N3CCN4C(=O)OCC4C3)cc2CCN1C[C@H](O)CN1CCc2ccccc2C1]

The title compound was synthesized in the same manner as in Example 2, except that 1,5,6,7,8,8a-hexahydrooxazolo[3,4-a]pyrazin-3-one was used instead of pyrrolidine.

$^1$H NMR (400 MHz, Methanol-$d_4$) δ 7.82 (d, J=8.7 Hz, 1H), 7.17-7.04 (m, 4H), 6.95 (d, J=8.7 Hz, 1H), 6.84 (s, 1H), 4.52 (t, J=8.4 Hz, 1H), 4.25 (dt, J=7.7, 4.8 Hz, 1H), 4.16-3.98 (m, 3H), 3.87 (q, J=14.1 Hz, 4H), 3.73 (dtd, J=19.2, 12.7, 5.3 Hz, 3H), 3.39 (dd, J=13.9, 7.3 Hz, 1H), 3.23 (td, J=12.7, 3.7 Hz, 1H), 3.05-2.66 (m, 10H).

Example 95: Synthesis of 6-[(1-acetyl-4-piperidyl)oxy]-2-[(2R)-3-(3,4-dihydro-1H-isoquinolin-2-yl)-2-hydroxy-propyl]-3,4-dihydroisoquinolin-1-one

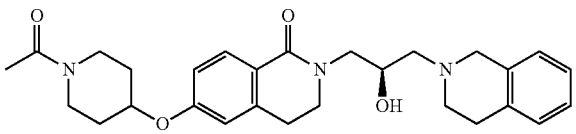 [SMILES: CC(=O)N1CCC(Oc2ccc3c(c2)CCN(C[C@H](O)CN2CCc4ccccc4C2)C3=O)CC1]

The title compound was synthesized in the same manner as in Example 83, except that (1-acetyl-4-piperidyl) methanesulfonate was used instead of (1-acetyl-4-piperidyl) methyl methanesulfonate.

$^1$H NMR (400 MHz, Methanol-$d_4$) δ 7.89 (d, J=8.6 Hz, 1H), 7.17-7.01 (m, 4H), 6.94 (d, J=8.8 Hz, 1H), 6.86 (s, 1H), 4.75 (dt, J=7.7, 3.7 Hz, 1H), 4.23 (p, J=6.9, 6.4 Hz, 1H), 3.96-3.65 (m, 7H), 3.63-3.46 (m, 2H), 3.43-3.34 (m, 1H), 3.08-2.77 (m, 6H), 2.72-2.54 (m, 2H), 2.14 (s, 3H), 2.10-1.92 (m, 2H), 1.89-1.65 (m, 2H).

Example 96: Synthesis of 6-(1-acetylazetidin-3-yl)oxy-2-[(2R)-3-(3,4-dihydro-1H-isoquinolin-2-yl)-2-hydroxy-propyl]-3,4-dihydroisoquinolin-1-one

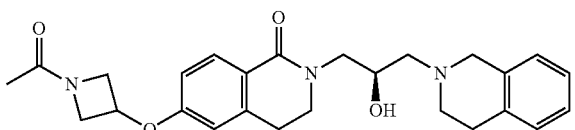

Example 96-1: Synthesis of tert-butyl 3-[[2-[(2R)-3-(3,4-dihydro-1H-isoquinolin-2-yl)-2-hydroxy-propyl]-1-oxo-3,4-dihydroisoquinolin-6-yl]oxy]azetidine-1-carboxylate The title compound was synthesized in the same manner as in Example 83, except that tert-butyl 3-methylsulfonyloxyazetidine-1-carboxylate was used instead of (1-acetyl-4-piperidyl)methyl methanesulfonate.

Example 96-2: Synthesis of 6-(azetidin-3-yloxy)-2-[(2R)-3-(3,4-dihydro-1H-isoquinolin-2-yl)-2-hydroxy-propyl]-3,4-dihydroisoquinolin-1-one Tert-butyl 3-[[2-[(2R)-3-(3,4-dihydro-1H-isoquinolin-2-yl)-2-hydroxy-propyl]-1-oxo-3,4-dihydroisoquinolin-6-yl]oxy]azetidine-1-carboxylate obtained in Example 96-1 as a starting material was used in the same manner as in Example 57 to obtain the title compound.

Example 96-3: Synthesis of 6-(1-acetylazetidin-3-yl)oxy-2-[(2R)-3-(3,4-dihydro-1H-isoquinolin-2-yl)-2-hydroxy-propyl]-3,4-dihydroisoquinolin-1-one 6-(Azetidin-3-yloxy)-2-[(2R)-3-(3,4-dihydro-1H-isoquinolin-2-yl)-2-hydroxy-propyl]-3,4-dihydroisoquinolin-1-one obtained in Example 96-2 as a starting material was used in the same manner as in Example 59 to obtain the title compound, except that acetic anhydride was used instead of methanesulfonyl chloride.

$^1$H NMR (400 MHz, Methanol-$d_4$) δ 7.91 (t, J=7.6 Hz, 1H), 7.24-7.08 (m, 4H), 6.83 (d, J=9.0 Hz, 1H), 6.75 (s, 1H), 5.12 (q, J=5.2 Hz, 1H), 4.73-4.62 (m, 1H), 4.43 (dd, J=11.1, 6.6 Hz, 1H), 4.34 (s, 1H), 4.24 (dd, J=9.9, 3.7 Hz, 1H), 4.11 (d, J=8.5 Hz, 2H), 3.96 (dd, J=11.0, 3.8 Hz, 1H), 3.79 (dddd, J=25.9, 19.1, 13.3, 5.5 Hz, 3H), 3.48 (dd, J=13.9, 6.9 Hz, 1H), 3.23 (s, 2H), 3.13-2.90 (m, 6H), 1.93 (s, 3H).

Example 97: Synthesis of 1-[2-[(2R)-3-(3,4-dihydro-1H-isoquinolin-2-yl)-2-hydroxy-propyl]-1-oxo-3,4-dihydroisoquinolin-6-yl]-N,N-dimethyl-piperidine-4-carboxamide

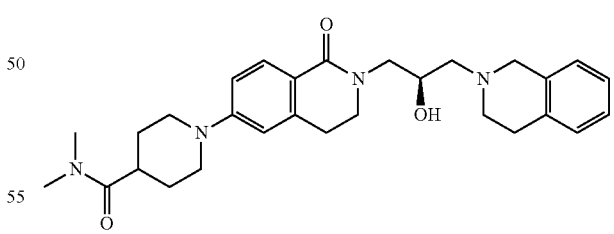

The title compound was synthesized in the same manner as in Example 2, except that N,N-dimethylpiperidine-4-carboxamide was used instead of pyrrolidine.

$^1$H NMR (400 MHz, Methanol-$d_4$) δ 7.79 (d, J=8.7 Hz, 1H), 7.18-6.98 (m, 4H), 6.90 (d, J=8.8 Hz, 1H), 6.77 (s, 1H), 4.21 (dh, J=19.3, 6.5 Hz, 1H), 3.98 (d, J=12.9 Hz, 2H), 3.88 (dd, J=13.7, 4.3 Hz, 1H), 3.80-3.63 (m, 4H), 3.37 (d, J=7.4 Hz, 1H), 3.17 (s, 3H), 3.03-2.82 (m, 12H), 2.71-2.57 (m, 2H), 1.86-1.74 (m, 4H).

Example 98: Synthesis of 6-[(1-acetylazepan-4-yl)amino]-2-[(2R)-3-(3,4-dihydro-1H-isoquinolin-2-yl)-2-hydroxy-propyl]-3,4-dihydroisoquinolin-1-one

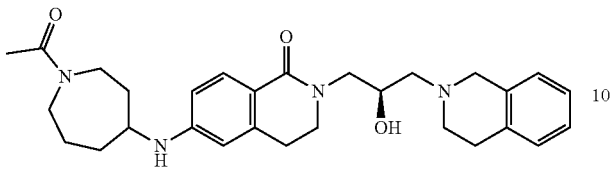

Example 98-1: Synthesis of tert-butyl 4-[[2-[(2R)-3-(3,4-dihydro-1H-isoquinolin-2-yl)-2-hydroxy-propyl]-1-oxo-3,4-dihydroisoquinolin-6-yl]amino]azepane-1-carboxylate The title compound was synthesized in the same manner as in Example 2, except that tert-butyl 4-aminoazepane-1-carboxylate was used instead of pyrrolidine.

Example 98-2: Synthesis of 6-(azepan-4-ylamino)-2-[(2R)-3-(3,4-dihydro-1H-isoquinolin-2-yl)-2-hydroxy-propyl]-3,4-dihydroisoquinolin-1-one Tert-butyl 4-[[2-[(2R)-3-(3,4-dihydro-1H-isoquinolin-2-yl)-2-hydroxy-propyl]-1-oxo-3,4-dihydroisoquinolin-6-yl]amino]azepane-1-carboxylate obtained in Example 98-1 as a starting material was used in the same manner as in Example 57 to obtain the title compound.

Example 98-3: Synthesis of 6-[(1-acetylazepan-4-yl)amino]-2-[(2R)-3-(3,4-dihydro-1H-isoquinolin-2-yl)-2-hydroxy-propyl]-3,4-dihydroisoquinolin-1-one 6-(Azepan-4-ylamino)-2-[(2R)-3-(3,4-dihydro-1H-isoquinolin-2-yl)-2-hydroxy-propyl]-3,4-dihydroisoquinolin-1-one obtained in Example 98-2 as a starting material was used in the same manner as in Example 59 to obtain the title compound, except that acetic anhydride was used instead of methanesulfonyl chloride.

$^1$H NMR (400 MHz, Methanol-$d_4$) δ 7.70 (dd, J=8.5, 3.3 Hz, 1H), 7.19-6.97 (m, 4H), 6.52 (t, J=7.3 Hz, 1H), 6.37 (d, J=5.6 Hz, 1H), 4.24 (p, J=6.8, 6.0 Hz, 1H), 3.85 (s, 3H), 3.77-3.33 (m, 9H), 2.94 (d, J=21.7 Hz, 6H), 2.81-2.64 (m, 2H), 2.15 (d, J=6.0 Hz, 4H), 2.07-1.88 (m, 2H), 1.89-1.47 (m, 2H).

Example 99: Synthesis of 6-[((1-acetylpyrrolidin-3-yl)amino]-2-[(2R)-3-(3,4-dihydro-1H-isoquinolin-2-yl)-2-hydroxy-propyl]-3,4-dihydroisoquinolin-1-one

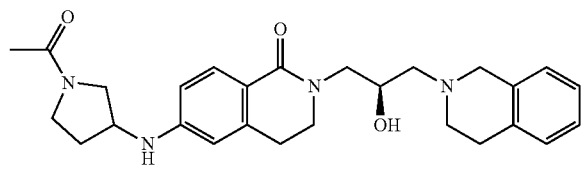 [SMILES: CC(=O)N1CCC(Nc2ccc3c(c2)CCN(C[C@H](O)CN2CCc4ccccc4C2)C3=O)C1]

The title compound was synthesized in the same manner as in Example 2, except that 1-(3-aminopyrrolidin-1-yl)ethanone was used instead of pyrrolidine.

$^1$H NMR (400 MHz, Methanol-$d_4$) δ 7.72 (dd, J=8.8, 3.7 Hz, 1H), 7.19-6.96 (m, 4H), 6.59 (t, J=6.3 Hz, 1H), 6.46 (d, J=6.7 Hz, 1H), 4.28-4.05 (m, 2H), 3.96-3.81 (m, 1H), 3.81-3.51 (m, 7H), 3.49-3.35 (m, 2H), 3.00-2.83 (m, 6H), 2.72-2.58 (m, 2H), 2.06 (t, J=11.9 Hz, 5H).

Example 100: Synthesis of 4-[2-[(2R)-3-(3,4-dihydro-1H-isoquinolin-2-yl)-2-hydroxy-propyl]-1-oxo-3,4-dihydroisoquinolin-6-yl]piperazine-1-carboxamide

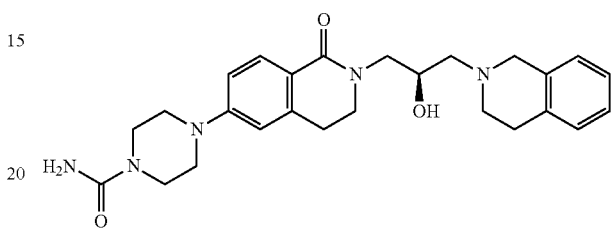

The title compound was synthesized in the same manner as in Example 2, except that piperazine-1-carboxamide was used instead of pyrrolidine.

$^1$H NMR (400 MHz, Methanol-$d_4$) δ 7.70 (d, J=8.7 Hz, 1H), 7.05-6.87 (m, 4H), 6.79 (d, J=8.9 Hz, 1H), 6.66 (s, 1H), 4.11 (p, J=6.2 Hz, 1H), 3.76 (dd, J=13.8, 4.1 Hz, 1H), 3.60 (d, J=21.1 Hz, 4H), 3.45 (d, J=5.2 Hz, 4H), 3.31-3.17 (m, 7H), 2.94-2.67 (m, 6H), 2.60-2.44 (m, 2H).

Example 101: Synthesis of 4-[2-[(2R)-3-(3,4-dihydro-1H-isoquinolin-2-yl)-2-hydroxy-propyl]-1-oxo-3,4-dihydroisoquinolin-6-yl]piperazine-1-carbonitrile

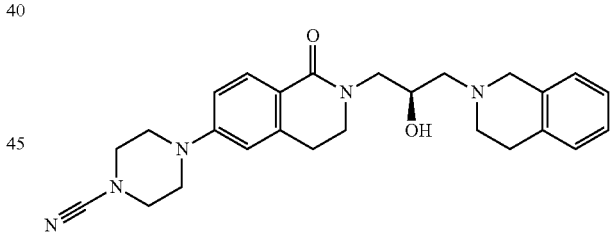

2-[(2R)-3-(3,4-dihydro-1H-isoquinolin-2-yl)-2-hydroxy-propyl]-6-piperazin-1-yl-3,4-dihydroisoquinolin-1-one (100 mg, 0.24 mmol) obtained in Example 58, BrCN (28 mg, 0.26 mmol) and $K_2CO_3$ (50 mg, 0.36 mmol) were dissolved in chloroform and stirred under heating at 60° C. Ethyl acetate was added to the reaction mixture, washed with a saturated aqueous ammonium chloride solution and a saturated aqueous sodium chloride solution, and the organic layer was dried over anhydrous magnesium sulfate. The solvent was removed by evaporation under reduced pressure, and the purification was carried out by flash chromatography to obtain 9 mg of the title compound.

$^1$H NMR (400 MHz, Methanol-$d_4$) δ 7.82 (d, J=8.7 Hz, 1H), 7.18-7.03 (m, 4H), 6.93 (d, J=8.9 Hz, 1H), 6.82 (s, 1H), 4.26 (p, J=6.9 Hz, 1H), 3.86 (d, J=9.8 Hz, 3H), 3.73 (qt, J=12.7, 6.5 Hz, 2H), 3.42 (s, 9H), 2.98 (s, 6H), 2.82-2.68 (m, 2H).

Example 102: Synthesis of 6-(6,8-dihydro-5H-imidazo[1,2-a]pyrazin-7-yl)-2-[(2R)-3-(3,4-dihydro-1H-isoquinoline-2-yl)-2-hydroxy-propyl]-3,4-dihydroisoquinolin-1-one

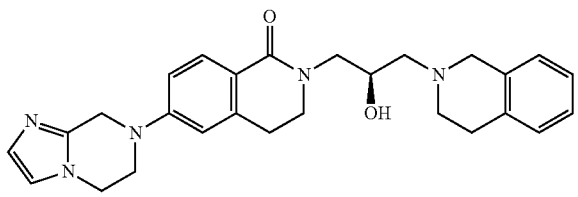 [SMILES: O=C1c2ccc(N3CCn4ccnc4C3)cc2CCN1C[C@H](O)CN1CCc2ccccc2C1]

The title compound was synthesized in the same manner as in Example 2, except that 5,6,7,8-tetrahydroimidazo[1,2-a]pyrazine was used instead of pyrrolidine.

$^1$H NMR (400 MHz, Methanol-$d_4$) δ 7.86 (d, J=8.7 Hz, 1H), 7.18-6.96 (m, 7H), 6.88 (s, 1H), 4.55 (s, 2H), 4.25 (q, J=6.8, 5.9 Hz, 1H), 4.18 (t, J=5.4 Hz, 2H), 3.96-3.82 (m, 3H), 3.83-3.65 (m, 4H), 3.43-3.36 (m, 1H), 3.09-2.84 (m, 6H), 2.67 (t, J=5.2 Hz, 2H).

Example 103: Synthesis of 2-[(2R)-3-(3,4-dihydro-1H-isoquinolin-2-yl)-2-hydroxy-propyl]-6-(3,4-dimethyl-5-oxo-piperazin-1-yl)-3,4-dihydroisoquinolin-1-one

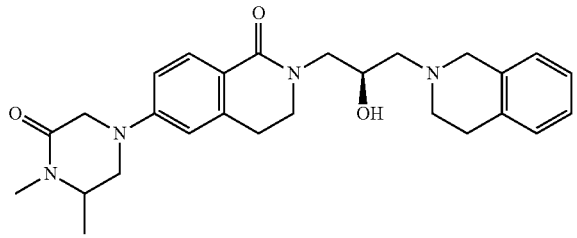 [SMILES: CC1CN(c2ccc3c(c2)CCN(C[C@H](O)CN2CCc4ccccc4C2)C3=O)CC(=O)N1C]

The title compound was synthesized in the same manner as in Example 2, except that 1,6-dimethylpiperazin-2-one was used instead of pyrrolidine.

$^1$H NMR (400 MHz, Methanol-$d_4$) δ 7.84 (d, J=8.6 Hz, 1H), 7.18-6.99 (m, 4H), 6.87 (d, J=8.8 Hz, 1H), 6.74 (s, 1H), 4.24 (q, J=6.3, 5.9 Hz, 1H), 4.12 (d, J=17.3 Hz, 1H), 3.88 (dd, J=14.0, 4.2 Hz, 1H), 3.81 (s, 3H), 3.76 (d, J=6.6 Hz, 2H), 3.70 (h, J=6.7 Hz, 2H), 3.52-3.35 (m, 2H), 3.04 (s, 3H), 3.01 (d, J=7.1 Hz, 2H), 2.94 (s, 4H), 2.70 (t, J=5.4 Hz, 2H), 1.37 (d, J=6.4 Hz, 3H).

Example 104: Synthesis of 6-(4-acetylpiperazin-1-yl)-2-[(2R)-3-(3,4-dihydro-1H-isoquinolin-2-yl)-2-hydroxy-propyl]-4,4-dimethyl-3H-isoquinolin-1-one

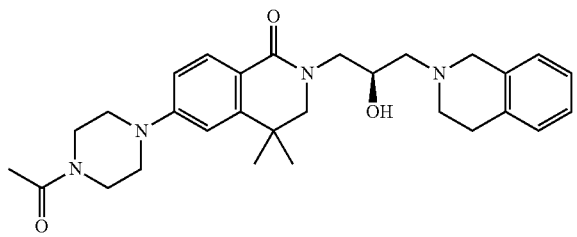 [SMILES: CC(=O)N1CCN(c2ccc3c(c2)C(C)(C)CN(C[C@H](O)CN2CCc4ccccc4C2)C3=O)CC1]

Example 104-1: Synthesis of 6-bromo-2-[(2R)-3-(3,4-dihydro-1H-isoquinolin-2-yl)-2-hydroxy-propyl]-4,4-dimethyl-3H-isoquinolin-1-one

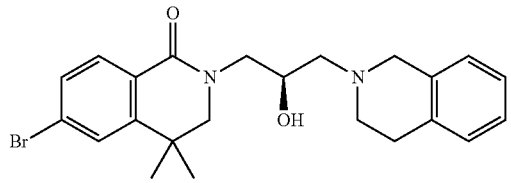 [SMILES: CC1(C)CN(C[C@H](O)CN2CCc3ccccc3C2)C(=O)c2ccc(Br)cc21]

The title compound was synthesized in the same manner as in Example 1, except that 6-bromo-4,4-dimethyl-2,3-dihydroisoquinolin-1-one was used instead of 6-bromo-3,4-dihydro-2H-isoquinolin-1-one.

$^1$H NMR (400 MHz, Methanol-$d_4$) δ 7.87 (d, J=8.3 Hz, 1H), 7.61-7.49 (m, 2H), 7.17-7.00 (m, 4H), 4.24 (d, J=12.3 Hz, 1H), 3.91 (dd, J=13.8, 4.1 Hz, 1H), 3.75 (s, 2H), 3.63 (d, J=12.8 Hz, 1H), 3.52 (d, J=12.9 Hz, 1H), 3.40 (dt, J=13.2, 6.6 Hz, 1H), 2.98-2.82 (m, 4H), 2.70-2.59 (m, 2H), 1.37 (d, J=3.5 Hz, 6H).

Example 104-2: Synthesis of 6-(4-acetylpiperazin-1-yl)-2-[(2R)-3-(3,4-dihydro-1H-isoquinolin-2-yl)-2-hydroxy-propyl]-4,4-dimethyl-3H-isoquinolin-1-one 6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 2 to obtain the title compound, except that N-acetylpiperazine was used instead of pyrrolidine.

$^1$H NMR (400 MHz, Methanol-$d_4$) δ 7.85 (d, J=8.5 Hz, 1H), 7.17-7.00 (m, 4H), 6.95-6.84 (m, 2H), 4.30-4.18 (m, 1H), 3.90 (dd, J=13.6, 4.3 Hz, 1H), 3.80-3.68 (m, 6H), 3.57 (d, J=12.5 Hz, 1H), 3.49-3.34 (m, 6H), 2.91 (dd, J=15.1, 5.1 Hz, 4H), 2.72-2.57 (m, 2H), 2.17 (d, J=1.7 Hz, 3H), 1.35 (d, J=4.1 Hz, 6H).

Example 105: Synthesis of 6-(4-acetylpiperazin-1-yl)-2-[(2R)-3-(3,4-dihydro-1H-isoquinolin-2-yl)-2-hydroxy-propyl]spiro[3H-isoquinoline-4,1'-cyclopropane]-1-one

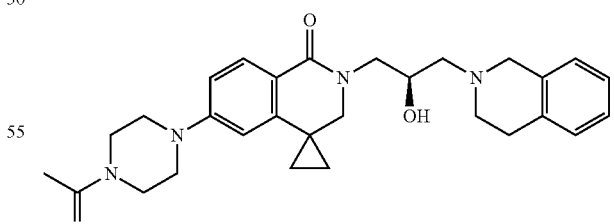

Example 105-1: Synthesis of 6-bromo-2-[(2R)-3-(3,4-dihydro-1H-isoquinolin-2-yl)-2-hydroxy-propyl]spiro[3H-isoquinoline-4,1'-cyclopropan]-1-one The title compound was synthesized in the same manner as in Example 1, except that 6-bromospiro[2,3-dihydroisoquinoline-4,1'-cyclopropane]-1-one was used instead of 6-bromo-3,4-dihydro-2H-isoquinolin-1-one.

Example 105-2: Synthesis of 6-(4-acetylpiperazin-1-yl)-2-[(2R)-3-(3,4-dihydro-1H-isoquinolin-2-yl)-2-hydroxy-propyl]spiro[3H-isoquinoline-4,1'-cyclopropan]-1-one 6-Bromo-2-[(2R)-3-(3,4-dihydro-1H-isoquinolin-2-yl)-2-hydroxy-propyl]spiro[3H-isoquinoline-4,1'-cyclopropan]-1-one obtained in Example 105-1 as a starting material was used in the same manner as in Example 2 to obtain the title compound, except that N-acetylpiperazine was used instead of pyrrolidine.

¹H NMR (400 MHz, Methanol-d₄) δ 7.87 (d, J=8.7 Hz, 1H), 7.18-7.00 (m, 4H), 6.90 (d, J=8.8 Hz, 1H), 6.44 (s, 1H), 4.23 (s, 1H), 3.88 (dd, J=14.1, 4.2 Hz, 1H), 3.80-3.64 (m, 6H), 3.55 (q, J=12.8 Hz, 3H), 3.38 (t, J=4.9 Hz, 4H), 3.02-2.84 (m, 4H), 2.65 (d, J=7.4 Hz, 2H), 2.16 (s, 3H), 1.18-0.98 (m, 4H).

Example 106: Synthesis of 2-[(2R)-3-(3,4-dihydro-1H-isoquinolin-2-yl)-2-hydroxy-propyl]-6-(4-pyrrolidin-1-yl-1-piperidyl)-3,4-dihydroisoquinolin-1-one

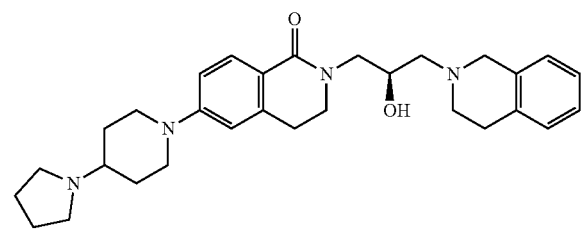 [SMILES: O=C1c2ccc(N3CCC(N4CCCC4)CC3)cc2CCN1C[C@H](O)CN1CCc2ccccc2C1]

The title compound was synthesized in the same manner as in Example 2, except that 4-pyrrolidin-1-ylpiperidine was used instead of pyrrolidine.

¹H NMR (400 MHz, Methanol-d₄) δ 7.79 (d, J=8.7 Hz, 1H), 7.15-6.99 (m, 4H), 6.90 (d, J=8.9 Hz, 1H), 6.78 (s, 1H), 4.30-4.14 (m, 1H), 4.05-3.81 (m, 3H), 3.72 (d, J=22.4 Hz, 4H), 3.37 (d, J=7.4 Hz, 1H), 3.03-2.71 (m, 11H), 2.71-2.57 (m, 2H), 2.44 (t, J=11.5 Hz, 1H), 2.08 (d, J=13.9 Hz, 3H), 1.88 (d, J=5.4 Hz, 4H), 1.62 (qd, J=12.2, 6.4 Hz, 2H).

Example 107: Synthesis of 2-[(2R)-3-(3,4-dihydro-1H-isoquinolin-2-yl)-2-hydroxy-propyl]-6-[4-(1-piperidyl)-1-piperidyl]-3,4-dihydroisoquinolin-1-one

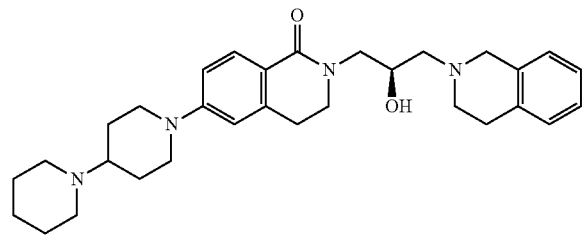 [SMILES: O=C1c2ccc(N3CCC(N4CCCCC4)CC3)cc2CCN1C[C@H](O)CN1CCc2ccccc2C1]

The title compound was synthesized in the same manner as in Example 2, except that 1-(4-piperidyl)piperidine was used instead of pyrrolidine.

¹H NMR (400 MHz, Methanol-d₄) δ 7.79 (d, J=8.7 Hz, 1H), 7.16-6.98 (m, 4H), 6.90 (d, J=8.9 Hz, 1H), 6.77 (s, 1H), 4.22 (p, J=6.2 Hz, 1H), 4.02 (d, J=13.0 Hz, 2H), 3.88 (dd, J=13.8, 4.2 Hz, 1H), 3.72 (d, J=22.7 Hz, 4H), 3.37 (d, J=7.4 Hz, 1H), 3.02-2.77 (m, 8H), 2.77-2.55 (m, 7H), 2.02 (d, J=12.1 Hz, 2H), 1.67 (dt, J=14.6, 7.4 Hz, 6H), 1.54 (q, J=6.0 Hz, 2H).

Example 108: Synthesis of 2-[(2R)-3-(3,4-dihydro-1H-isoquinolin-2-yl)-2-hydroxy-propyl]-6-(4-morpholino-1-piperidyl)-3,4-dihydroisoquinolin-1-one

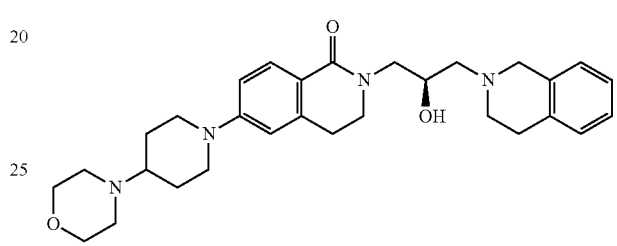

The title compound was synthesized in the same manner as in Example 2, except that 4-(4-piperidyl)morpholine was used instead of pyrrolidine.

¹H NMR (400 MHz, Methanol-d₄) δ 7.78 (d, J=8.7 Hz, 1H), 7.20-7.01 (m, 4H), 6.90 (d, J=8.9 Hz, 1H), 6.77 (s, 1H), 4.23 (p, J=6.6, 5.8 Hz, 1H), 3.99 (d, J=13.1 Hz, 2H), 3.86 (dt, J=15.4, 7.7 Hz, 1H), 3.82-3.63 (m, 8H), 3.42-3.34 (m, 1H), 3.01-2.78 (m, 8H), 2.65 (dt, J=18.4, 4.2 Hz, 6H), 2.47-2.37 (m, 1H), 2.08-1.95 (m, 2H), 1.64-1.50 (m, 2H).

Example 109: Synthesis of 2-[(2R)-3-(3,4-dihydro-1H-isoquinolin-2-yl)-2-hydroxy-propyl]-6-[4-(2-methoxyethyl)piperazin-1-yl]-3,4-dihydroisoquinolin-1-one

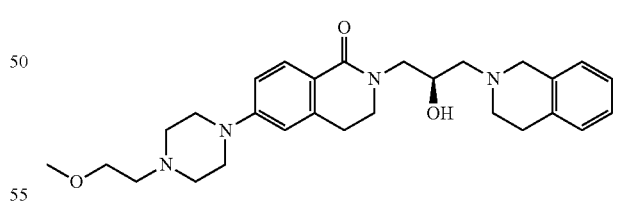

The title compound was synthesized in the same manner as in Example 2, except that 1-(2-methoxyethyl)piperazine was used instead of pyrrolidine.

¹H NMR (400 MHz, Methanol-d₄) δ 7.79 (d, J=8.6 Hz, 1H), 7.18-7.00 (m, 4H), 6.90 (d, J=9.0 Hz, 1H), 6.78 (s, 1H), 4.23 (d, J=7.9 Hz, 1H), 4.01 (d, J=13.0 Hz, 2H), 3.88 (dd, J=13.9, 4.2 Hz, 1H), 3.80-3.61 (m, 4H), 3.40-3.34 (m, 1H), 3.03-2.78 (m, 8H), 2.72-2.60 (m, 2H), 2.54 (t, J=11.7 Hz, 1H), 2.40 (s, 6H), 2.02 (d, J=12.9 Hz, 2H), 1.59 (tt, J=13.4, 6.8 Hz, 2H).

Example 110: Synthesis of 2-[(2R)-3-(3,4-dihydro-1H-isoquinolin-2-yl)-2-hydroxy-propyl]-6-[4-(dimethylamino)-1-piperidyl]-3,4-dihydroisoquinolin-1-one

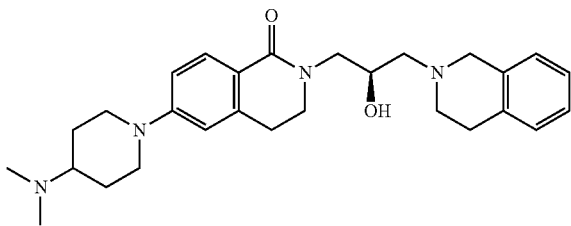 [SMILES: CN(C)C1CCN(c2ccc3c(c2)CCN(C[C@H](O)CN2CCc4ccccc4C2)C3=O)CC1]

The title compound was synthesized in the same manner as in Example 2, except that N,N-dimethylpiperidin-4-amine was used instead of pyrrolidine.

$^1$H NMR (400 MHz, Methanol-$d_4$) δ 7.80 (d, J=8.7 Hz, 1H), 7.17-7.00 (m, 4H), 6.90 (d, J=8.9 Hz, 1H), 6.77 (s, 1H), 4.23 (p, J=6.6 Hz, 1H), 3.96-3.83 (m, 1H), 3.82-3.65 (m, 4H), 3.64-3.47 (m, 4H), 3.41-3.34 (m, 7H), 3.04-2.83 (m, 6H), 2.78-2.58 (m, 7H).

Example 111: Synthesis of 2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one

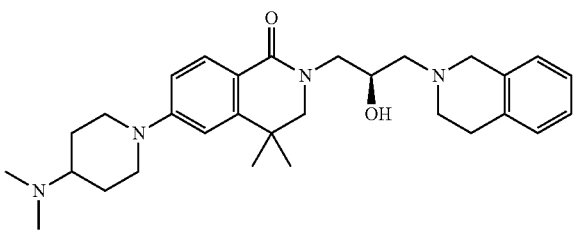 [SMILES: CN(C)C1CCN(c2ccc3c(c2)C(C)(C)CN(C[C@H](O)CN2CCc4ccccc4C2)C3=O)CC1]

6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 2 to obtain the title compound, except that N,N-dimethylpiperidin-4-amine was used instead of pyrrolidine.

$^1$H NMR (400 MHz, Methanol-$d_4$) δ 7.82 (d, J=8.6 Hz, 1H), 7.18-7.00 (m, 4H), 6.95-6.78 (m, 2H), 4.23 (s, 1H), 4.02 (d, J=12.9 Hz, 2H), 3.94-3.85 (m, 1H), 3.76 (s, 2H), 3.56 (d, J=13.0 Hz, 1H), 3.50-3.35 (m, 2H), 3.00-2.78 (m, 6H), 2.66 (d, J=6.4 Hz, 2H), 2.53 (t, J=12.4 Hz, 1H), 2.40 (s, 5H), 2.04 (dd, J=11.7, 5.3 Hz, 3H), 1.60 (q, J=11.7 Hz, 2H), 1.34 (d, J=4.1 Hz, 6H).

Example 112: Synthesis of 2-[(2R)-3-(3,4-dihydro-1H-isoquinolin-2-yl)-2-hydroxy-propyl]-4,4-dimethyl-6-morpholino-3H-isoquinolin-1-one

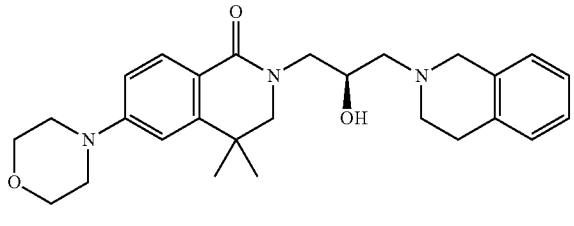 [SMILES: CC1(C)CN(C[C@H](O)CN2CCc3ccccc3C2)C(=O)c2ccc(N3CCOCC3)cc21]

6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 2 to obtain the title compound, except that morpholine was used instead of pyrrolidine.

$^1$H NMR (400 MHz, Methanol-$d_4$) δ 7.85 (d, J=8.6 Hz, 1H), 7.19-7.00 (m, 4H), 6.94-6.81 (m, 2H), 4.24 (d, J=8.1 Hz, 1H), 3.96-3.79 (m, 4H), 3.76 (s, 2H), 3.62-3.36 (m, 3H), 3.29 (d, J=4.6 Hz, 5H), 2.91 (dd, J=17.0, 5.4 Hz, 4H), 2.66 (d, J=7.4 Hz, 2H), 1.35 (d, J=4.1 Hz, 6H).

Example 113: Synthesis of 2-[(2R)-3-(3,4-dihydro-1H-isoquinolin-2-yl)-2-hydroxy-propyl]-6-(2-morpholinoethoxy)-3,4-dihydroisoquinolin-1-one

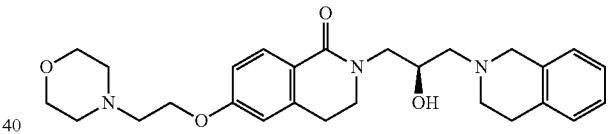

The title compound was synthesized in the same manner as in Example 83, except that 4-(2-chloroethyl)morpholine was used instead of (1-acetyl-4-piperidyl)methyl methanesulfonate.

$^1$H NMR (400 MHz, Methanol-$d_4$) δ 7.89 (q, J=7.9, 6.5 Hz, 1H), 7.25 (d, J=7.0 Hz, 1H), 7.19-7.02 (m, 3H), 6.95 (dd, J=19.4, 8.9 Hz, 1H), 6.85 (s, 1H), 4.32-4.15 (m, 3H), 3.87 (d, J=11.1 Hz, 2H), 3.71 (dtd, J=18.6, 14.2, 13.7, 4.9 Hz, 8H), 3.58 (t, J=4.9 Hz, 2H), 3.44 (ddd, J=20.9, 15.6, 9.8 Hz, 2H), 3.10-2.92 (m, 4H), 2.80 (dt, J=34.2, 6.6 Hz, 3H), 2.62 (t, J=4.6 Hz, 3H).

Example 114: Synthesis of 2-[(2R)-3-(3,4-dihydro-1H-isoquinolin-2-yl)-2-hydroxy-propyl]-6-[(1-ethyl-4-piperidyl)oxy]-3,4-dihydroisoquinolin-1-one

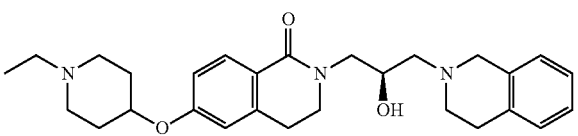 [SMILES: CCN1CCC(Oc2ccc3c(c2)CCN(C[C@H](O)CN2CCc4ccccc4C2)C3=O)CC1]

Example 114-1: Synthesis of tert-butyl 4-[[2-[(2R)-3-(3,4-dihydro-1H-isoquinolin-2-yl)-2-hydroxy-propyl]-1-oxo-3,4-dihydroisoquinolin-6-yl]oxy]piperidine-1-carboxylate The title compound was synthesized in the same manner as in Example 83, except that tert-butyl 4-methylsulfonyloxypiperidine-1-carboxylate was used instead of (1-acetyl-4-piperidyl)methyl methanesulfonate.

Example 114-2: Synthesis of 2-[(2R)-3-(3,4-dihydro-1H-isoquinolin-2-yl)-2-hydroxy-propyl]-6-(4-piperidyloxy)-3,4-dihydroisoquinolin-1-one Tert-butyl 4-[[2-[(2R)-3-(3,4-dihydro-1H-isoquinolin-2-yl)-2-hydroxy-propyl]-1-oxo-3,4-dihydroisoquinolin-6-yl]oxy]piperidine-1-carboxylate obtained in Example 114-1 as a starting material was used in the same manner as in Example 57 to obtain the title compound.

Example 114-3: Synthesis of 2-[(2R)-3-(3,4-dihydro-1H-isoquinolin-2-yl)-2-hydroxy-propyl]-6-[(1-ethyl-4-piperidyl)oxy]-3,4-dihydroisoquinolin-1-one 2-[(2R)-3-(3,4-dihydro-1H-isoquinolin-2-yl)-2-hydroxy-propyl]-6-(4-piperidyloxy)-3,4-dihydroisoquinolin-1-one (93 mg, 0.17 mmol) obtained in Example 114-2, acetaldehyde (50 μL, 0.85 mmol) and NaBH$_3$CN (55 μL, 0.85 mmol) were dissolved in methanol (4 mL) and stirred at room temperature. Ethyl acetate was added to the reaction mixture, washed with a saturated aqueous K$_2$CO$_3$ solution, and the organic layer was dried over anhydrous magnesium sulfate. The solvent was removed by evaporation under reduced pressure, and the purification was carried out by flash chromatography to obtain 22 mg of the title compound.

$^1$H NMR (400 MHz, Methanol-d$_4$) δ 7.88 (d, J=8.6 Hz, 1H), 7.17-6.97 (m, 4H), 6.92 (d, J=8.7 Hz, 1H), 6.84 (s, 1H), 4.60 (s, 1H), 4.23 (dt, J=8.2, 5.1 Hz, 1H), 3.89 (dd, J=13.7, 4.2 Hz, 1H), 3.74 (d, J=18.5 Hz, 4H), 3.38 (dd, J=13.6, 7.4 Hz, 1H), 3.01 (q, J=7.6, 7.0 Hz, 2H), 2.91 (dq, J=10.7, 5.9, 5.4 Hz, 6H), 2.72-2.52 (m, 6H), 2.17-2.00 (m, 2H), 1.97-1.81 (m, 2H), 1.19 (t, J=7.3 Hz, 3H).

Example 115: Synthesis of 2-[(2R)-3-(3,4-dihydro-1H-isoquinolin-2-yl)-2-hydroxy-propyl]-6-[(1-ethyl-4-piperidyl)methyloxy]-3,4-dihydroisoquinolin-1-one

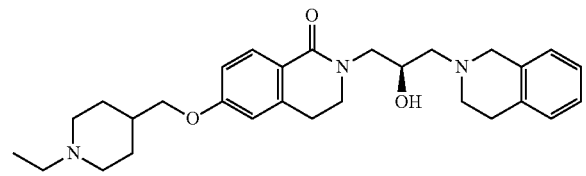 [SMILES: CCN1CCC(COc2ccc3c(c2)CCN(C[C@H](O)CN2CCc4ccccc4C2)C3=O)CC1]

Example 115-1: Synthesis of tert-butyl 4-[[2-[(2R)-3-(3,4-dihydro-1H-isoquinolin-2-yl)-2-hydroxy-propyl]-1-oxo-3,4-dihydroisoquinolin-6-yl]oxymethyl]piperidine-1-carboxylate The title compound was synthesized in the same manner as in Example 83, except that tert-butyl 4-(methylsulfonyloxymethyl)piperidine-1-carboxylate was used instead of (1-acetyl-4-piperidyl)methyl methanesulfonate.

Example 115-2: Synthesis of 2-[(2R)-3-(3,4-dihydro-1H-isoquinolin-2-yl)-2-hydroxy-propyl]-6-(4-piperidylmethoxy)-3,4-dihydroisoquinolin-1-one Tert-butyl 4-[[2-[(2R)-3-(3,4-dihydro-1H-isoquinolin-2-yl)-2-hydroxy-propyl]-1-oxo-3,4-dihydroisoquinolin-6-yl]oxymethyl]piperidine-1-carboxylate obtained in Example 115-1 as a starting material was used in the same manner as in Example 57 to obtain the title compound.

Example 115-3: Synthesis of 2-[(2R)-3-(3,4-dihydro-1H-isoquinolin-2-yl)-2-hydroxy-propyl]-6-[(1-ethyl-4-piperidyl)methoxy]-3,4-dihydroisoquinolin-1-one 2-[(2R)-3-(3,4-dihydro-1H-isoquinolin-2-yl)-2-hydroxy-propyl]-6-(4-piperidylmethoxy)-3,4-dihydroisoquinolin-1-one obtained in Example 115-2 as a starting material was used in the same manner as in Example 114-3 to obtain the title compound.

$^1$H NMR (400 MHz, Methanol-d$_4$) δ 7.87 (d, J=8.6 Hz, 1H), 7.19-6.97 (m, 4H), 6.88 (d, J=8.8 Hz, 1H), 6.80 (s, 1H), 4.23 (p, J=6.2 Hz, 1H), 3.90 (dd, J=14.6, 4.7 Hz, 3H), 3.84-3.65 (m, 4H), 3.41-3.34 (m, 1H), 3.11-2.96 (m, 4H), 2.96-2.80 (m, 4H), 2.70-2.56 (m, 2H), 2.47 (q, J=7.2 Hz, 2H), 2.05 (t, J=11.8 Hz, 2H), 1.89 (d, J=13.0 Hz, 3H), 1.46 (p, J=10.7, 9.4 Hz, 2H), 1.14 (t, J=7.2 Hz, 3H).

Example 116: Synthesis of 2-[(2R)-3-(3,4-dihydro-1H-isoquinolin-2-yl)-2-hydroxy-propyl]-6-[3-(dimethylamino)-1-piperidyl]-3,4-dihydroisoquinolin-1-one

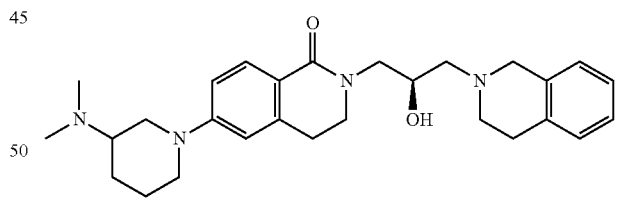

The title compound was synthesized in the same manner as in Example 2, except that N,N-dimethylpiperidin-3-amine was used instead of pyrrolidine.

$^1$H NMR (400 MHz, Methanol-d$_4$) δ 7.79 (d, J=8.8 Hz, 1H), 7.17-7.02 (m, 4H), 6.89 (d, J=8.9 Hz, 1H), 6.75 (s, 1H), 4.23 (s, 1H), 4.03 (d, J=12.6 Hz, 1H), 3.87 (t, J=12.5 Hz, 2H), 3.73 (d, J=23.1 Hz, 4H), 3.38 (d, J=7.0 Hz, 1H), 3.04-2.75 (m, 8H), 2.65 (d, J=8.0 Hz, 2H), 2.54-2.43 (m, 1H), 2.41 (d, J=1.9 Hz, 6H), 2.08 (d, J=13.6 Hz, 1H), 1.94-1.79 (m, 1H), 1.63 (t, J=13.4 Hz, 1H), 1.50 (q, J=12.3 Hz, 1H).

Example 117: Synthesis of 2-[(2R)-3-(3,4-dihydro-1H-isoquinolin-2-yl)-2-hydroxy-propyl]-6-[4-[(dimethylamino)methyl]-1-piperidyl]-3,4-dihydroisoquinolin-1-one

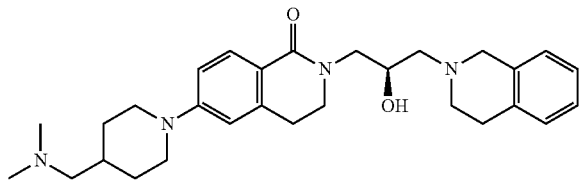 [SMILES: CN(C)CC1CCN(c2ccc3c(c2)CCN(C[C@H](O)CN2CCc4ccccc4C2)C3=O)CC1]

The title compound was synthesized in the same manner as in Example 2, except that N,N-dimethyl-1-(4-piperidyl)methanamine was used instead of pyrrolidine.

$^1$H NMR (400 MHz, Methanol-$d_4$) δ 7.78 (d, J=8.7 Hz, 1H), 7.18-6.99 (m, 4H), 6.89 (d, J=8.8 Hz, 1H), 6.76 (s, 1H), 4.22 (d, J=6.5 Hz, 1H), 3.99-3.82 (m, 3H), 3.81-3.62 (m, 4H), 3.37 (d, J=7.3 Hz, 1H), 2.89 (ddd, J=25.6, 19.0, 12.1 Hz, 7H), 2.72-2.58 (m, 2H), 2.30 (d, J=10.2 Hz, 7H), 1.86 (q, J=21.4, 17.7 Hz, 3H), 1.30 (q, J=11.9 Hz, 2H).

Example 118: Synthesis of 6-[4-(diethylamino)-1-piperidyl]-2-[(2R)-3-(3,4-dihydro-1H-isoquinolin-2-yl)-2-hydroxy-propyl]-3,4-dihydroisoquinolin-1-one

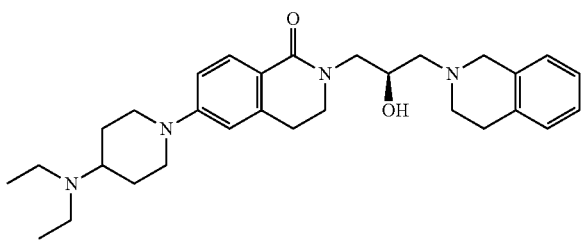 [SMILES: CCN(CC)C1CCN(c2ccc3c(c2)CCN(C[C@H](O)CN2CCc4ccccc4C2)C3=O)CC1]

The title compound was synthesized in the same manner as in Example 2, except that N,N-diethylpiperidin-4-amine was used instead of pyrrolidine.

$^1$H NMR (400 MHz, Methanol-$d_4$) δ 7.79 (d, J=8.5 Hz, 1H), 7.08 (d, J=20.8 Hz, 4H), 6.91 (d, J=8.7 Hz, 1H), 6.78 (s, 1H), 4.23 (s, 1H), 4.03 (d, J=12.9 Hz, 2H), 3.88 (d, J=14.1 Hz, 1H), 3.75 (s, 4H), 3.39 (s, 2H), 2.88 (ddd, J=33.5, 24.9, 16.2 Hz, 11H), 2.64 (d, J=7.6 Hz, 2H), 1.99 (dt, J=30.8, 14.2 Hz, 3H), 1.75-1.57 (m, 2H), 1.15 (t, J=7.3 Hz, 6H).

Example 119: Synthesis of 2-[(2R)-3-(3,4-dihydro-1H-isoquinolin-2-yl)-2-hydroxy-propyl]-6-[4-[2-(dimethylamino)ethoxy]-1-piperidyl]-3,4-dihydroisoquinolin-1-one

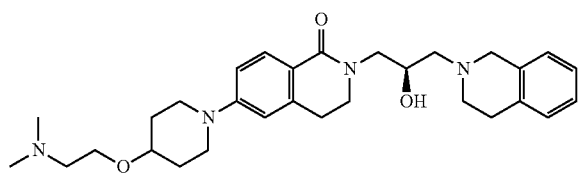 [SMILES: CN(C)CCOC1CCN(c2ccc3c(c2)CCN(C[C@H](O)CN2CCc4ccccc4C2)C3=O)CC1]

The title compound was synthesized in the same manner as in Example 2, except that N,N-dimethyl-2-(4-piperidyloxy)ethanamine was used instead of pyrrolidine.

$^1$H NMR (400 MHz, Methanol-$d_4$) δ 7.78 (d, J=9.8 Hz, 1H), 7.19-7.00 (m, 4H), 6.90 (d, J=8.9 Hz, 1H), 6.77 (s, 1H), 4.23 (s, 1H), 3.88 (dd, J=13.5, 4.2 Hz, 1H), 3.80-3.67 (m, 7H), 3.60 (s, 1H), 3.38 (d, J=7.2 Hz, 1H), 3.13 (t, J=11.1 Hz, 2H), 2.92 (ddd, J=27.2, 12.7, 6.4 Hz, 6H), 2.76 (t, J=5.8 Hz, 2H), 2.65 (d, J=7.6 Hz, 2H), 2.45 (s, 6H), 2.02 (d, J=12.9 Hz, 2H), 1.92 (s, 1H), 1.66 (d, J=10.3 Hz, 2H).

Example 120: Synthesis of 2-[(2R)-3-(3,4-dihydro-1H-isoquinolin-2-yl)-2-hydroxy-propyl]-6-[4-[2-methoxyethyl(methyl)amino]-1-piperidyl]-3,4-dihydroisoquinolin-1-one

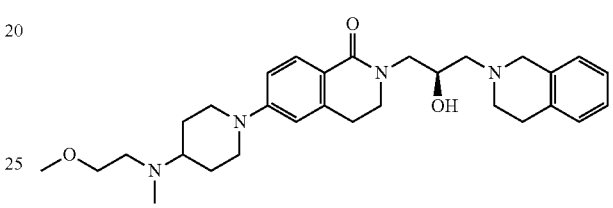

The title compound was synthesized in the same manner as in Example 2, except that N-(2-methoxyethyl)-N-methyl-piperidin-4-amine was used instead of pyrrolidine.

$^1$H NMR (400 MHz, Methanol-$d_4$) δ 7.78 (d, J=8.7 Hz, 1H), 7.18-7.00 (m, 4H), 6.90 (d, J=8.8 Hz, 1H), 6.77 (s, 1H), 4.22 (s, 1H), 4.00 (d, J=12.8 Hz, 2H), 3.88 (dd, J=13.8, 4.2 Hz, 1H), 3.72 (d, J=21.2 Hz, 4H), 3.53 (t, J=5.8 Hz, 2H), 3.36 (d, J=1.8 Hz, 4H), 3.05-2.78 (m, 8H), 2.78-2.56 (m, 5H), 2.36 (s, 3H), 1.94 (d, J=12.6 Hz, 2H), 1.61 (dt, J=14.6, 10.2 Hz, 2H).

Example 121: Synthesis of 2-[(2R)-3-(3,4-dihydro-1H-isoquinolin-2-yl)-2-hydroxy-propyl]-6-[4-(oxetan-3-yl)piperazin-1-yl]-3,4-dihydroisoquinolin-1-one

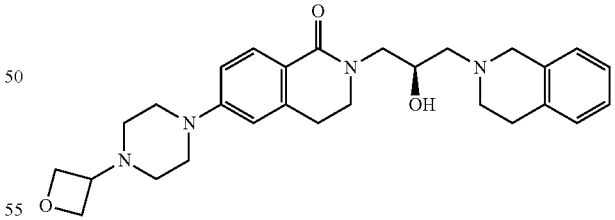

The title compound was synthesized in the same manner as in Example 2, except that 1-(oxetan-3-yl)piperazine was used instead of pyrrolidine.

$^1$H NMR (400 MHz, Methanol-$d_4$) δ 7.81 (d, J=8.6 Hz, 1H), 7.17-7.01 (m, 4H), 6.91 (d, J=8.9 Hz, 1H), 6.78 (s, 1H), 4.74 (t, J=6.6 Hz, 2H), 4.66 (t, J=6.2 Hz, 2H), 4.23 (p, J=6.7 Hz, 1H), 3.88 (dd, J=13.9, 4.1 Hz, 1H), 3.73 (d, J=22.7 Hz, 4H), 3.56 (p, J=6.3 Hz, 1H), 3.38 (t, J=5.1 Hz, 5H), 3.03-2.82 (m, 6H), 2.70-2.58 (m, 2H), 2.52 (t, J=5.1 Hz, 4H).

Example 122: Synthesis of 2-[(2R)-3-(3,4-dihydro-1H-isoquinolin-2-yl)-2-hydroxy-propyl]-6-(4-tetrahydropyran-4-ylpiperazin-1-yl)-3,4-dihydroisoquinolin-1-one

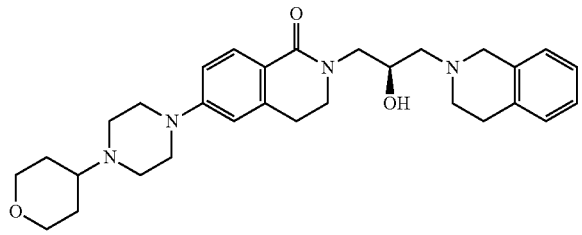 [SMILES: O=C1c2ccc(N3CCN(C4CCOCC4)CC3)cc2CCN1C[C@H](O)CN1CCc2ccccc2C1]

2-[(2R)-3-(3,4-dihydro-1H-isoquinolin-2-yl)-2-hydroxy-propyl]-6-piperazin-1-yl-3,4-dihydroisoquinolin-1-one obtained in Example 58 as a starting material was used in the same manner as in Example 114-3 to obtain the title compound, except that tetrahydropyran-4-one was used instead of acetaldehyde.

$^1$H NMR (400 MHz, Methanol-d$_4$) δ 7.80 (d, J=8.7 Hz, 1H), 7.18-7.01 (m, 4H), 6.91 (d, J=8.8 Hz, 1H), 6.78 (s, 1H), 4.23 (s, 1H), 4.11-3.97 (m, 2H), 3.88 (dd, J=13.6, 4.2 Hz, 1H), 3.81-3.64 (m, 4H), 3.44 (t, J=11.8 Hz, 3H), 3.37 (t, J=4.6 Hz, 4H), 3.05-2.84 (m, 6H), 2.76 (t, J=5.1 Hz, 4H), 2.66 (d, J=7.7 Hz, 2H), 2.56-2.40 (m, 1H), 1.91 (d, J=12.5 Hz, 2H), 1.67-1.50 (m, 2H).

Example 123: Synthesis of 6-[4-(diethylamino)-1-piperidyl]-2-[(2R)-3-(3,4-dihydro-1H-isoquinolin-2-yl)-2-hydroxy-propyl]-4,4-dimethyl-3H-isoquinolin-1-one

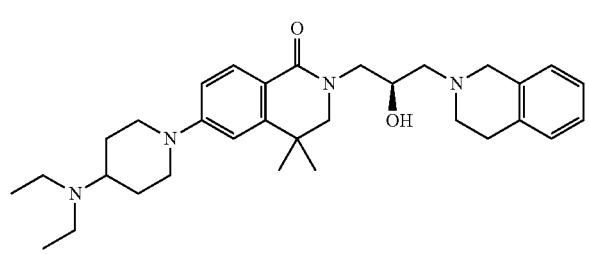 [SMILES: CCN(CC)C1CCN(c2ccc3c(c2)C(C)(C)CN(C[C@H](O)CN2CCc4ccccc4C2)C3=O)CC1]

6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 2, except that N,N-diethylpiperidin-4-amine was used instead of pyrrolidine.

$^1$H NMR (400 MHz, Methanol-d$_4$) δ 7.82 (d, J=8.6 Hz, 1H), 7.21-6.98 (m, 4H), 6.97-6.78 (m, 2H), 4.23 (s, 1H), 4.03 (d, J=13.0 Hz, 2H), 3.90 (dd, J=13.4 Hz, 1H), 3.75 (s, 2H), 3.56 (d, J=12.7 Hz, 1H), 3.49-3.34 (m, 2H), 2.99-2.73 (m, 10H), 2.71-2.58 (m, 2H), 2.02 (dd, J=21.5, 11.5 Hz, 3H), 1.66 (q, J=12.0, 11.5 Hz, 2H), 1.34 (d, J=4.2 Hz, 6H), 1.15 (t, J=7.3 Hz, 6H).

Example 124: Synthesis of 2-[(2R)-3-(3,4-dihydro-1H-isoquinolin-2-yl)-2-hydroxy-propyl]-4,4-dimethyl-6-(4-pyrrolidin-1-yl-1-piperidyl)-3H-isoquinolin-1-one

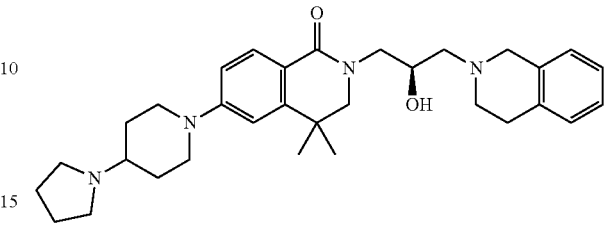

6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 2, except that 4-pyrrolidin-1-ylpiperidine was used instead of pyrrolidine.

$^1$H NMR (400 MHz, Methanol-d$_4$) δ 7.82 (d, J=8.7 Hz, 1H), 7.18-7.01 (m, 4H), 6.94-6.82 (m, 2H), 4.23 (s, 1H), 3.98 (d, J=13.1 Hz, 2H), 3.90 (dd, J=13.9, 4.4 Hz, 1H), 3.76 (s, 2H), 3.56 (d, J=12.6 Hz, 1H), 3.49-3.35 (m, 2H), 2.97-2.77 (m, 9H), 2.69-2.60 (m, 2H), 2.47 (d, J=12.0 Hz, 1H), 2.08 (dd, J=24.5, 11.3 Hz, 3H), 1.88 (d, J=5.8 Hz, 4H), 1.72-1.55 (m, 2H), 1.34 (d, J=4.1 Hz, 6H).

Example 125: Synthesis of 4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde

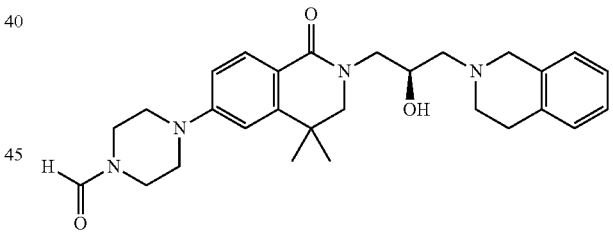

6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 2, except that N-formylpiperazine was used instead of pyrrolidine.

$^1$H NMR (400 MHz, Methanol-d$_4$) δ 8.13 (s, 1H), 7.86 (d, J=8.6 Hz, 1H), 7.18-7.00 (m, 4H), 6.99-6.88 (m, 2H), 4.24 (s, 1H), 3.90 (dd, J=14.0, 4.2 Hz, 1H), 3.76 (s, 2H), 3.69 (t, J=5.4 Hz, 2H), 3.62 (t, J=5.0 Hz, 2H), 3.57 (d, J=12.6 Hz, 1H), 3.46 (d, J=12.6 Hz, 1H), 3.43-3.39 (m, 2H), 3.37 (d, J=5.9 Hz, 3H), 2.91 (dd, J=17.2, 5.4 Hz, 4H), 2.71-2.62 (m, 2H), 1.35 (d, J=4.2 Hz, 6H).

Example 126: Synthesis of 2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one; dihydrochloride

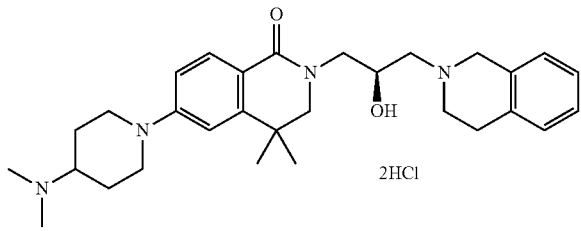 [SMILES: CN(C)C1CCN(c2ccc3c(c2)C(C)(C)CN(C[C@H](O)CN2CCc4ccccc4C2)C3=O)CC1 ; "2HCl"]

2HCl

2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one (30 mg) obtained in Example 111 was dissolved in 4 mL of 1,4-dioxane, and an excess of 4 M hydrochloric acid in dioxane solution was added and stirred at room temperature. The solvent was removed by evaporation under reduced pressure to obtain 17 mg of the title compound without further purification.

$^1$H NMR (400 MHz, Methanol-$d_4$) δ 7.92 (d, J=8.6 Hz, 1H), 7.30 (t, J=8.1 Hz, 3H), 7.23 (s, 1H), 7.15 (s, 2H), 4.75-4.57 (m, 1H), 4.54-4.37 (m, 2H), 4.09 (d, J=13.0 Hz, 2H), 3.88 (s, 1H), 3.83-3.72 (m, 2H), 3.68 (s, 4H), 3.60-3.46 (m, 4H), 3.41 (d, J=13.7 Hz, 2H), 3.17 (t, J=12.5 Hz, 3H), 2.94 (s, 6H), 2.29 (d, J=12.3 Hz, 2H), 2.00 (p, J=12.4, 11.6 Hz, 2H), 1.37 (d, J=8.1 Hz, 6H).

Example 127: Synthesis of 2-[(2R)-3-(3,4-dihydro-1H-isoquinolin-2-yl)-2-hydroxy-propyl]-6-(4-tetrahydrofuran-3-ylpiperazin-1-yl)-3,4-dihydroisoquinolin-1-one

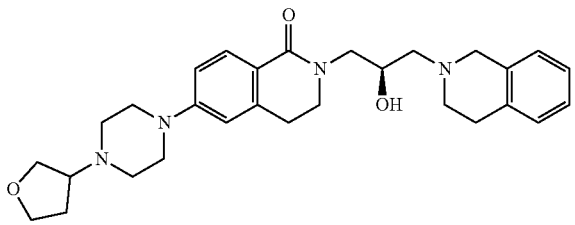 [SMILES: O=C1c2ccc(N3CCN(C4CCOC4)CC3)cc2CCN1C[C@H](O)CN1CCc2ccccc2C1]

2-[(2R)-3-(3,4-dihydro-1H-isoquinolin-2-yl)-2-hydroxy-propyl]-6-piperazin-1-yl-3,4-dihydroisoquinolin-1-one obtained in Example 58 as a starting material was used in the same manner as in Example 114-3 to obtain the title compound, except that tetrahydrofuran-3-one was used instead of acetaldehyde.

$^1$H NMR (400 MHz, Methanol-$d_4$) δ 7.81 (d, J=8.7 Hz, 1H), 7.18-7.00 (m, 4H), 6.90 (d, J=8.9 Hz, 1H), 6.77 (s, 1H), 4.23 (p, J=6.6 Hz, 1H), 3.93 (ddt, J=26.6, 13.4, 6.3 Hz, 3H), 3.84-3.62 (m, 6H), 3.36 (d, J=5.5 Hz, 4H), 3.05 (p, J=6.9 Hz, 1H), 3.00-2.82 (m, 6H), 2.72 (dt, J=10.7, 5.1 Hz, 2H), 2.67-2.54 (m, 4H), 2.15 (h, J=6.2 Hz, 1H), 2.04 (d, J=9.9 Hz, 1H), 1.91 (dq, J=16.1, 8.1 Hz, 1H)

Example 128: Synthesis of 6-(4-acetylpiperazin-1-yl)-2-[(2R)-3-(3,4-dihydro-1H-isoquinolin-2-yl)-2-hydroxy-propyl]-8-fluoro-3,4-dihydroisoquinolin-1-one

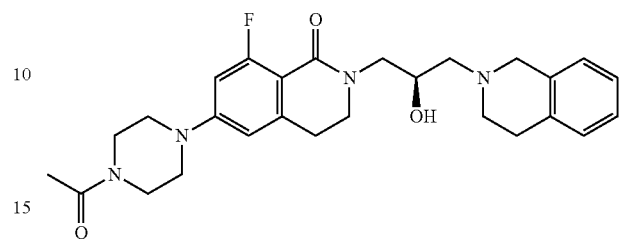

Example 128-1: Synthesis of 6-bromo-2-[(2R)-3-(3,4-dihydro-1H-isoquinolin-2-yl)-2-hydroxy-propyl]-8-fluoro-3,4-dihydroisoquinolin-1-one The title compound was synthesized in the same manner as in Example 1, except that 6-bromo-8-fluoro-3,4-dihydro-2H-isoquinolin-1-one was used instead of 6-bromo-3,4-dihydro-2H-isoquinolin-1-one.

Example 128-2: Synthesis of 6-(4-acetylpiperazin-1-yl)-2-[(2R)-3-(3,4-dihydro-1H-isoquinolin-2-yl)-2-hydroxy-propyl]-8-fluoro-3,4-dihydroisoquinolin-1-one 6-Bromo-2-[(2R)-3-(3,4-dihydro-1H-isoquinolin-2-yl)-2-hydroxy-propyl]-8-fluoro-3,4-dihydroisoquinolin-1-one obtained in Example 128-1 as a starting material was used in the same manner as in Example 2 to obtain the title compound, except that N-acetylpiperazine was used instead of pyrrolidine.

$^1$H NMR (400 MHz, Methanol-$d_4$) δ 7.39 (d, J=2.8 Hz, 1H), 7.16-7.01 (m, 4H), 6.95 (dd, J=12.2, 2.5 Hz, 1H), 4.24 (s, 1H), 3.96-3.87 (m, 1H), 3.84-3.66 (m, 8H), 3.39 (dd, J=13.7, 7.7 Hz, 1H), 3.28 (d, J=5.1 Hz, 2H), 3.22 (d, J=5.4 Hz, 2H), 2.99-2.81 (m, 6H), 2.64 (dd, J=7.0, 2.6 Hz, 2H), 2.16 (d, J=1.9 Hz, 3H).

Example 129: Synthesis of 6-(4-acetylpiperazin-1-yl)-2-[3-(3,4-dihydro-1H-isoquinolin-2-yl)-2-hydroxy-1-methyl-propyl]-3,4-dihydroisoquinolin-1-one

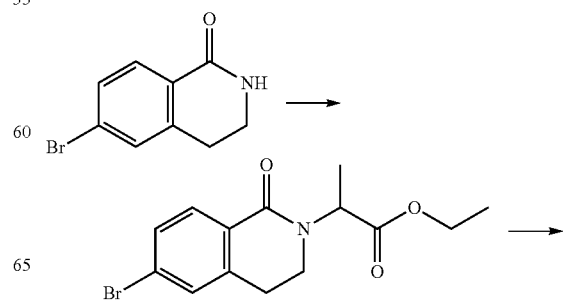

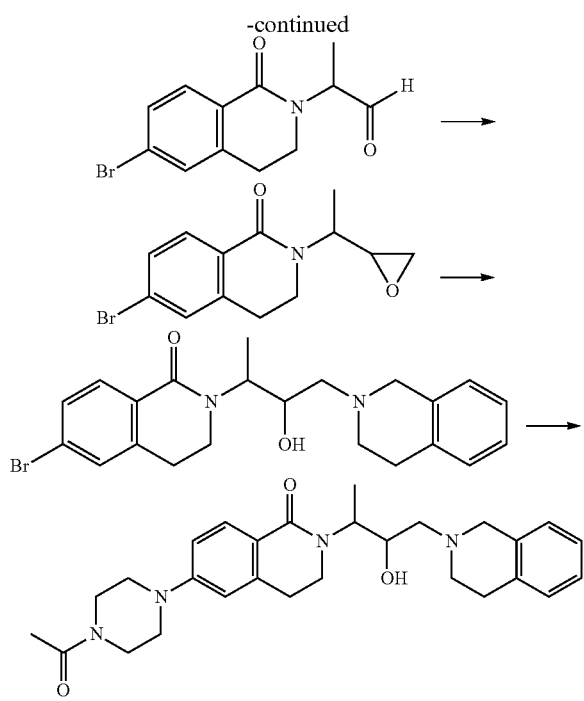

Example 129-1: Synthesis of ethyl 2-(6-bromo-1-oxo-3,4-dihydroisoquinolin-2-yl) propanate 6-Bromo-3,4-dihydro-2H-isoquinolin-1-one (1 g, 4.42 mmol), ethyl 2-bromo propionate (1.15 mL, 8.85 mmol) and Cs$_2$CO$_3$ (2.9 g, 8.85) mmol) were dissolved in 15 mL of acetonitrile and stirred at 70° C. Water was added to the reaction mixture to terminate the reaction, extraction was carried out with ethyl acetate, and the organic layer was dried over anhydrous magnesium sulfate. The solvent was removed by evaporation under reduced pressure, and the product was used in the next reaction without further purification.

Example 129-2: Synthesis of 2-(6-bromo-1-oxo-3,4-dihydroisoquinolin-2-yl) propanal Ethyl 2-(6-bromo-1-oxo-3,4-dihydroisoquinolin-2-yl) propanate (1.87 g, 5.73 mmol) obtained in Example 129-1 was dissolved in 60 mL of tetrahydrofuran and stirred while cooling to −78° C. While maintaining the temperature, DIBAL-H in toluene solution (11.5 mL, 11.47 mmol) was slowly added dropwise. After the reaction was terminated with methanol and distilled water, the reaction mixture was extracted with dichloromethane, and the organic layer was dried over anhydrous magnesium sulfate. The solvent was removed by evaporation under reduced pressure, and the product was used in the next reaction without further purification.

Example 129-3: Synthesis of 6-bromo-2-[1-(oxiran-2-yl)ethyl]-3,4-dihydroisoquinolin-1-one Trimethyl sulfoxonium iodide (8.11 g, 36.86 mmol) was dissolved in 30 mL of DMSO and stirred. NaH (60%, 1.36 g, 34.02 mmol) was added to the reaction mixture and stirred for 15 minutes. 2-(6-Bromo-1-oxo-3,4-dihydroisoquinoline-2-yl)propanal (1.6 g, 5.67 mmol) dissolved in 10 mL of DMSO was added dropwise. Methanol was added to the reaction mixture to terminate the reaction, and ethyl acetate was added thereto. The reaction mixture was washed with a saturated aqueous ammonium chloride solution and a saturated aqueous sodium chloride solution, and the organic layer was dried over anhydrous magnesium sulfate. The solvent was removed by evaporation under reduced pressure, and the product was used in the next reaction without further purification.

Example 129-4: Synthesis of 6-bromo-2-[3-(3,4-dihydro-1H-isoquinolin-2-yl)-2-hydroxy-1-methyl-propyl]-3,4-dihydroisoquinolin-1-one 6-Bromo-2-[1-(oxiran-2-yl)ethyl]-3,4-dihydroisoquinolin-1-one obtained in Example 129-3 as a starting material was used in the same manner as in Example 1-2 to obtain the title compound.

Example 129-5: Synthesis of 6-(4-acetylpiperazin-1-yl)-2-[3-(3,4-dihydro-1H-isoquinolin-2-yl)-2-hydroxy-1-yl)-2-hydroxyl-1-methyl-propyl]-3,4-dihydroisoquinolin-1-one

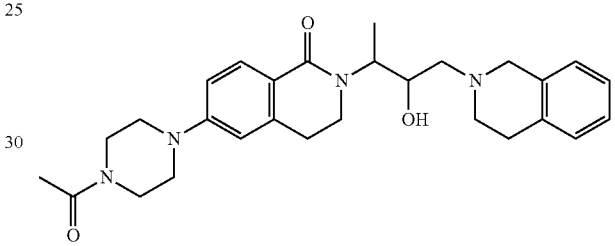

6-Bromo-2-[3-(3,4-dihydro-1H-isoquinolin-2-yl)-2-hydroxy-1-methyl-propyl]-3,4-dihydroisoquinolin-1-one obtained in Example 129-4 as a starting material was used in the same manner as in Example 2 to obtain the title compound, except that N-acetylpiperazine was used instead of pyrrolidine.

$^1$H NMR (400 MHz, Methanol-d$_4$) δ 7.83 (d, J=8.7 Hz, 1H), 7.22-7.02 (m, 4H), 6.92 (d, J=8.8 Hz, 1H), 6.80 (s, 1H), 4.70 (p, J=6.8 Hz, 1H), 4.05 (dt, J=9.0, 4.1 Hz, 1H), 3.96-3.83 (m, 2H), 3.83-3.76 (m, 1H), 3.72 (dt, J=14.6, 5.2 Hz, 4H), 3.61-3.50 (m, 1H), 3.45-3.34 (m, 3H), 3.00 (qd, J=14.2, 13.6, 5.4 Hz, 5H), 2.88 (dt, J=15.6, 5.7 Hz, 1H), 2.84-2.66 (m, 2H), 2.14 (d, J=20.8 Hz, 4H), 1.36 (d, J=7.1 Hz, 3H).

Example 130: Synthesis of 4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde; hydrochloride

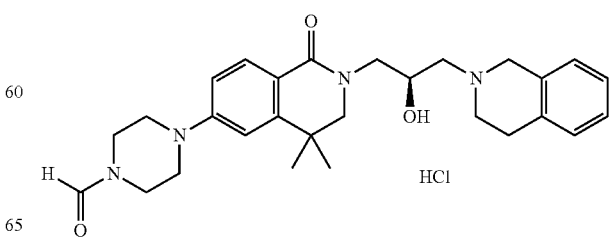

4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde obtained in Example 125 as a starting material was used in the same manner as in Example 126 to obtain the title compound.

¹H NMR (400 MHz, Methanol-d₄) δ 8.16 (s, 1H), 7.96 (d, J=8.5 Hz, 1H), 7.30 (q, J=7.8, 7.3 Hz, 3H), 7.22 (dd, J=12.3, 4.0 Hz, 3H), 4.67 (dd, J=15.5, 10.4 Hz, 1H), 4.55-4.39 (m, 2H), 3.89 (dd, J=12.4, 5.2 Hz, 1H), 3.79 (dt, J=21.1, 5.2 Hz, 5H), 3.67 (d, J=1.6 Hz, 6H), 3.64-3.53 (m, 4H), 3.50 (t, J=5.3 Hz, 2H), 3.43-3.34 (m, 2H), 3.19 (dq, J=17.4, 5.1 Hz, 1H), 1.38 (d, J=8.0 Hz, 6H).

Example 131: Synthesis of 2-[(2R)-3-(3,4-dihydro-1H-isoquinolin-2-yl)-2-hydroxy-propyl]-6-[(1-ethyl-4-piperidyl)oxy]-4,4-dimethyl-3H-isoquinolin-1-one

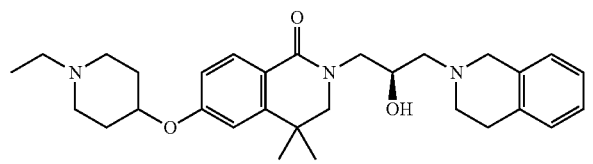 [SMILES: CCN1CCC(Oc2ccc3c(c2)C(C)(C)CN(C[C@H](O)CN2CCc4ccccc4C2)C3=O)CC1]

Example 131-1: Synthesis of tert-butyl 4-[[2-[(2R)-3-(3,4-dihydro-1H-isoquinolin-2-yl)-2-hydroxy-propyl]-4,4-dimethyl-1-oxo-3H-isoquinolin-6-yl]oxy]piperidine-1-carboxylate 6-Bromo-2-[(2R)-3-(3,4-dihydro-1H-isoquinolin-2-yl)-2-hydroxy-propyl]-4,4-dimethyl-3H-isoquinolin-1-one obtained in Example 104-1 as a starting material was used in the same manner as in Example 83 to obtain the title compound, except that tert-butyl 4-methylsulfonyloxypiperidine-1-carboxylate was used instead of (1-acetyl-4-piperidyl)methyl methanesulfonate.

Example 131-2: Synthesis of 2-[(2R)-3-(3,4-dihydro-1H-isoquinolin-2-yl)-2-hydroxy-propyl]-4,4-dimethyl-6-(4-piperidyloxy)-3H-isoquinolin-1-one Tert-butyl 4-[[2-[(2R)-3-(3,4-dihydro-1H-isoquinolin-2-yl)-2-hydroxy-propyl]-4,4-dimethyl-1-oxo-3H-isoquinolin-6-yl]oxy]piperidine-1-carboxylate obtained in Example 131-1 as a starting material was used in the same manner as in Example 57 to obtain the title compound.

Example 131-3: Synthesis of 2-[(2R)-3-(3,4-dihydro-1H-isoquinolin-2-yl)-2-hydroxy-propyl]-6-[(1-ethyl-4-piperidyl)oxy]-4,4-dimethyl-3H-isoquinolin-1-one 2-[(2R)-3-(3,4-dihydro-1H-isoquinolin-2-yl)-2-hydroxy-propyl]-4,4-dimethyl-6-(4-piperidyloxy)-3H-isoquinolin-1-one obtained in Example 131-2 as a starting material was used in the same manner as in Example 114-3 to obtain the title compound.

¹H NMR (400 MHz, Methanol-d₄) δ 7.26 (d, J=8.8 Hz, 1H), 7.09-6.98 (m, 3H), 6.95 (d, J=7.0 Hz, 1H), 6.92-6.86 (m, 1H), 6.76 (dt, J=9.1, 2.4 Hz, 1H), 4.56 (d, J=43.1 Hz, 1H), 4.21-4.06 (m, 2H), 3.91 (dd, J=14.4, 7.7 Hz, 1H), 3.70 (d, J=4.0 Hz, 2H), 3.60 (t, J=4.7 Hz, 1H), 3.54-3.41 (m, 1H), 3.32 (dd, J=14.9, 8.7 Hz, 1H), 3.09 (d, J=11.3 Hz, 2H), 2.86 (hept, J=6.9 Hz, 7H), 2.65 (d, J=6.2 Hz, 2H), 2.40 (q, J=15.4 Hz, 2H), 2.04 (d, J=10.3 Hz, 1H), 1.99-1.83 (m, 3H), 1.27-1.12 (m, 9H).

Example 132: Synthesis of 2-[(2R)-3-(3,4-dihydro-1H-isoquinolin-2-yl)-2-hydroxy-propyl]-4,4-difluoro-6-morpholino-3H-isoquinolin-1-one

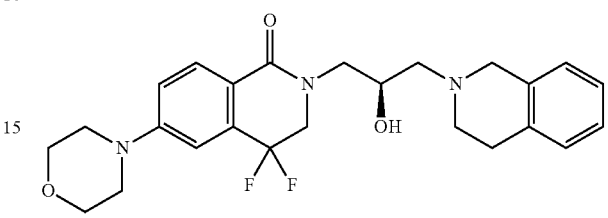

Example 132-1: Synthesis of 6-Bromo-2-[(2R)-3-(3,4-dihydro-1H-isoquinolin-2-yl)-2-hydroxy-propyl]-4,4-difluoro-3H-isoquinolin-1-one The title compound was synthesized in the same manner as in Example 1, except that 6-bromo-4,4-difluoro-2,3-dihydroisoquinolin-1-one was used instead of 6-bromo-3,4-dihydro-2H-isoquinolin-1-one.

Example 132-2: Synthesis of 2-[(2R)-3-(3,4-dihydro-1H-isoquinolin-2-yl)-2-hydroxy-propyl]-4,4-difluoro-6-morpholino-3H-isoquinolin-1-one 6-Bromo-2-[(2R)-3-(3,4-dihydro-1H-isoquinolin-2-yl)-2-hydroxy-propyl]-4,4-difluoro-3H-isoquinolin-1-one obtained in Example 132-1 as a starting material was used in the same manner as in Example 2 to obtain the title compound, except that morpholine was used instead of pyrrolidine.

¹H NMR (400 MHz, Methanol-d₄) δ 7.95 (d, J=8.8 Hz, 1H), 7.30 (q, J=7.8, 7.3 Hz, 3H), 7.25-7.14 (m, 3H), 4.62 (s, 1H), 4.56-4.34 (m, 3H), 4.19 (td, J=12.5, 11.1, 3.9 Hz, 2H), 3.86 (t, J=4.9 Hz, 5H), 3.82-3.65 (m, 3H), 3.37 (d, J=4.8 Hz, 6H).

Example 133: Synthesis of 2-[(2R)-3-(3,4-dihydro-1H-isoquinolin-2-yl)-2-hydroxy-propyl]-6-(1-methylpyrrolidin-3-yl)oxy-3,4-dihydroisoquinolin-1-one

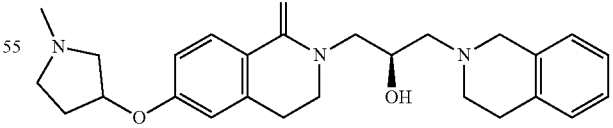

Example 133-1: Synthesis of tert-butyl 3-[[2-[(2R)-3-(3,4-dihydro-1H-isoquinolin-2-yl)-2-hydroxy-propyl]-1-oxo-3,4-dihydroisoquinolin-6-yl]oxy]pyrrolidine-1-carboxylate The title compound was synthesized in the same manner as in Example 83, except that tert-butyl 3-methylsulfony- Example 133-2: Synthesis of 2-[(2R)-3-(3,4-di-hydro-1H-isoquinolin-2-yl)-2-hydroxy-propyl]-6-pyrrolidin-3-yloxy-3,4-dihydroisoquinolin-1-one Tert-butyl 3-[[2-[(2R)-3-(3,4-dihydro-1H-isoquinolin-2-yl)-2-hydroxy-propyl]-1-oxo-3,4-dihydroisoquinolin-6-yl]oxy]pyrrolidine-1-carboxylate obtained in Example 133-1 as a starting material was used in the same manner as in Example 57 to obtain the title compound.

Example 133-3: Synthesis of 2-[(2R)-3-(3,4-di-hydro-1H-isoquinolin-2-yl)-2-hydroxy-propyl]-6-(1-methylpyrrolidin-3-yl)oxy-3,4-dihydroisoquinolin-1-one 2-[(2R)-3-(3,4-dihydro-1H-isoquinolin-2-yl)-2-hydroxy-propyl]-6-pyrrolidin-3-yloxy-3,4-dihydroisoquinolin-1-one obtained in Example 133-2 as a starting material was used in the same manner as in Example 114-3 to obtain the title compound, except that paraformaldehyde was used instead of acetaldehyde.

$^1$H NMR (400 MHz, Methanol-$d_4$) δ 7.88 (d, J=8.6 Hz, 1H), 7.17-7.00 (m, 4H), 6.86 (d, J=8.7 Hz, 1H), 6.77 (s, 1H), 5.00 (s, 1H), 4.23 (s, 1H), 3.89 (dd, J=13.8, 4.1 Hz, 1H), 3.84-3.64 (m, 4H), 3.41-3.35 (m, 1H), 3.06-2.97 (m, 2H), 2.97-2.81 (m, 7H), 2.70-2.60 (m, 2H), 2.55-2.35 (m, 5H), 2.08-1.93 (m, 1H).

Example 134: Synthesis of 2-[(2R)-3-(3,4-dihydro-1H-isoquinolin-2-yl)-2-hydroxy-propyl]-6-(1-ethylpyrrolidin-3-yl)oxy-3,4-dihydroisoquinolin-1-one

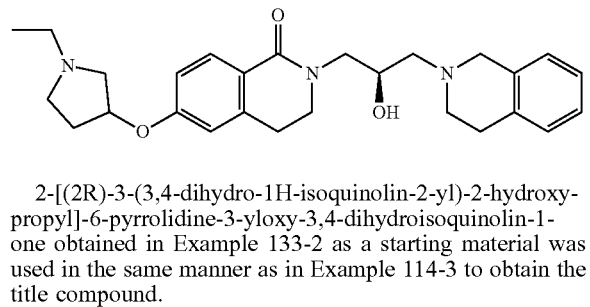

2-[(2R)-3-(3,4-dihydro-1H-isoquinolin-2-yl)-2-hydroxy-propyl]-6-pyrrolidine-3-yloxy-3,4-dihydroisoquinolin-1-one obtained in Example 133-2 as a starting material was used in the same manner as in Example 114-3 to obtain the title compound.

$^1$H NMR (400 MHz, Methanol-$d_4$) δ 7.88 (d, J=8.6 Hz, 1H), 7.18-7.00 (m, 4H), 6.86 (d, J=8.7 Hz, 1H), 6.77 (s, 1H), 5.01 (d, J=8.3 Hz, 1H), 4.23 (s, 1H), 3.93-3.84 (m, 1H), 3.84-3.66 (m, 4H), 3.41-3.34 (m, 1H), 3.05-2.97 (m, 2H), 2.96-2.84 (m, 6H), 2.70-2.49 (m, 5H), 2.41 (dq, J=14.2, 7.2 Hz, 1H), 2.10-1.89 (m, 2H), 1.17 (t, J=7.3 Hz, 3H).

Example 135: Synthesis of 2-[(2R)-3-(3,4-dihydro-1H-isoquinolin-2-yl)-2-hydroxy-propyl]-6-[(1-methyl-4-piperidyl)oxy]-3,4-dihydroisoquinolin-1-one

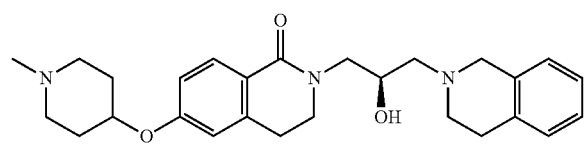 [SMILES: CN1CCC(Oc2ccc3c(c2)CCN(C[C@H](O)CN2CCc4ccccc4C2)C3=O)CC1]

2-[(2R)-3-(3,4-dihydro-1H-isoquinolin-2-yl)-2-hydroxy-propyl]-6-(4-piperidyloxy)-3,4-dihydroisoquinolin-1-one obtained in Example 114-2 as a starting material was used in the same manner as in Example 114-3 to obtain the title compound, except that paraformaldehyde was used instead of acetaldehyde.

$^1$H NMR (400 MHz, Methanol-$d_4$) δ 7.93-7.81 (m, 1H), 7.16-6.99 (m, 4H), 6.91 (dd, J=8.6, 2.4 Hz, 1H), 6.82 (s, 1H), 4.54 (s, 1H), 4.22 (dd, J=8.4, 4.1 Hz, 1H), 3.89 (dd, J=13.9, 4.1 Hz, 1H), 3.83-3.64 (m, 4H), 3.41-3.34 (m, 1H), 2.99 (t, J=6.9 Hz, 2H), 2.92 (t, J=6.0 Hz, 2H), 2.86 (t, J=5.9 Hz, 2H), 2.73 (s, 2H), 2.67-2.58 (m, 2H), 2.42 (t, J=10.2 Hz, 2H), 2.33 (d, J=1.7 Hz, 3H), 2.05 (t, J=9.6 Hz, 2H), 1.83 (q, J=9.8, 9.1 Hz, 2H).

Example 136: Synthesis of 2-[(2R)-3-(3,4-dihydro-1H-isoquinolin-2-yl)-2-hydroxy-propyl]-6-[[1-(oxetan-3-yl)-4-piperidyl]oxy]-3,4-dihydroisoquinolin-1-one

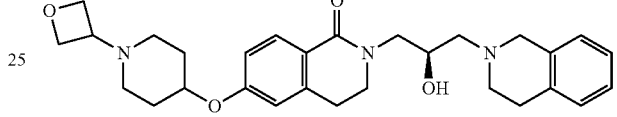

2-[(2R)-3-(3,4-dihydro-1H-isoquinolin-2-yl)-2-hydroxy-propyl]-6-(4-piperidyloxy)-3,4-dihydroisoquinolin-1-one obtained in Example 114-2 as a starting material was used in the same manner as in Example 114-3 to obtain the title compound, except that oxetan-3-one was used instead of acetaldehyde.

$^1$H NMR (400 MHz, Methanol-$d_4$) δ 7.87 (d, J=8.6 Hz, 1H), 7.17-7.02 (m, 4H), 6.91 (d, J=8.6 Hz, 1H), 6.82 (s, 1H), 4.71 (t, J=6.7 Hz, 2H), 4.67-4.52 (m, 3H), 4.24 (d, J=7.8 Hz, 1H), 3.89 (dd, J=13.5, 3.7 Hz, 1H), 3.83-3.65 (m, 4H), 3.55 (p, J=6.8 Hz, 1H), 3.43-3.36 (m, 1H), 3.05-2.97 (m, 2H), 2.97-2.87 (m, 4H), 2.73-2.56 (m, 4H), 2.30 (d, J=10.3 Hz, 2H), 2.05 (d, J=11.0 Hz, 2H), 1.85 (s, 2H).

Example 137: Synthesis of 2-[(2R)-3-(3,4-dihydro-1H-isoquinolin-2-yl)-2-hydroxypropyl]-6-(3-hydroxyprop-1-ynyl)-3,4-dihydroisoquinolin-1-one

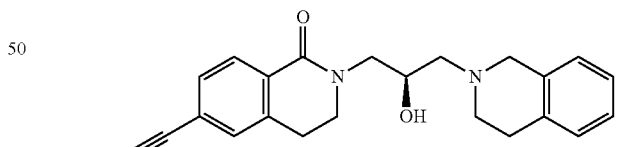

6-Bromo-2-[(2R)-3-(3,4-dihydro-1H-isoquinolin-2-yl)-2-hydroxy-propyl]-3,4-dihydroisoquinolin-1-one (83 mg, 0.2 mmol), copper iodide (4 mg, 0.02 mmol), bis(triphenylphosphine) palladium(II) dichloride (7 mg, 0.01 mmol), triethylamine (115 μl, 0.6 mmol) and prop-2-yn-1-ol (35 μl, 0.6 mmol) were dissolved in dimethylformamide and reacted at 80° C. for one day. After completion of the reaction, the reaction mixture was diluted with ethyl acetate and filtered through Celite. The solvent was dried under reduced pressure, and the purification was carried out by flash chromatography to obtain 12.5 mg of the title compound.

¹H NMR (400 MHz, Chloroform-d) δ 8.00 (d, J=8.0 Hz, 1H), 7.39 (dd, J=8.1, 1.6 Hz, 1H), 7.20-7.09 (m, 4H), 7.02 (d, J=6.8 Hz, 1H), 4.51 (s, 2H), 4.22-4.07 (m, 1H), 3.94-3.60 (m, 6H), 3.47 (dd, J=14.0, 6.3 Hz, 1H), 2.98 (p, J=9.2 Hz, 4H), 2.83 (d, J=10.9 Hz, 1H), 2.73 (dd, J=12.5, 3.8 Hz, 1H), 2.63 (t, J=11.2 Hz, 1H).

Example 138: Synthesis of 2-[(2R)-3-(3,4-dihydro-1H-isoquinolin-2-yl)-2-hydroxypropyl]-6-[2-(4-pyridyl)ethynyl]-3,4-dihydroisoquinolin-1-one

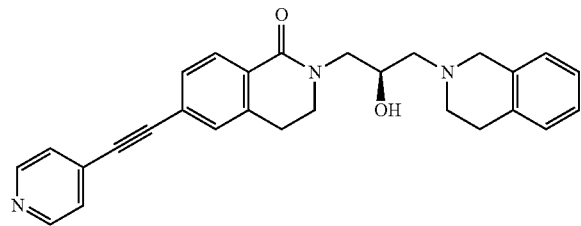 [SMILES: O=C1c2ccc(C#Cc3ccncc3)cc2CCN1C[C@H](O)CN1CCc2ccccc2C1]

The title compound was synthesized in the same manner as in Example 137, except that 4-ethynylpyridine was used instead of prop-2-yn-1-ol.

¹H NMR (400 MHz, Chloroform-d) δ 8.66-8.60 (m, 2H), 8.08 (d, J=8.0 Hz, 1H), 7.53 (dd, J=8.0, 1.6 Hz, 1H), 7.43-7.31 (m, 3H), 7.14 (qd, J=7.8, 6.9, 3.8 Hz, 3H), 7.05-6.98 (m, 1H), 4.21-4.07 (m, 1H), 3.98-3.60 (m, 5H), 3.46 (dd, J=13.9, 6.4 Hz, 1H), 3.07-2.86 (m, 5H), 2.78 (dd, J=10.4, 5.1 Hz, 1H), 2.69 (dd, J=12.5, 3.9 Hz, 1H), 2.63-2.53 (m, 1H).

Example 139: Synthesis of 2-[(2R)-3-(3,4-dihydro-1H-isoquinolin-2-yl)-2-hydroxypropyl]-6-[(1-methyl-3-piperidyl)oxy]-3,4-dihydroisoquinolin-1-one

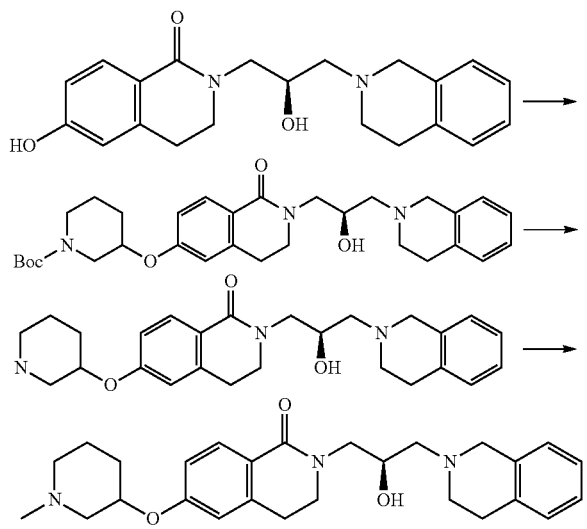

Example 139-1: Synthesis of tert-butyl 3-[[2-[(2R)-3-(3,4-dihydro-1H-isoquinolin-2-yl)-2-hydroxypropyl]-1-oxo-3,4-dihydroisoquinolin-6-yl]oxy]piperidine-1-carboxylate The title compound was synthesized in the same manner as in Example 83, except that tert-butyl 3-methylsulfonyloxypepyridine-1-carboxylate was used instead of (1-acetyl-4-piperidyl)methyl methanesulfonate Example 139-2: Synthesis of 2-[(2R)-3-(3,4-dihydro-1H-isoquinolin-2-yl)-2-hydroxypropyl]-6-(3-piperidyloxy)-3,4-dihydroisoquinolin-1-one dihydrochloride Tert-butyl 3-[[2-[(2R)-3-(3,4-dihydro-1H-isoquinolin-2-yl)-2-hydroxypropyl]-1-oxo-3,4-dihydroisoquinolin-6-yl]oxy]piperidine-1-carboxylate obtained in Example 139-1 as a starting material was used in the same manner as in Example 57 to obtain the title compound.

Example 139-3: Synthesis of 2-[(2R)-3-(3,4-dihydro-1H-isoquinolin-2-yl)-2-hydroxypropyl]-6-[(1-methyl-3-piperidyl)oxy]-3,4-dihydroisoquinolin-1-one 2-[(2R)-3-(3,4-dihydro-1H-isoquinolin-2-yl)-2-hydroxypropyl]-6-(3-piperidyloxy)-3,4-dihydroisoquinolin-1-one dihydrochloride obtained in Example 139-2 as a starting material was used in the same manner as in Example 114-3 to obtain the title compound, except that paraformaldehyde was used instead of acetaldehyde.

¹H NMR (400 MHz, Methanol-d₄) δ 7.88 (d, J=8.6 Hz, 1H), 7.18-7.02 (m, 4H), 6.92 (dd, J=8.7, 2.5 Hz, 1H), 6.85 (d, J=2.5 Hz, 1H), 4.57 (dq, J=7.9, 3.8 Hz, 1H), 4.24 (tt, J=7.5, 4.7 Hz, 1H), 3.89 (dd, J=13.8, 4.2 Hz, 1H), 3.84-3.65 (m, 4H), 3.40-3.35 (m, 2H), 3.04-2.85 (m, 7H), 2.68-2.59 (m, 3H), 2.36 (s, 4H), 2.06-1.84 (m, 2H), 1.67 (ddd, J=17.8, 9.0, 4.3 Hz, 2H).

Example 140: Synthesis of 2-[(2R)-3-(3,4-dihydro-1H-isoquinolin-2-yl)-2-hydroxypropyl]-6-[[1-(2-fluoroethyl)-3-piperidyl]oxy]-3,4-dihydroisoquinolin-1-one 2-[(2R)-3-(3,4-dihydro-1H-isoquinolin-2-yl)-2-hydroxypropyl]-6-(3-piperidyloxy)-3,4-dihydroisoquinolin-1-one dihydrochloride (101 mg, 0.2 mmol) obtained in Example 139-2, potassium carbonate (83 mg, 0.6 mmol) and 2-fluoroethyl 4-methylbenzenesulfonate (52 mg, 0.24 mmol) were dissolved in acetonitrile and stirred at 80° C. for one day. A saturated aqueous ammonium chloride solution was added to the reaction mixture, and the reaction mixture was extracted three times with ethyl acetate. The combined organic layers were dried over anhydrous sodium sulfate, concentrated under reduced pressure, and the concentrated oily liquid was purified by flash chromatography to obtain the title compound (5.1 mg).

¹H NMR (400 MHz, Methanol-d₄) δ 7.89 (d, J=8.6 Hz, 1H), 7.24 (qd, J=9.4, 8.8, 4.5 Hz, 3H), 7.15 (d, J=7.0 Hz, 1H), 7.02-6.90 (m, 1H), 6.87 (d, J=2.5 Hz, 1H), 4.72-4.64 (m, 1H), 4.62-4.50 (m, 2H), 4.38 (s, 1H), 4.24 (s, 1H), 3.86-3.70 (m, 3H), 3.52 (dd, J=13.9, 6.5 Hz, 1H), 3.36 (d, J=7.7 Hz, 1H), 3.08 (ddd, J=28.2, 13.0, 6.2 Hz, 6H), 2.90-2.78 (m, 2H), 2.46 (dt, J=28.0, 10.3 Hz, 2H), 2.09-1.85 (m, 4H), 1.75-1.50 (m, 4H).

Example 141: Synthesis of 2-[(2R)-3-(3,4-dihydro-1H-isoquinolin-2-yl)-2-hydroxypropyl]-6-[3-(dimethylamino)prop-1-ynyl]-3,4-dihydroisoquinolin-1-one

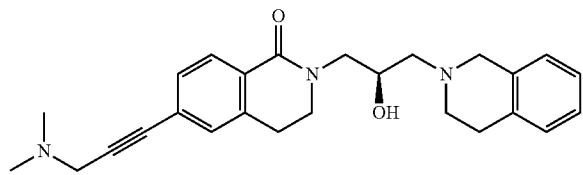 [SMILES: CN(C)CC#Cc1ccc2c(c1)CCN(C[C@H](O)CN1CCc3ccccc3C1)C2=O]

The title compound was synthesized in the same manner as in Example 137, except that N,N-dimethylprop-2-yn-1-amine was used instead of pyrrolidin-2-one.

$^1$H NMR (400 MHz, Methanol-$d_4$) δ 7.91 (d, J=8.0 Hz, 1H), 7.41 (dd, J=8.1, 1.6 Hz, 1H), 7.36 (d, J=1.5 Hz, 1H), 7.18-7.08 (m, 3H), 7.08-7.02 (m, 1H), 4.26 (tt, J=7.4, 4.6 Hz, 1H), 3.90 (dd, J=13.8, 4.1 Hz, 1H), 3.86-3.67 (m, 4H), 3.45-3.39 (m, 1H), 3.37 (s, 2H), 3.07-2.98 (m, 2H), 2.93 (dp, J=9.5, 5.3, 4.7 Hz, 4H), 2.74-2.63 (m, 2H), 2.41 (s, 6H).

Example 142: Synthesis of 2-[(2R)-3-(3,4-dihydro-1H-isoquinolin-2-yl)-2-hydroxy-propyl]-6-[[1-(2-methoxyethyl)-4-piperidyl]oxy]-3,4-dihydroisoquinolin-1-one

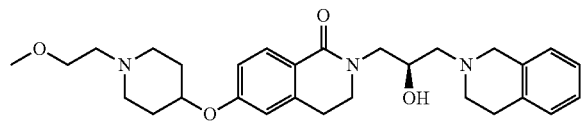 [SMILES: COCCN1CCC(Oc2ccc3c(c2)CCN(C[C@H](O)CN2CCc4ccccc4C2)C3=O)CC1]

2-[(2R)-3-(3,4-dihydro-1H-isoquinolin-2-yl)-2-hydroxypropyl]-6-(4-piperidyloxy)-3,4-dihydroisoquinolin-1-one obtained in Example 114-2 as a starting material was used in the same manner as in Example 140 to obtain the title compound, except that 1-bromo-2-methoxy-ethane was used instead of 2-fluoroethyl 4-methylbenzenesulfonate.

$^1$H NMR (400 MHz, Methanol-$d_4$) δ 7.87 (d, J=8.7 Hz, 1H), 7.16-7.05 (m, 3H), 7.04 (dd, J=6.8, 2.2 Hz, 1H), 6.90 (dd, J=8.7, 2.4 Hz, 1H), 6.81 (d, J=2.4 Hz, 1H), 4.52 (tt, J=7.7, 3.8 Hz, 1H), 4.28-4.17 (m, 1H), 3.89 (dd, J=13.8, 4.1 Hz, 1H), 3.82-3.63 (m, 4H), 3.56 (t, J=5.5 Hz, 2H), 3.36 (m, 4H), 3.03-2.91 (m, 2H), 2.91 (d, J=5.4 Hz, 2H), 2.84 (dd, J=14.7, 7.2 Hz, 4H), 2.70-2.56 (m, 4H), 2.52-2.42 (m, 2H), 2.04 (ddt, J=10.9, 7.3, 3.6 Hz, 2H), 1.82 (dtd, J=12.2, 8.0, 3.4 Hz, 2H).

Example 143: Synthesis of 6-[(2R)-3-(3,4-dihydro-1H-isoquinolin-2-yl)-2-hydroxypropyl]-2-[[1-(2-methoxyethyl)-4-piperidyl]oxy]-7,8-dihydro-1,6-naphthyridin-5-one

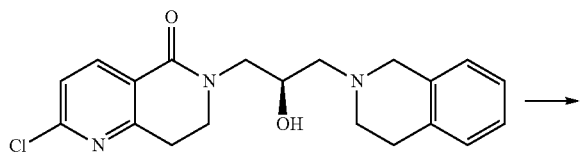

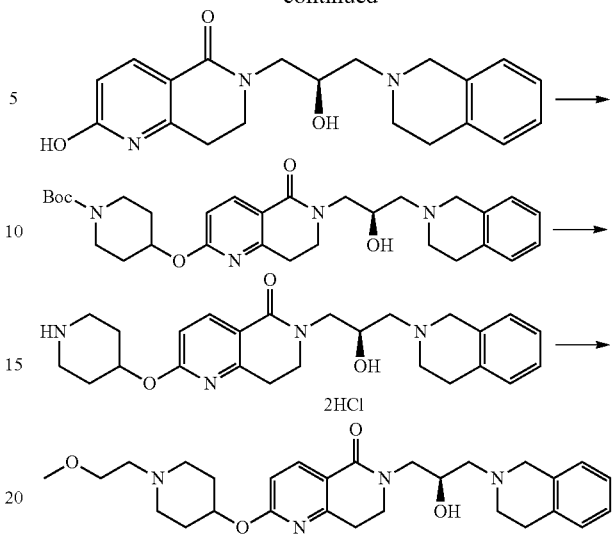

Example 143-1: Synthesis of 6-[(2R)-3-(3,4-dihydro-1H-isoquinolin-2-yl)-2-hydroxypropyl]-2-hydroxy-7,8-dihydro-1,6-naphthyridin-5-one The title compound was synthesized in the same manner as in Example 74, except that 2-chloro-6-[(2R)-3-(3,4-dihydro-1H-isoquinolin-2-yl)-2-hydroxy-propyl]-7,8-dihydro-1,6-naphthyridin-5-one was used instead of 6-bromo-2-[(2R)-3-(3,4-dihydro-1H-isoquinolin-2-yl)-2-hydroxy-propyl]-3,4-dihydroisoquinolin-1-one.

Example 143-2: Synthesis of tert-butyl 4-[[6-[(2R)-3-(3,4-dihydro-1H-isoquinolin-2-yl)-2-hydroxypropyl]-5-oxo-7,8-dihydro-1,6-naphthyridin-2-yl]oxy]piperidine-1-carboxylate 6-[(2R)-3-(3,4-dihydro-1H-isoquinolin-2-yl)-2-hydroxypropyl]-2-hydroxy-7,8-dihydro-1,6-naphthyridin-5-one obtained in Example 143-1 as a starting material was used in the same manner as in Example 114-1 to obtain the title compound.

Example 143-3: Synthesis of 6-[(2R)-3-(3,4-dihydro-1H-isoquinolin-2-yl)-2-hydroxypropyl]-2-(4-piperidyloxy)-7,8-dihydro-1,6-naphthyridin-5-one dihydrochloride Tert-butyl 4-[[6-[(2R)-3-(3,4-dihydro-1H-isoquinolin-2-yl)-2-hydroxypropyl]-5-oxo-7,8-dihydro-1,6-naphthyridin-2-yl]oxy]piperidine-1-carboxylate obtained in Example 143-2 as a starting material was used in the same manner as in Example 57 to obtain the title compound.

Example 143-4: Synthesis of 6-[(2R)-3-(3,4-dihydro-1H-isoquinolin-2-yl)-2-hydroxypropyl]-2-[[1-(2-methyloxyethyl)-4-piperidyl]oxy]-7,8-dihydro-1,6-naphthyridin-5-one 6-[(2R)-3-(3,4-dihydro-1H-isoquinolin-2-yl)-2-hydroxypropyl]-2-(4-piperidyloxy)-7,8-dihydro-1,6-naphthyridin-5-one dihydrochloride obtained in Example 143-3 as a starting material was used in the same manner as in Example 140 to obtain the title compound, except that 1-bromo-2-methoxyethane was used instead of 2-fluoroethyl 4-methylbenzenesulfonate.

$^1$H NMR (400 MHz, Methanol-$d_4$) δ 8.10 (d, J=8.6 Hz, 1H), 7.10 (dq, J=7.4, 4.4, 3.3 Hz, 3H), 7.05-6.99 (m, 1H), 6.70 (d, J=8.6 Hz, 1H), 5.17 (tt, J=8.2, 4.0 Hz, 1H), 4.22 (ddd, J=9.7, 7.3, 4.7 Hz, 1H), 3.91-3.73 (m, 3H), 3.72 (s, 2H), 3.56 (t, J=5.6 Hz, 2H), 3.36 (m, 4H), 3.05 (t, J=7.0 Hz, 2H), 2.86 (dt, J=18.5, 6.5 Hz, 6H), 2.69-2.56 (m, 4H), 2.50-2.39 (m, 2H), 2.07 (dtd, J=14.9, 7.5, 3.9 Hz, 2H), 1.84 (dtd, J=12.6, 8.5, 3.5 Hz, 2H).

Example 144: Synthesis of 6-[(2R)-3-(3,4-dihydro-1H-isoquinolin-2-yl)-2-hydroxypropyl]-2-[[1-[(2R)-2-hydroxypropyl]-4-piperidyl]oxy]-7,8-dihydro-1,6-naphthyridin-5-one

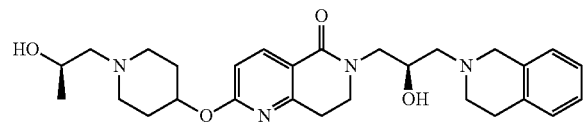 [SMILES: C[C@@H](O)CN1CCC(Oc2ccc3c(n2)CCN(C[C@H](O)CN2CCc4ccccc4C2)C3=O)CC1]

6-[(2R)-3-(3,4-dihydro-1H-isoquinolin-2-yl)-2-hydroxypropyl]-2-(4-piperidyloxy)-7,8-dihydro-1,6-naphthyridin-5-one dihydrochloride obtained in Example 143-3 as a starting material was used in the same manner as in Example 140 to obtain the title compound, except that (2R)-2-methyloxirane was used instead of 2-fluoroethyl 4-methylbenzenesulfonate.

$^1$H NMR (400 MHz, Methanol-$d_4$) δ 8.12 (d, J=8.6 Hz, 1H), 7.16-7.01 (m, 4H), 6.72 (d, J=8.6 Hz, 1H), 5.19 (dt, J=8.2, 4.1 Hz, 1H), 4.23 (dq, J=7.5, 4.6, 3.8 Hz, 1H), 4.03-3.74 (m, 6H), 3.39 (dd, J=13.8, 7.7 Hz, 1H), 3.07 (t, J=6.9 Hz, 2H), 2.95-2.83 (m, 6H), 2.71-2.58 (m, 2H), 2.42 (dq, J=13.2, 8.6, 7.1 Hz, 4H), 2.09 (m, 2H), 1.87 (m, 2H), 1.17 (d, J=6.2 Hz, 4H).

Example 145: Synthesis of 6-[(2R)-3-(3,4-dihydro-1H-isoquinolin-2-yl)-2-hydroxypropyl]-2-[[1-(2-hydroxy-2-methyl-propyl)-4-piperidyl]oxy]-7,8-dihydro-1,6-naphthyridin-5-one

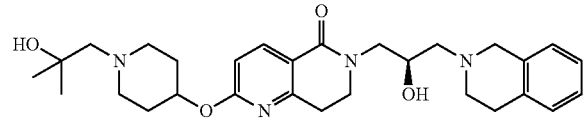 [SMILES: CC(C)(O)CN1CCC(Oc2ccc3c(n2)CCN(C[C@H](O)CN2CCc4ccccc4C2)C3=O)CC1]

6-[(2R)-3-(3,4-dihydro-1H-isoquinolin-2-yl)-2-hydroxypropyl]-2-(4-piperidyloxy)-7,8-dihydro-1,6-naphthyridin-5-one dihydrochloride obtained in Example 143-3 as a starting material was used in the same manner as in Example 140 to obtain the title compound, except that 2,2-dimethyloxirane was used instead of 2-fluoroethyl 4-methylbenzenesulfonate.

$^1$H NMR (400 MHz, Methanol-$d_4$) δ 8.11 (d, J=8.6 Hz, 1H), 7.17-7.06 (m, 3H), 7.04 (dd, J=6.9, 2.4 Hz, 1H), 6.70 (d, J=8.6 Hz, 1H), 5.14 (tt, J=8.3, 4.0 Hz, 1H), 4.28-4.18 (m, 1H), 3.92-3.76 (m, 3H), 3.74 (s, 2H), 3.38 (dd, J=13.8, 7.7 Hz, 1H), 3.06 (t, J=7.0 Hz, 2H), 2.97-2.82 (m, 6H), 2.65 (d, J=1.7 Hz, 1H), 2.66-2.58 (m, 1H), 2.58-2.48 (m, 2H), 2.37 (s, 2H), 2.05 (dq, J=13.0, 6.8, 5.2 Hz, 2H), 1.83 (dtd, J=12.7, 8.9, 3.5 Hz, 2H), 1.21 (s, 6H).

Example 146: Synthesis of 6-[(2R)-3-(3,4-dihydro-1H-isoquinolin-2-yl)-2-hydroxypropyl]-2-[[1-(oxetan-3-yl)-4-piperidyl]oxy]-7,8-dihydro-1,6-naphthyridin-5-one

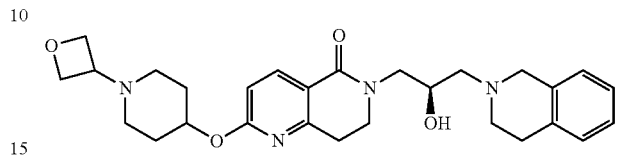

6-[(2R)-3-(3,4-dihydro-1H-isoquinolin-2-yl)-2-hydroxypropyl]-2-(4-piperidyloxy)-7,8-dihydro-1,6-naphthyridin-5-one dihydrochloride obtained in Example 143-3 as a starting material was used in the same manner as in Example 114-3 to obtain the title compound, except that oxetan-3-one was used instead of acetaldehyde.

$^1$H NMR (400 MHz, Methanol-$d_4$) δ 8.11 (d, J=8.6 Hz, 1H), 7.16-7.05 (m, 3H), 7.05-7.00 (m, 1H), 6.70 (d, J=8.6 Hz, 1H), 5.21 (tt, J=7.9, 3.9 Hz, 1H), 4.70 (t, J=6.7 Hz, 2H), 4.61 (t, J=6.2 Hz, 2H), 4.22 (ddd, J=9.5, 7.4, 4.7 Hz, 1H), 3.91-3.73 (m, 3H), 3.73 (s, 2H), 3.53 (p, J=6.4 Hz, 1H), 3.37 (dd, J=13.8, 7.7 Hz, 1H), 3.05 (t, J=7.0 Hz, 2H), 2.91 (t, J=6.2 Hz, 2H), 2.84 (dd, J=8.9, 3.8 Hz, 2H), 2.70-2.56 (m, 4H), 2.29-2.20 (m, 2H), 2.09 (ddt, J=14.0, 7.3, 3.6 Hz, 2H), 1.85 (dtd, J=12.4, 8.4, 3.5 Hz, 2H).

Experimental Example

Method for Measuring Enzyme Activity

In vitro assay: PRMT5-MEP50 enzyme complex, cofactor S-adenosylmethionine (SAM) and histone H4 peptide were reacted in vitro, and methylation of arginine (H4R3)—which is the third amino acid of histone H4—was measured in order to measure the enzyme activity of PRMT5.

Reagents: PRMT5-MEP50 enzyme complex (Catalog No. 51045), blocking buffer (52100-B), histone methyltransferase reaction buffer 2 (4×HMT assay buffer 2, Catalog No. 52170), and primary antibody (primary antibody 4-3, Catalog No. 52150) were purchased from BPS Bioscience (USA). The histone H4 peptide (1-20 amino acids) was custom made by Komabiotech (Korea) and used. S-adenosylmethionine was purchased from NEB (New England Biolabs, USA, Catalog No. B9003S). Plates for coating histone H4 peptide, washing buffer and color development reagent were purchased from the following vendors: Plate (Immobilizer™-Amino Plate, NUNC, Denmark, Catalog No. 436023), carbonate-bicarbonate buffer (Sigma-Aldrich, USA, Catalog No. C3041), washing buffer (10×TBST, Biosesang, Korea, Catalog No. T2005), TMB ELISA substrate (Abcam, UK, Catalog No. ab210902), horseradish peroxidase (HRP)-conjugated antibody (Abcam, UK, Catalog No. ab6721).

Experimental procedure: The histone H4 peptide was diluted with carbonate-bicarbonate buffer and prepared to 100 μg/mL, and then dispensed onto the plate per 100 μL and reacted at 37° C. for 1 hour. PRMT5-MEP50 enzyme complex and S-adenosylmethionine were diluted with histone methyltransferase reaction buffer to prepare 5 μg/mL and 2 μM, respectively, and then 20 μL of PRMT5-MEP50 enzyme complex and 25 μL of S-adenosylmethionine were dispensed onto the plate prepared above. 5 μL of the compound diluted with 10% dimethyl sulfoxide solution was added thereto and reacted at room temperature for 2 hours (final volume=50 μL). The concentration of the compound was diluted 1:5 from 10 μM until the lowest concentration of 0.128 nM, and 8 points were used for the test. After preparing the primary antibody by diluting 1:2000 with blocking buffer, 100 μL was added to the plate and reacted at room temperature for 1 hour. After preparing horseradish peroxidase-conjugated antibody by diluting 1:10,000 with blocking buffer, 100 μL was added to the plate and reacted at room temperature for 1 hour. 100 μL of TMB substrate was added and reacted for 3 minutes at room temperature, and 100 μL of 1 N sulfuric acid was then added to terminate the reaction. Then, the absorbance at 450 nm was measured to calculate the $IC_{50}$ value of the compound. (+++: 1 to 100 nM, ++: greater than 100 to 1,000 nM, +: greater than 1,000 to 10,000 nM)

TABLE 2

| Compound | PRMT5 enzyme $IC_{50}$ (nM) |
|---|---|
| Example 1 | +++ |
| Example 2 | ++ |
| Example 4 | +++ |
| Example 5 | +++ |
| Example 6 | +++ |
| Example 7 | +++ |
| Example 8 | +++ |
| Example 9 | +++ |
| Example 10 | +++ |
| Example 11 | +++ |
| Example 12 | +++ |
| Example 13 | +++ |
| Example 14 | ++ |
| Example 15 | +++ |
| Example 16 | +++ |
| Example 17 | +++ |
| Example 18 | + |
| Example 19 | ++ |
| Example 20 | ++ |
| Example 21 | ++ |
| Example 22 | + |
| Example 23 | +++ |
| Example 24 | +++ |
| Example 25 | +++ |
| Example 26 | +++ |
| Example 27 | ++ |
| Example 28 | ++ |
| Example 29 | +++ |
| Example 30 | +++ |
| Example 31 | +++ |
| Example 32 | +++ |
| Example 33 | +++ |
| Example 34 | + |
| Example 35 | +++ |
| Example 36 | +++ |
| Example 37 | +++ |
| Example 38 | ++ |
| Example 39 | ++ |
| Example 40 | + |
| Example 41 | +++ |
| Example 42 | ++ |
| Example 43 | + |
| Example 44 | +++ |
| Example 45 | ++ |
| Example 46 | ++ |
| Example 47 | +++ |
| Example 48 | +++ |
| Example 49 | +++ |
| Example 50 | ++ |
| Example 51 | ++ |
| Example 52 | ++ |
| Example 53 | +++ |
| Example 54 | +++ |
| Example 55 | +++ |
| Example 56 | +++ |
| Example 57 | +++ |
| Example 58 | +++ |
| Example 59 | ++ |
| Example 60 | ++ |
| Example 61 | +++ |
| Example 62 | +++ |
| Example 63 | ++ |
| Example 64 | +++ |
| Example 65 | + |
| Example 66 | +++ |
| Example 67 | + |
| Example 68 | +++ |
| Example 69 | ++ |
| Example 70 | +++ |
| Example 71 | +++ |
| Example 72 | ++ |
| Example 73 | ++ |
| Example 75 | ++ |
| Example 76 | ++ |
| Example 77 | ++ |
| Example 78 | +++ |
| Example 79 | +++ |
| Example 80 | +++ |
| Example 81 | +++ |
| Example 82 | +++ |
| Example 83 | ++ |
| Example 84 | ++ |
| Example 85 | ++ |
| Example 86 | ++ |
| Example 87 | +++ |
| Example 88 | +++ |
| Example 89 | +++ |
| Example 90 | +++ |
| Example 91 | +++ |
| Example 92 | ++ |
| Example 93 | +++ |
| Example 94 | +++ |
| Example 95 | ++ |
| Example 96 | ++ |
| Example 97 | ++ |
| Example 98 | ++ |
| Example 99 | ++ |
| Example 101 | +++ |
| Example 102 | +++ |
| Example 103 | +++ |
| Example 104 | +++ |
| Example 105 | +++ |
| Example 106 | +++ |
| Example 107 | ++ |
| Example 108 | ++ |
| Example 109 | ++ |
| Example 110 | ++ |
| Example 111 | ++ |
| Example 112 | ++ |
| Example 113 | +++ |
| Example 114 | ++ |
| Example 115 | ++ |
| Example 116 | ++ |
| Example 117 | ++ |
| Example 118 | ++ |
| Example 119 | ++ |
| Example 120 | +++ |
| Example 121 | ++ |
| Example 122 | ++ |
| Example 123 | ++ |
| Example 124 | +++ |
| Example 125 | ++ |
| Example 126 | +++ |
| Example 127 | +++ |
| Example 128 | ++ |
| Example 129 | ++ |
| Example 130 | + |
| Example 131 | +++ |
| Example 132 | + |
| Example 133 | +++ |
| Example 134 | ++ |

TABLE 2-continued

| Compound | PRMT5 enzyme IC$_{50}$ (nM) |
|---|---|
| Example 135 | ++ |
| Example 136 | +++ |
| Example 137 | ++ |
| Example 138 | ++ |
| Example 139 | +++ |
| Example 140 | ++ |
| Example 141 | ++ |

Test for In Vivo Target Inhibitory Activity

After U87MG tumor cells were implanted subcutaneously in nude mice, a PRMT5 inhibitor was administered orally (25 or 50 mg/kg) 1-2 times daily for one week, and then the degree to which SDMA levels in the tumor decreased was measured.

Reagents: Bradford's solution (Catalog No. 500-0006) was purchased from Bio-rad (USA). SDMA antibody (Catalog No. 13222s) was purchased from Cell Signaling Technology (USA). SmD3 antibody (Catalog No. ap12451a) was purchased from Abgent (USA), and secondary antibody (Catalog No. ab6721) and TMB substrate (Catalog No. ab210902) were purchased from Abcam (UK).

Experimental procedure: The tumor tissues transplanted into the mice were excised, the cells were lysed, and then quantified with Bradford's solution. 5-10 µg of protein per sample was diluted with carbonate-bicarbonate buffer and dispensed into a 96-well plate and reacted at room temperature for 2 hours. After washing with phosphate buffered saline (PBST) containing 0.05% Tween-20 3 times, 200 µL of PBST containing 5% bovine serum albumin (BSA-PBST) was added and reacted at room temperature for 2 hours. After washing with PBST 3 times, the SDMA antibody and the SmD3 antibody were diluted in BSA-PBST, and 100 µL of each was dispensed onto the plate and reacted at 4° C. overnight. After washing with PBST 3 times the next day, 100 µL of the secondary antibody diluted in BSA-PBST was added and reacted at room temperature for 1 hour. After washing with PBST 3 times, 100 µL of TMB substrate was added and reacted at room temperature for 10-20 minutes, and 100 µL of 1N sulfuric acid solution was added to terminate the reaction. Then, the absorbance at 450 nm was measured to calculate the degree of SDMA inhibition by the compound. (+++: more than 70%, ++: more than 30% and 70% or less, +: 30% or less)

TABLE 3

| Compound | SDMA inhibition (%) |
|---|---|
| Example 4 | ++ |
| Example 14 | +++ |
| Example 87 | ++ |
| Example 135 | +++ |

What is claimed is:

1. A compound represented by the following Formula 1, or an optical isomer, a stereoisomer or an isotopic variant thereof, or a pharmaceutically acceptable salt thereof:

[Formula 1]

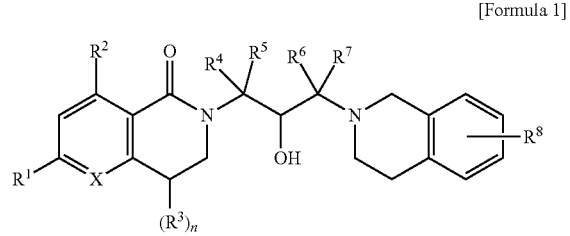

wherein
X is CH or N;
n is an integer from 0 to 2;
$R^1$ is -D-$R^9$ or

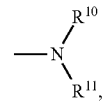

wherein D is a direct bond, —CH$_2$—, —O— or —C≡C—;
$R^9$ is halo, hydroxy, alkyl, hydroxyalkyl, dialkylaminoalkyl, saturated or unsaturated heterocyclyl, or saturated heterocyclyl-alkyl, wherein the saturated or unsaturated heterocyclyl is optionally substituted with one or more substituents selected from halo, alkyl, alkoxy, haloalkyl, hydroxyalkyl, alkoxyalkyl, alkylcarbonyl, alkoxycarbonyl and saturated heterocyclyl;
$R^{10}$ and $R^{11}$ are each independently hydrogen, alkyl, cycloalkyl, hydroxyalkyl, cycloalkyl-alkyl, alkylcarbonyl, hydroxyalkylcarbonyl, aralkyl, saturated heterocyclyl, saturated or unsaturated heterocyclyl-alkyl, unsaturated heterocyclyl-carbonyl, or saturated heterocyclyl-alkylcarbonyl; or $R^{10}$ and $R^{11}$ together with nitrogen (N) atom to which they are attached may form saturated or unsaturated heterocyclyl; wherein the saturated or unsaturated heterocyclyl is optionally substituted with one or more substituents selected from hydroxy, oxo, formyl (—CHO), cyano, alkyl, alkoxy, hydroxyalkyl, alkylcarbonyl, haloalkylcarbonyl, alkoxycarbonyl, alkylamino, alkylsulfonyl, alkoxyalkyl, aminocarbonyl, alkylcarbonylamino, alkylcarbonylalkylamino, alkoxyalkylalkylamino, dialkylamino, dialkylaminoalkyl, dialkylaminoalkoxy, dialkylaminocarbonyl and 4- to 10-membered, saturated heterocyclyl;
$R^2$ is hydrogen or halo;
$R^3$ is hydrogen, halo or alkyl, or together with carbon (C) atom to which they are attached may form cycloalkyl when n is 2;
$R^4$, $R^5$, $R^6$ and $R^7$ are each independently hydrogen or alkyl; and
$R^8$ is hydrogen, halo, alkyl, alkoxy or amino.

2. The compound, or optical isomer, stereoisomer or isotopic variant thereof, or pharmaceutically acceptable salt thereof according to claim 1, wherein
$R^1$ is -D-$R^9$, wherein D is a direct bond, —CH$_2$—, —O— or —C≡C—; and R$^9$ is halo, hydroxy, C$_1$-C$_7$ alkyl, hydroxy-C$_1$-C$_7$ alkyl, di(C$_1$-C$_7$ alkyl)amino-C$_1$-C$_7$ alkyl, 4- to 10-membered, saturated or unsaturated heterocyclyl, or 4- to 10-membered, saturated heterocyclyl-alkyl, wherein the saturated or unsaturated heterocyclyl has 1 to 3 heteroatoms selected from N, O and S; and the saturated or unsaturated heterocyclyl is optionally substituted with one or more substituents selected from halo, C$_1$-C$_7$ alkyl, C$_1$-C$_7$ alkoxy, halo-C$_1$-C$_7$ alkyl, hydroxy-C$_1$-C$_7$ alkyl, C$_1$-C$_7$ alkoxy-C$_1$-C$_7$ alkyl, C$_1$-C$_7$ alkylcarbonyl, C$_1$-C$_7$ alkoxycarbonyl, and 4- to 10-membered, saturated heterocyclyl having 1 to 3 heteroatoms selected from N, O and S.

3. The compound, or optical isomer, stereoisomer or isotopic variant thereof, or pharmaceutically acceptable salt thereof according to claim 2, wherein D is a direct bond; and R$^9$ is halo, hydroxy, C$_1$-C$_7$ alkyl or 4- to 10-membered, saturated or unsaturated heterocyclyl, wherein the saturated or unsaturated heterocyclyl has 1 to 3 heteroatoms selected from N, O and S; and the saturated or unsaturated heterocyclyl is optionally substituted with 1 to 3 substituents selected from halo, C$_1$-C$_7$ alkylcarbonyl and C$_1$-C$_7$ alkoxycarbonyl.

4. The compound, or optical isomer, stereoisomer or isotopic variant thereof, or pharmaceutically acceptable salt thereof according to claim 2, wherein D is —CH$_2$—, —O— or —C≡C—; and R$^9$ is hydroxy-C$_1$-C$_7$ alkyl, di(C$_1$-C$_7$ alkyl)amino-C$_1$-C$_7$ alkyl, 4- to 10-membered, saturated or unsaturated heterocyclyl, or 4- to 10-membered, saturated or unsaturated heterocyclyl-C$_1$-C$_7$ alkyl, wherein the saturated or unsaturated heterocyclyl has 1 to 3 heteroatoms selected from N, O and S; and the saturated or unsaturated heterocyclyl is optionally substituted with 1 to 3 substituents selected from C$_1$-C$_7$ alkyl, C$_1$-C$_7$ alkoxy, halo-C$_1$-C$_7$ alkyl, hydroxy-C$_1$-C$_7$ alkyl, C$_1$-C$_7$ alkoxy-C$_1$-C$_7$ alkyl, C$_1$-C$_7$ alkylcarbonyl, C$_1$-C$_7$ alkoxycarbonyl and 4- to 10-membered, saturated heterocyclyl having 1 to 3 heteroatoms selected from N, O and S.

5. The compound, or optical isomer, stereoisomer or isotopic variant thereof, or pharmaceutically acceptable salt thereof according to claim 2, wherein any one of the saturated or unsaturated heterocyclyl is independently selected from the group consisting of pyridyl, morpholinyl, oxazepanyl, dihydropyridinyl, tetrahydropyridinyl, piperidyl, piperazinyl, tetrahydropyranyl, azetidinyl and pyrrolidinyl.

6. The compound, or optical isomer, stereoisomer or isotopic variant thereof, or pharmaceutically acceptable salt thereof according to claim 1, wherein R$^1$ is

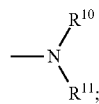

and

R$^{10}$ and R$^{11}$ are each independently hydrogen, C$_1$-C$_7$ alkyl, C$_3$-C$_7$ cycloalkyl, hydroxy-C$_1$-C$_7$ alkyl, C$_3$-C$_7$ cycloalkyl-C$_1$-C$_7$ alkyl, C$_1$-C$_7$ alkylcarbonyl, hydroxy-C$_1$-C$_7$ alkylcarbonyl, C$_6$-C$_{12}$ aryl-C$_1$-C$_7$ alkyl, saturated heterocyclyl, saturated or unsaturated heterocyclyl-C$_1$-C$_7$ alkyl, unsaturated heterocyclyl-carbonyl or saturated heterocyclyl-C$_1$-C$_7$ alkylcarbonyl; or R$^{10}$ and R$^{11}$ together with nitrogen (N) atom to which they are attached may form saturated or unsaturated heterocyclyl; wherein the heterocyclyl is optionally substituted with 1 to 3 substituents selected from hydroxy, oxo, formyl (—CHO), cyano, C$_1$-C$_7$ alkyl, C$_1$-C$_7$ alkoxy, hydroxy-C$_1$-C$_7$ alkyl, C$_1$-C$_7$ alkylcarbonyl, halo-C$_1$-C$_7$ alkylcarbonyl, C$_1$-C$_7$ alkoxycarbonyl, C$_1$-C$_7$ alkylamino, C$_1$-C$_7$ alkylsulfonyl, C$_1$-C$_7$ alkoxy-C$_1$-C$_7$ alkyl, aminocarbonyl, C$_1$-C$_7$ alkylcarbonylamino, C$_1$-C$_7$ alkylcarbonyl-C$_1$-C$_7$ alkylamino, (C$_1$-C$_7$ alkoxy-C$_1$-C$_7$ alkyl) (C$_1$-C$_7$ alkyl)amino, di(C$_1$-C$_7$ alkyl) amino, di(C$_1$-C$_7$ alkyl)amino-C$_1$-C$_7$ alkyl, di(C$_1$-C$_7$ alkyl)amino-C$_1$-C$_7$ alkoxy, di(C$_1$-C$_7$ alkyl)aminocarbonyl and saturated heterocyclyl.

7. The compound, or optical isomer, stereoisomer or isotopic variant thereof, or pharmaceutically acceptable salt thereof according to claim 6, wherein any one of the heterocyclyl is independently 4- to 10-membered, saturated or unsaturated hydrocarbon having 1 to 3 heteroatoms selected from N, O and S.

8. The compound, or optical isomer, stereoisomer or isotopic variant thereof, or pharmaceutically acceptable salt thereof according to claim 6, wherein any one of the heterocyclyl is independently selected from the group consisting of pyrrolidinyl, morpholinyl, tetrahydropyranyl, pyridyl, piperazinyl, azetidinyl, piperidyl, tetrahydrofuranyl, oxazolidinyl, 2-oxa-6-azaspiro[3.3]heptan-6yl, thiomorpholinyl, 2,5-diazabicyclo[2.2.1]heptanyl, 2-oxa-5-azabicyclo[2.2.1]heptanyl, diazepanyl, 4,7-diazaspiro[2.5]octanyl, 5,6,8,8a-tetrahydrooxazolo[3,4-a]pyrazinyl, azepanyl, 6,8-dihydro-5H-imidazo[1,2-a]pyrazinyl and oxetanyl.

9. The compound, or optical isomer, stereoisomer or isotopic variant thereof, or pharmaceutically acceptable salt thereof according to claim 1, wherein R$^2$ is hydrogen or halo;

R$^3$ is hydrogen, halo or C1-C7 alkyl; or together with carbon (C) atom to which they are attached may form C$_3$-C$_7$ cycloalkyl when n is 2;

R$^4$, R$^5$, R$^6$ and R$^7$ are each independently hydrogen or C$_1$-C$_7$ alkyl; and R$^8$ is hydrogen, halo, C$_1$-C$_7$ alkyl, C$_1$-C$_7$ alkoxy or amino.

10. The compound, or optical isomer, stereoisomer or isotopic variant thereof, or pharmaceutically acceptable salt thereof according to claim 1, wherein the compound is selected from the group consisting of:

6-bromo-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-pyrrolidin-1-yl-3,4-dihydroisoquinolin-1-one;

6-(cyclohexylamino)-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-morpholino-3,4-dihydroisoquinolin-1-one;

2-[(2R)-3-(3,4-dihydro-1H-isoquinolin-2-yl)-2-hydroxy-propyl]-6-(tetrahydropyran-4-ylamino)-3,4-dihydroisoquinolin-1-one;

6-(cyclohexylmethylamino)-2-[(2R)-3-(3,4-dihydro-1H-isoquinolin-2-yl)-2-hydroxy-propyl]-3,4-dihydroisoquinolin-1-one;

6-(benzylamino)-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-(4-pyridyl)-3,4-dihydroisoquinolin-1-one;
2-[(2R)-3-(3,4-dihydro-1H-isoquinolin-2-yl)-2-hydroxy-propyl]-6-(3-pyridyl)-3,4-dihydroisoquinolin-1-one;
2-[(2R)-3-(3,4-dihydro-1H-isoquinolin-2-yl)-2-hydroxy-propyl]-6-(4-pyridylmethylamino)-3,4-dihydroisoquinolin-1-one;
6-[cyclohexyl(methyl)amino]-2-[(2R)-3-(3,4-dihydro-1H-isoquinolin-2-yl)-2-hydroxy-propyl]-3,4-dihydroisoquinolin-1-one;
2-[(2R)-3-(3,4-dihydro-1H-isoquinolin-2-yl)-2-hydroxy-propyl]-6-(2-fluoro-4-pyridyl)-3,4-dihydroisoquinolin-1-one;
2-[(2R)-3-(3,4-dihydro-1H-isoquinolin-2-yl)-2-hydroxy-propyl]-6-propyl-3,4-dihydroisoquinolin-1-one;
2-[(2R)-3-(3,4-dihydro-1H-isoquinolin-2-yl)-2-hydroxy-propyl]-6-[(2R,6S)-2,6-dimethylmorpholin-4-yl]-3,4-dihydroisoquinolin-1-one;
2-[(2R)-3-(3,4-dihydro-1H-isoquinolin-2-yl)-2-hydroxy-propyl]-6-(6-fluoro-3-pyridyl)-3,4-dihydroisoquinolin-1-one;
2-[(2R)-3-(3,4-dihydro-1H-isoquinolin-2-yl)-2-hydroxy-propyl]-6-[(2R)-2-methylmorpholin-4-yl]-3,4-dihydroisoquinolin-1-one;
2-[(2R)-3-(3,4-dihydro-1H-isoquinolin-2-yl)-2-hydroxy-propyl]-6-(4-methylpiperazin-1-yl)-3,4-dihydroisoquinolin-1-one;
2-[(2R)-3-(3,4-dihydro-1H-isoquinolin-2-yl)-2-hydroxy-propyl]-6-(2-oxopyrrolidin-1-yl)-3,4-dihydroisoquinolin-1-one;
N-[2-[(2R)-3-(3,4-dihydro-1H-isoquinolin-2-yl)-2-hydroxy-propyl]-1-oxo-3,4-dihydroisoquinoline-6-yl]-2,2-dimethyl-propanamide;
2-[(2R)-3-(3,4-dihydro-1H-isoquinolin-2-yl)-2-hydroxy-propyl]-6-(2-oxoazetidin-1-yl)-3,4-dihydroisoquinolin-1-one;
2-[(2R)-3-(3,4-dihydro-1H-isoquinolin-2-yl)-2-hydroxy-propyl]-6-(2-oxo-1-piperidyl)-3,4-dihydroisoquinolin-1-one;
2-[(2R)-3-(3,4-dihydro-1H-isoquinolin-2-yl)-2-hydroxy-propyl]-6-(3-pyridylmethylamino)-3,4-dihydroisoquinolin-1-one;
2-[(2R)-3-(3,4-dihydro-1H-isoquinolin-2-yl)-2-hydroxy-propyl]-6-(tetrahydropyran-4-ylmethylamino)-3,4-dihydroisoquinolin-1-one;
6-[(1-acetyl-4-piperidyl)methylamino]-2-[(2R)-3-(3,4-dihydro-1H-isoquinolin-2-yl)-2-hydroxy-propyl]-3,4-dihydroisoquinolin-1-one;
2-[(2R)-3-(3,4-dihydro-1H-isoquinolin-2-yl)-2-hydroxy-propyl]-6-[(2-hydroxy-2-methyl-propyl)amino]-3,4-dihydroisoquinolin-1-one;
N-[2-[(2R)-3-(3,4-dihydro-1H-isoquinolin-2-yl)-2-hydroxy-propyl]-1-oxo-3,4-dihydroisoquinolin-6-yl]pyridine-3-carboxamide;
N-[2-[(2R)-3-(3,4-dihydro-1H-isoquinolin-2-yl)-2-hydroxy-propyl]-1-oxo-3,4-dihydroisoquinolin-6-yl]pyridine-4-carboxamide;
2-[(2R)-3-(3,4-dihydro-1H-isoquinolin-2-yl)-2-hydroxy-propyl]-6-(3,5-dimethyl-1-piperidyl)-3,4-dihydroisoquinolin-1-one;
2-[(2R)-3-(3,4-dihydro-1H-isoquinolin-2-yl)-2-hydroxy-propyl]-6-(3,5-dimethylpiperazin-1-yl)-3,4-dihydroisoquinolin-1-one;
2-[(2R)-3-(3,4-dihydro-1H-isoquinolin-2-yl)-2-hydroxy-propyl]-6-(tetrahydrofuran-3-ylmethylamino)-3,4-dihydroisoquinolin-1-one;
2-[(2R)-3-(3,4-dihydro-1H-isoquinolin-2-yl)-2-hydroxy-propyl]-6-(4-piperidylmethylamino)-3,4-dihydroisoquinolin-1-one;
6-[(1-acetyl-4-piperidyl)amino]-2-[(2R)-3-(3,4-dihydro-1H-isoquinolin-2-yl)-2-hydroxy-propyl]-3,4-dihydroisoquinolin-1-one;
N-[2-[(2R)-3-(3,4-dihydro-1H-isoquinolin-2-yl)-2-hydroxy-propyl]-1-oxo-3,4-dihydroisoquinolin-6-yl]-2-morpholino-acetamide;
2-[(2R)-3-(3,4-dihydro-1H-isoquinolin-2-yl)-2-hydroxy-propyl]-6-(4-piperidylamino)-3,4-dihydroisoquinolin-1-one;
2-[(2R)-3-(3,4-dihydro-1H-isoquinolin-2-yl)-2-hydroxy-propyl]-6-[4-(hydroxymethyl)-1-piperidyl]-3,4-dihydroisoquinolin-1-one;
2-[(2R)-3-(3,4-dihydro-1H-isoquinolin-2-yl)-2-hydroxy-propyl]-6-[3-(hydroxymethyl)-1-piperidyl]-3,4-dihydroisoquinolin-1-one;
2-[(2R)-3-(3,4-dihydro-1H-isoquinolin-2-yl)-2-hydroxy-propyl]-6-(4-hydroxy-1-piperidyl)-3,4-dihydroisoquinolin-1-one;
2-[(2R)-3-(3,4-dihydro-1H-isoquinolin-2-yl)-2-hydroxy-propyl]-6-(3-hydroxy-1-piperidyl)-3,4-dihydroisoquinolin-1-one;
2-[(2R)-3-(3,4-dihydro-1H-isoquinolin-2-yl)-2-hydroxy-propyl]-6-oxazolidin-3-yl-3,4-dihydroisoquinolin-1-one;
2-[(2R)-3-(3,4-dihydro-1H-isoquinolin-2-yl)-2-hydroxy-propyl]-6-(3-methylmorpholin-4-yl)-3,4-dihydroisoquinolin-1-one;
N-[2-[(2R)-3-(3,4-dihydro-1H-isoquinolin-2-yl)-2-hydroxy-propyl]-1-oxo-3,4-dihydroisoquinolin-6-yl]-2-hydroxy-acetamide;
N-[2-[(2R)-3-(3,4-dihydro-1H-isoquinolin-2-yl)-2-hydroxy-propyl]-1-oxo-3,4-dihydroisoquinolin-6-yl]acetamide;
2-[(2R)-3-(3,4-dihydro-1H-isoquinolin-2-yl)-2-hydroxy-propyl]-6-(morpholinomethyl)-3,4-dihydroisoquinolin-1-one;
2-[(2R)-3-(3,4-dihydro-1H-isoquinolin-2-yl)-2-hydroxy-propyl]-6-(2-oxa-6-azaspiro[3.3]heptan-6-yl)-3,4-dihydroisoquinolin-1-one;
3-[2-[(2R)-3-(3,4-dihydro-1H-isoquinolin-2-yl)-2-hydroxy-propyl]-1-oxo-3,4-dihydroisoquinolin-6-yl]oxazolidin-2-one;
2-[(2R)-3-(3,4-dihydro-1H-isoquinolin-2-yl)-2-hydroxy-propyl]-6-[3-(hydroxymethyl) azetidin-1-yl]-3,4-dihydroisoquinolin-1-one;
2-[(2R)-3-(3,4-dihydro-1H-isoquinolin-2-yl)-2-hydroxy-propyl]-6-[(2S)-2-methylmorpholin-4-yl]-3,4-dihydroisoquinolin-1-one;
2-[(2R)-3-(3,4-dihydro-1H-isoquinolin-2-yl)-2-hydroxy-propyl]-6-(4-methoxy-1-piperidyl)-3,4-dihydroisoquinolin-1-one;
2-[(2R)-3-(3,4-dihydro-1H-isoquinolin-2-yl)-2-hydroxy-propyl]-6-(1,1-dioxo-1,4-thiazinan-4-yl)-3,4-dihydroisoquinolin-1-one;
2-[(2R)-3-(3,4-dihydro-1H-isoquinolin-2-yl)-2-hydroxy-propyl]-6-(tetrahydrofuran-3-ylamino)-3,4-dihydroisoquinolin-1-one;
2-[(2R)-3-(3,4-dihydro-1H-isoquinolin-2-yl)-2-hydroxy-propyl]-6-(oxetan-3-ylamino)-3,4-dihydroisoquinolin-1-one;
6-(4-acetylpiperazin-1-yl)-2-[(2R)-3-(3,4-dihydro-1H-isoquinolin-2-yl)-2-hydroxy-propyl]-3,4-dihydroisoquinolin-1-one;

tert-butyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate;

2-[(2R)-3-(3,4-dihydro-1H-isoquinolin-2-yl)-2-hydroxy-propyl]-6-(1,4-oxazepan-4-ylmethyl)-3,4-dihydroisoquinolin-1-one;

2-[(2R)-3-(3,4-dihydro-1H-isoquinolin-2-yl)-2-hydroxy-propyl]-6-(4-methyl-3-oxo-piperazin-1-yl)-3,4-dihydroisoquinolin-1-one;

tert-butyl 4-[2-[(2R)-3-(3,4-dihydro-1H-isoquinolin-2-yl)-2-hydroxy-propyl]-1-oxo-3,4-dihydroisoquinolin-6-yl]-3,6-dihydro-2H-pyridine-1-carboxylate;

2-[(2R)-3-(3,4-dihydro-1H-isoquinolin-2-yl)-2-hydroxy-propyl]-6-(1,2,3,6-tetrahydropyridin-4-yl)-3,4-dihydroisoquinolin-1-one;

2-[(2R)-3-(3,4-dihydro-1H-isoquinolin-2-yl)-2-hydroxy-propyl]-6-piperazin-1-yl-3,4-dihydroisoquinolin-1-one;

2-[(2R)-3-(3,4-dihydro-1H-isoquinolin-2-yl)-2-hydroxy-propyl]-6-(4-methylsulfonylpiperazin-1-yl)-3,4-dihydroisoquinolin-1-one;

methyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate;

6-(1-acetyl-3,6-dihydro-2H-pyridin-4-yl)-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-[4-(2,2,2-trifluoro acetyl) piperazin-1-yl]-3,4-dihydroisoquinolin-1-one;

tert-butyl 4-[2-[(2R)-3-(3,4-dihydro-1H-isoquinolin-2-yl)-2-hydroxy-propyl]-1-oxo-3,4-dihydroisoquinolin-6-yl]piperidine-1-carboxylate;

[(2R)-3-(3,4-dihydro-1H-isoquinolin-2-yl)-2-hydroxy-propyl]-6-(4-isopropylpiperazin-1-yl)-3,4-dihydroisoquinolin-1-one;

ethyl 4-[2-[(2R)-3-(3,4-dihydro-1H-isoquinolin-2-yl)-2-hydroxy-propyl]-1-oxo-3,4-dihydroisoquinolin-6-yl]piperazine-1-carboxylate;

2-[(2R)-3-(3,4-dihydro-1H-isoquinolin-2-yl)-2-hydroxy-propyl]-6-[(4-methoxy-1-piperidyl)methyl]-3,4-dihydroisoquinolin-1-one;

6-(1-acetyl-4-piperidyl)-2-[(2R)-3-(3,4-dihydro-1H-isoquinolin-2-yl)-2-hydroxy-propyl]-3,4-dihydroisoquinolin-1-one;

6-[(4-acetylpiperazin-1-yl)methyl]-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-(4-propanoylpiperazin-1-yl)-3,4-dihydroisoquinolin-1-one;

2-[(2R)-3-(3,4-dihydro-1H-isoquinolin-2-yl)-2-hydroxy-propyl]-6-[4-(2-methylpropanoyl) piperazin-1-yl]-3,4-dihydroisoquinolin-1-one;

2-[(2R)-3-(3,4-dihydro-1H-isoquinolin-2-yl)-2-hydroxy-propyl]-6-[4-(2,2-dimethylpropanoyl) piperazin-1-yl]-3,4-dihydroisoquinolin-1-one;

tert-butyl 5-[2-[(2R)-3-(3,4-dihydro-1H-isoquinolin-2-yl)-2-hydroxy-propyl]-1-oxo-3,4-dihydroisoquinolin-6-yl]-2,5-diazabicyclo[2.2.1]heptane-2-carboxylate;

2-[(2R)-3-(3,4-dihydro-1H-isoquinolin-2-yl)-2-hydroxy-propyl]-6-(2-oxa-5-azabicyclo[2.2.1]heptan-5-yl)-3,4-dihydroisoquinolin-1-one;

2-[(2R)-3-(3,4-dihydro-1H-isoquinolin-2-yl)-2-hydroxy-propyl]-6-hydroxy-3,4-dihydroisoquinolin-1-one;

2-chloro-6-[(2R)-3-(3,4-dihydro-1H-isoquinolin-2-yl)-2-hydroxy-propyl]-7,8-dihydro-1,6-naphthyridin-5-one;

6-(2,5-diazabicyclo[2.2.1]heptan-2-yl)-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-(3-piperidylamino)-3,4-dihydroisoquinolin-1-one;

tert-butyl 4-[2-[(2R)-3-(3,4-dihydro-1H-isoquinolin-2-yl)-2-hydroxy-propyl]-1-oxo-3,4-dihydroisoquinolin-6-yl]-1,4-diazepane-1-carboxylate;

2-[(2R)-3-(3,4-dihydro-1H-isoquinolin-2-yl)-2-hydroxy-propyl]-6-(4-methyl-3-oxo-1,4-diazepan-1-yl)-3,4-dihydroisoquinolin-1-one;

6-(4-acetyl-1,4-diazepan-1-yl)-2-[(2R)-3-(3,4-dihydro-1H-isoquinolin-2-yl)-2-hydroxy-propyl]-3,4-dihydroisoquinolin-1-one;

6-(5-acetyl-2,5-diazabicyclo[2.2.1]heptan-2-yl)-2-[(2R)-3-(3,4-dihydro-1H-isoquinolin-2-yl)-2-hydroxy-propyl]-3,4-dihydroisoquinolin-1-one;

6-(4-acetyl-4,7-diazaspiro[2.5]octan-7-yl)-2-[(2R)-3-(3,4-dihydro-1H-isoquinolin-2-yl)-2-hydroxy-propyl]-3,4-dihydroisoquinolin-1-one;

6-[(1-acetyl-4-piperidyl) methoxy]-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-(4-methyl-5-oxo-1,4-diazepan-1-yl)-3,4-dihydroisoquinolin-1-one;

2-[(2R)-3-(3,4-dihydro-1H-isoquinolin-2-yl)-2-hydroxy-propyl]-6-(4-isopropyl-3-oxo-piperazin-1-yl)-3,4-dihydroisoquinolin-1-one;

6-(4-acetyl-2-oxo-piperazin-1-yl)-2-[(2R)-3-(3,4-dihydro-1H-isoquinolin-2-yl)-2-hydroxy-propyl]-3,4-dihydroisoquinolin-1-one;

4-[2-[(2R)-3-(3,4-dihydro-1H-isoquinolin-2-yl)-2-hydroxy-propyl]-1-oxo-3,4-dihydroisoquinolin-6-yl]piperazine-1-carbaldehyde;

2-(4-acetylpiperazin-1-yl)-6-[(2R)-3-(3,4-dihydro-1H-isoquinolin-2-yl)-2-hydroxy-propyl]-7,8-dihydro-1,6-naphthyridin-5-one;

6-[(2R)-3-(3,4-dihydro-1H-isoquinolin-2-yl)-2-hydroxy-propyl]-2-morpholino-7,8-dihydro-1,6-naphthyridin-5-one;

N-[1-[2-[(2R)-3-(3,4-dihydro-1H-isoquinolin-2-yl)-2-hydroxy-propyl]-1-oxo-3,4-dihydroisoquinolin-6-yl]-4-piperidyl]-N-methyl-acetamide;

2-[(2R)-3-(3,4-dihydro-1H-isoquinolin-2-yl)-2-hydroxy-propyl]-6-tetrahydropyran-4-yloxy-3,4-dihydroisoquinolin-1-one;

N-[1-[2-[(2R)-3-(3,4-dihydro-1H-isoquinolin-2-yl)-2-hydroxy-propyl]-1-oxo-3,4-dihydroisoquinolin-6-yl]-4-piperidyl]acetamide;

6-[(1-acetyl-3-piperidyl)amino]-2-[(2R)-3-(3,4-dihydro-1H-isoquinolin-2-yl)-2-hydroxy-propyl]-3,4-dihydroisoquinolin-1-one;

7-[2-[(2R)-3-(3,4-dihydro-1H-isoquinolin-2-yl)-2-hydroxy-propyl]-1-oxo-3,4-dihydroisoquinolin-6-yl]-5,6,8,8a-tetrahydro-1H-oxazolo[3,4-a]pyrazin-3-one;

6-[(1-acetyl-4-piperidyl)oxy]-2-[(2R)-3-(3,4-dihydro-1H-isoquinolin-2-yl)-2-hydroxy-propyl]-3,4-dihydroisoquinolin-1-one;

6-(1-acetylazetidin-3-yl)oxy-2-[(2R)-3-(3,4-dihydro-1H-isoquinolin-2-yl)-2-hydroxy-propyl]-3,4-dihydroisoquinolin-1-one;

1-[2-[(2R)-3-(3,4-dihydro-1H-isoquinolin-2-yl)-2-hydroxy-propyl]-1-oxo-3,4-dihydroisoquinolin-6-yl]-N,N-dimethyl-piperidine-4-carboxamide;

6-[(1-acetylazepan-4-yl)amino]-2-[(2R)-3-(3,4-dihydro-1H-isoquinolin-2-yl)-2-hydroxy-propyl]-3,4-dihydroisoquinolin-1-one;

6-[(1-acetylpyrrolidin-3-yl)amino]-2-[(2R)-3-(3,4-dihydro-1H-isoquinolin-2-yl)-2-hydroxy-propyl]-3,4-dihydroisoquinolin-1-one;

4-[2-[(2R)-3-(3,4-dihydro-1H-isoquinolin-2-yl)-2-hydroxy-propyl]-1-oxo-3,4-dihydroisoquinolin-6-yl]piperazine-1-carboxamide;

4-[2-[(2R)-3-(3,4-dihydro-1H-isoquinolin-2-yl)-2-hydroxy-propyl]-1-oxo-3,4-dihydroisoquinolin-6-yl]piperazine-1-carbonitrile;

6-(6,8-dihydro-5H-imidazo[1,2-a]pyrazin-7-yl)-2-[(2R)-3-(3,4-dihydro-1H-isoquinoline-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-(3,4-dimethyl-5-oxo-piperazin-1-yl)-3,4-dihydroisoquinolin-1-one;

6-(4-acetylpiperazin-1-yl)-2-[(2R)-3-(3,4-dihydro-1H-isoquinolin-2-yl)-2-hydroxy-propyl]-4,4-dimethyl-3H-isoquinolin-1-one;

6-(4-acetylpiperazin-1-yl)-2-[(2R)-3-(3,4-dihydro-1H-isoquinolin-2-yl)-2-hydroxy-propyl]spiro[3H-isoquinoline-4,1'-cyclopropane]-1-one;

2-[(2R)-3-(3,4-dihydro-1H-isoquinolin-2-yl)-2-hydroxy-propyl]-6-(4-pyrrolidin-1-yl-1-piperidyl)-3,4-dihydroisoquinolin-1-one;

2-[(2R)-3-(3,4-dihydro-1H-isoquinolin-2-yl)-2-hydroxy-propyl]-6-[4-(1-piperidyl)-1-piperidyl]-3,4-dihydroisoquinolin-1-one;

2-[(2R)-3-(3,4-dihydro-1H-isoquinolin-2-yl)-2-hydroxy-propyl]-6-(4-morpholino-1-piperidyl)-3,4-dihydroisoquinolin-1-one;

2-[(2R)-3-(3,4-dihydro-1H-isoquinolin-2-yl)-2-hydroxy-propyl]-6-[4-(2-methoxyethyl) piperazin-1-yl]-3,4-dihydroisoquinolin-1-one;

2-[(2R)-3-(3,4-dihydro-1H-isoquinolin-2-yl)-2-hydroxy-propyl]-6-[4-(dimethylamino)-1-piperidyl]-3,4-dihydroisoquinolin-1-one;

2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one;

2-[(2R)-3-(3,4-dihydro-1H-isoquinolin-2-yl)-2-hydroxy-propyl]-4,4-dimethyl-6-morpholino-3H-isoquinolin-1-one;

2-[(2R)-3-(3,4-dihydro-1H-isoquinolin-2-yl)-2-hydroxy-propyl]-6-(2-morpholinoethoxy)-3,4-dihydroisoquinolin-1-one;

2-[(2R)-3-(3,4-dihydro-1H-isoquinolin-2-yl)-2-hydroxy-propyl]-6-[(1-ethyl-4-piperidyl)oxy]-3,4-dihydroisoquinolin-1-one;

2-[(2R)-3-(3,4-dihydro-1H-isoquinolin-2-yl)-2-hydroxy-propyl]-6-[(1-ethyl-4-piperidyl)methyloxy]-3,4-dihydroisoquinolin-1-one;

2-[(2R)-3-(3,4-dihydro-1H-isoquinolin-2-yl)-2-hydroxy-propyl]-6-[3-(dimethylamino)-1-piperidyl]-3,4-dihydroisoquinolin-1-one;

2-[(2R)-3-(3,4-dihydro-1H-isoquinolin-2-yl)-2-hydroxy-propyl]-6-[4-[(dimethylamino)methyl]-1-piperidyl]-3,4-dihydroisoquinolin-1-one;

6-[4-(diethylamino)-1-piperidyl]-2-[(2R)-3-(3,4-dihydro-1H-isoquinolin-2-yl)-2-hydroxy-propyl]-3,4-dihydroisoquinolin-1-one;

2-[(2R)-3-(3,4-dihydro-1H-isoquinolin-2-yl)-2-hydroxy-propyl]-6-[4-[2-(dimethylamino) ethoxy]-1-piperidyl]-3,4-dihydroisoquinolin-1-one;

2-[(2R)-3-(3,4-dihydro-1H-isoquinolin-2-yl)-2-hydroxy-propyl]-6-[4-[2-methoxyethyl(methyl)amino]-1-piperidyl]-3,4-dihydroisoquinolin-1-one;

2-[(2R)-3-(3,4-dihydro-1H-isoquinolin-2-yl)-2-hydroxy-propyl]-6-[4-(oxetan-3-yl) piperazin-1-yl]-3,4-dihydroisoquinolin-1-one;

2-[(2R)-3-(3,4-dihydro-1H-isoquinolin-2-yl)-2-hydroxy-propyl]-6-(4-tetrahydropyran-4-ylpiperazin-1-yl)-3,4-dihydroisoquinolin-1-one;

6-[4-(diethylamino)-1-piperidyl]-2-[(2R)-3-(3,4-dihydro-1H-isoquinolin-2-yl)-2-hydroxy-propyl]-4,4-dimethyl-3H-isoquinolin-1-one;

2-[(2R)-3-(3,4-dihydro-1H-isoquinolin-2-yl)-2-hydroxy-propyl]-4,4-dimethyl-6-(4-pyrrolidin-1-yl-1-piperidyl)-3H-isoquinolin-1-one;

4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde;

2-[(2R)-3-(3,4-dihydro-1H-isoquinolin-2-yl)-2-hydroxy-propyl]-6-[4-(dimethylamino)-1-piperidyl]-4,4-dimethyl-3H-isoquinolin-1-one; dihydrochloride;

2-[(2R)-3-(3,4-dihydro-1H-isoquinolin-2-yl)-2-hydroxy-propyl]-6-(4-tetrahydrofuran-3-ylpiperazin-1-yl)-3,4-dihydroisoquinolin-1-one;

6-(4-acetylpiperazin-1-yl)-2-[(2R)-3-(3,4-dihydro-1H-isoquinolin-2-yl)-2-hydroxy-propyl]-8-fluoro-3,4-dihydroisoquinolin-1-one;

6-(4-acetylpiperazin-1-yl)-2-[3-(3,4-dihydro-1H-isoquinolin-2-yl)-2-hydroxy-1-methyl-propyl]-3,4-dihydroisoquinolin-1-one;

4-[2-[(2R)-3-(3,4-dihydro-1H-isoquinolin-2-yl)-2-hydroxy-propyl]-4,4-dimethyl-1-oxo-3H-isoquinolin-6-yl]piperazine-1-carbaldehyde; hydrochloride;

2-[(2R)-3-(3,4-dihydro-1H-isoquinolin-2-yl)-2-hydroxy-propyl]-6-[(1-ethyl-4-piperidyl)oxy]-4,4-dimethyl-3H-isoquinolin-1-one;

2-[(2R)-3-(3,4-dihydro-1H-isoquinolin-2-yl)-2-hydroxy-propyl]-4,4-difluoro-6-morpholino-3H-isoquinolin-1-one;

2-[(2R)-3-(3,4-dihydro-1H-isoquinolin-2-yl)-2-hydroxy-propyl]-6-(1-methylpyrrolidin-3-yl)oxy-3,4-dihydroisoquinolin-1-one;

2-[(2R)-3-(3,4-dihydro-1H-isoquinolin-2-yl)-2-hydroxy-propyl]-6-(1-ethylpyrrolidin-3-yl)oxy-3,4-dihydroisoquinolin-1-one;

2-[(2R)-3-(3,4-dihydro-1H-isoquinolin-2-yl)-2-hydroxy-propyl]-6-[(1-methyl-4-piperidyl)oxy]-3,4-dihydroisoquinolin-1-one;

2-[(2R)-3-(3,4-dihydro-1H-isoquinolin-2-yl)-2-hydroxy-propyl]-6-[[1-(oxetan-3-yl)-4-piperidyl]oxy]-3,4-dihydroisoquinolin-1-one;

2-[(2R)-3-(3,4-dihydro-1H-isoquinolin-2-yl)-2-hydroxy-propyl]-6-(3-hydroxyprop-1-ynyl)-3,4-dihydroisoquinolin-1-one;

2-[(2R)-3-(3,4-dihydro-1H-isoquinolin-2-yl)-2-hydroxy-propyl]-6-[2-(4-pyridyl) ethynyl]-3,4-dihydroisoquinolin-1-one;

2-[(2R)-3-(3,4-dihydro-1H-isoquinolin-2-yl)-2-hydroxy-propyl]-6-[(1-methyl-3-piperidyl)oxy]-3,4-dihydroisoquinolin-1-one;

2-[(2R)-3-(3,4-dihydro-1H-isoquinolin-2-yl)-2-hydroxy-propyl]-6-[[1-(2-fluoroethyl)-3-piperidyl]oxy]-3,4-dihydroisoquinolin-1-one;

2-[(2R)-3-(3,4-dihydro-1H-isoquinolin-2-yl)-2-hydroxy-propyl]-6-[3-(dimethylamino) prop-1-ynyl]-3,4-dihydroisoquinolin-1-one;

2-[(2R)-3-(3,4-dihydro-1H-isoquinolin-2-yl)-2-hydroxypropyl]-6-[[1-(2-methoxyethyl)-4-piperidyl]oxy]-3,4-dihydroisoquinolin-1-one;

6-[(2R)-3-(3,4-dihydro-1H-isoquinolin-2-yl)-2-hydroxypropyl]-2-[[1-(2-methoxyethyl)-4-piperidyl]oxy]-7,8-dihydro-1,6-naphthyridin-5-one;

6-[(2R)-3-(3,4-dihydro-1H-isoquinolin-2-yl)-2-hydroxypropyl]-2-[[1-[(2R)-2-hydroxypropyl]-4-piperidyl]oxy]-7,8-dihydro-1,6-naphthyridin-5-one;

6-[(2R)-3-(3,4-dihydro-1H-isoquinolin-2-yl)-2-hydroxypropyl]-2-[[1-(2-hydroxy-2-methyl-propyl)-4-piperidyl]oxy]-7,8-dihydro-1,6-naphthyridin-5-one; and 6-[(2R)-3-(3,4-dihydro-1H-isoquinolin-2-yl)-2-hydroxypropyl]-2-[[1-(oxetan-3-yl)-4-piperidyl]oxy]-7,8-dihydro-1,6-naphthyridin-5-one.

11. A pharmaceutical composition for the prevention or treatment of a disease associated with protein arginine methyltransferase 5 (PRMT5) inhibition comprising a therapeutically effective amount of the compound, or optical isomer, stereoisomer or isotopic variant thereof, or pharmaceutically acceptable salt thereof as defined in claim 1 as an active ingredient, together with a pharmaceutically acceptable carrier.

12. The pharmaceutical composition according to claim 11, wherein the disease associated with PRMT5 inhibition is selected from cancer, blood disease, autoimmune disease, inflammatory disease and neurodegenerative disease.

13. The pharmaceutical composition according to claim 12, wherein the cancer is selected from the group consisting of acoustic neuroma, adenocarcinoma, adrenal cancer, anal cancer, angiosarcoma, benign monoclonal gammaglobulinopathy, cholangiocarcinoma, bladder cancer, breast cancer, brain cancer, lymphoma, multiple myeloma, lacrimal gland tumor, bronchial cancer, cervical cancer, craniopharyngioma, colorectal cancer, epithelial carcinoma, epithelial cell tumor, endothelial sarcoma, endometrial cancer, esophageal cancer, Barrett's adenocarcinoma, Ewing's sarcoma, eye cancer, gallbladder cancer, gastric cancer, gastrointestinal stromal tumor (GIST), head and neck cancer, oral cancer, oral squamous cell carcinoma (OSCC), throat cancer, hematopoietic cancer, hemangioblastoma, inflammatory myofibroblast tumor, immune cell amyloidosis, kidney cancer, liver cancer, lung cancer, myelodysplastic syndrome (MDS), mesothelioma, myeloproliferative disorder (MPD), chronic idiopathic myelofibrosis, chronic myelogenous leukemia (CML), chronic neutrophilic leukemia (CNL), neuroblastoma, neurofibroma, neuroendocrine cancer, osteosarcoma, ovarian cancer, papillary adenocarcinoma, pancreatic cancer, penile cancer, prostate cancer, rectal cancer, rhabdomyosarcoma, salivary gland cancer, skin cancer, small intestine cancer, soft tissue sarcoma, thyroid cancer, urethral cancer, vaginal cancer and vulvar cancer.

14. The pharmaceutical composition according to claim 13, wherein the brain cancer is selected from the group consisting of meningioma, glioma, medulloblastoma, glioblastoma and brain metastasis cancer.

15. The pharmaceutical composition according to claim 12, wherein the blood disease is hemoglobinemia or sickle cell anemia; the autoimmune disease is selected from the group consisting of rheumatoid arthritis, spinal arthritis, gouty arthritis, degenerative joint disease, osteoarthritis, systemic lupus erythematosus, multiple sclerosis, psoriatic arthritis, juvenile arthritis, asthma, atherosclerosis, osteoporosis, bronchitis, tendinitis, psoriasis, eczema, burns, dermatitis, pruritus, enuresis, eosinophilic disease, peptic ulcer, localized enteritis, diverticulitis, gastrointestinal bleeding, eosinophilic esophagitis, eosinophilic gastritis, eosinophilic gastroenteritis and eosinophilic colitis; the inflammatory disease is selected from the group consisting of acne-related inflammation, aplastic anemia, hemolytic autoimmune anemia, rhinitis, asthma, polyarteritis, temporal arteritis, periarteritis nodosa, Takayasu's arteritis, crystalline arthritis, osteoarthritis, psoriatic arthritis, gouty arthritis, reactive arthritis, rheumatoid arthritis, amyotrophic lateral sclerosis, autoimmune disease, allergic or allergic reaction, atherosclerosis, bronchitis, bursitis, chronic prostatitis, conjunctivitis, chronic obstructive pulmonary disease, dermatomyositis, type I diabetes, type 2 diabetes, psoriasis, eczema, eczema hypersensitivity reaction, burn, dermatitis, pruritus, endometriosis, infection, ischemic heart disease, glomerulonephritis, gingivitis, irritability, migraine, tension headache, postoperative intestinal obstruction, intestinal obstruction during sepsis, idiopathic thrombocytopenia purpura, bladder pain syndrome, peptic ulcer, localized enteritis, diverticulitis, gastric bleeding, eosinophilic esophagitis, eosinophilic gastritis, eosinophilic gastroenteritis, eosinophilic colitis, gastritis, diarrhea, gastroesophageal reflux disease, Crohn's disease, ulcerative colitis, collagenous colitis, lymphocytic colitis, ischemic colitis, bypass colitis, Behcet's syndrome, indeterminate colitis, inflammatory bowel syndrome (IBS), lupus, ecchymosis, myasthenia gravis and myocardial ischemia; and the neurodegenerative disease is selected from the group consisting of motor neuron disease, Pick's disease, Alzheimer's disease, AIDS-related dementia, Parkinson's disease, amyotrophic lateral sclerosis, retinal pigmentation, spinal muscular atrophy and cerebellar degeneration.

* * * * *